United States Patent
Peters et al.

(10) Patent No.: US 10,870,724 B2
(45) Date of Patent: Dec. 22, 2020

(54) HIGH HEAT MONOMERS AND METHODS OF USE THEREOF

(71) Applicant: SABIC GLOBAL TECHNOLOGIES B.V., Bergen op Zoom (NL)

(72) Inventors: Edward Norman Peters, Lenox, MA (US); Scott Michael Fisher, Delmar, NY (US); Jaykisor Pal, Bangalore (IN)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/571,267

(22) Filed: Sep. 16, 2019

(65) Prior Publication Data

US 2020/0010608 A1    Jan. 9, 2020

Related U.S. Application Data

(63) Continuation of application No. 15/327,416, filed as application No. PCT/US2015/041338 on Jul. 21, 2015, now Pat. No. 10,465,037.

(60) Provisional application No. 62/027,600, filed on Jul. 22, 2014.

(51) Int. Cl.
| | |
|---|---|
| C08G 59/06 | (2006.01) |
| C07D 405/12 | (2006.01) |
| C07D 303/18 | (2006.01) |
| C08G 59/24 | (2006.01) |
| C07D 303/27 | (2006.01) |
| C07D 405/14 | (2006.01) |
| C09D 163/00 | (2006.01) |

(52) U.S. Cl.
CPC ......... *C08G 59/063* (2013.01); *C07D 303/18* (2013.01); *C07D 303/27* (2013.01); *C07D 405/12* (2013.01); *C07D 405/14* (2013.01); *C08G 59/245* (2013.01); *C09D 163/00* (2013.01)

(58) Field of Classification Search
None
See application file for complete search history.

(56) References Cited

U.S. PATENT DOCUMENTS

| | | | |
|---|---|---|---|
| 4,196,006 | A | 4/1980 | Inata et al. |
| 4,707,534 | A | 11/1987 | Schultz |
| 5,218,061 | A | 6/1993 | Kajiwara et al. |
| 5,814,373 | A | 9/1998 | White et al. |
| 6,320,020 | B1 | 11/2001 | Takum et al. |
| 7,695,895 | B2 | 4/2010 | Miura et al. |
| 8,252,512 | B2 | 8/2012 | Mihara et al. |
| 2009/0054587 | A1 | 2/2009 | Oshimi et al. |
| 2009/0181165 | A1 | 7/2009 | Liang et al. |
| 2010/0179353 | A1 | 7/2010 | Nakanishi et al. |
| 2013/0052381 | A1 | 2/2013 | Gallucci et al. |
| 2013/0202873 | A1 | 8/2013 | Mizuki et al. |
| 2013/0277627 | A1 | 10/2013 | Tseng et al. |
| 2013/0323994 | A1 | 12/2013 | Kiyoyanagi et al. |
| 2014/0066636 | A1 | 3/2014 | Yanagisawa |
| 2014/0179828 | A1 | 6/2014 | Hefner, Jr. et al. |
| 2017/0158807 | A1 | 6/2017 | Yoshimoto et al. |
| 2019/0322653 | A1 | 10/2019 | Peters et al. |

FOREIGN PATENT DOCUMENTS

| | | |
|---|---|---|
| EP | 0274209 A1 | 7/1988 |
| EP | 0377909 A1 | 7/1990 |
| EP | 0987567 A1 | 3/2000 |
| EP | 2014691 A1 | 1/2009 |
| FR | 1519027 A | 3/1968 |
| GB | 1158606 | 2/1967 |
| GB | 1158606 A | 7/1969 |
| JP | 63150270 A | 6/1988 |
| JP | 02229181 A | 9/1990 |
| JP | 08092231 A | 4/1996 |
| JP | 10130371 A | 5/1998 |
| JP | 2003034714 A | 2/2003 |
| JP | 2003082061 A | 3/2003 |
| JP | 2004283497 A | 10/2004 |
| JP | 2010174078 A | 8/2010 |
| JP | 2014125507 A | 7/2014 |
| WO | 2012145330 A1 | 10/2012 |
| WO | 2014039645 A1 | 3/2014 |
| WO | 2015037584 A1 | 3/2015 |

OTHER PUBLICATIONS

A Chandramohan et al: "Thermal, electrical and morphological properties of DGEBA/DDM and TGDDM/DDM epoxies modified by a flexible diepoxide and octaphenylamine-POSS", Journal of Reinforced Plastics and Composites, vol. 32, No. 9, May 22, 2013, pp. 602-611.
International Search Report for PCT/US2015/041338 dated Dec. 4, 2016, 6 pages.
Summary of CN Office Action for Applicatio No. 2015800399137 dated Apr. 10, 2018.
Tadeusz Matynia et al: "One- and Two-step Syntheses of Unstaurated Expoxyfumarate Resins Containing Bromine", International Jorunal of Polymeric Materials., vol. 46, No. 1-2, Jun. 1, 2000, pp. 285-292.
Written Opinion of the International Searching Authority for PCT/US2015/041338 dated Dec. 4, 2016, 9 pages.
Yu Zhou et al: "Structural Optimization and Biological Evaluation of Substituted Bisphenol A Dertivative as [beta]-Amyloid Peptide Aggregation Inhibitors", Journal of Medicinal Chemistry, vol. 53, No. 15, Aug. 12, 2010, pp. 5449-5466.
Ito et al., "Polymeric Materials for Micoelectronic Applications" ACS Symposium Series, 579, 220-233, 1994.

*Primary Examiner* — Megan McCulley
(74) *Attorney, Agent, or Firm* — Cantor Colburn LLP

(57) ABSTRACT

High purity epoxide compounds methods for preparing the high purity epoxide compounds, and compositions derived from the epoxide compounds are provided. Also provided are materials and articles derived from the epoxide compounds.

16 Claims, 14 Drawing Sheets

HIGH HEAT MONOMERS AND METHODS OF USE THEREOF

CROSS REFERENCE TO RELATED APPLICATIONS

This application a continuation of U.S. application Ser. No. 15/327,416, filed on Jan. 19, 2017, which is a National Stage application of PCT/US2015/041338, filed Jul. 21, 2015, which claims the benefit of U.S. Provisional Application No. 62/027,600, filed Jul. 22, 2014, all of which are incorporated by reference in their entirety herein.

BACKGROUND

The present disclosure generally relates to epoxides, methods for producing the epoxides, curable compositions including the epoxides, and articles and materials including the cured compositions.

Epoxy resins are high performance materials used in a wide variety of applications including protective coatings, adhesives, electronic laminates (such as those used in the fabrication of computer circuit boards), flooring and paving applications, glass fiber-reinforced pipes, and automotive parts (including leaf springs, pumps, and electrical components). In their cured form, epoxy resins offer desirable properties including good adhesion to other materials, excellent resistance to corrosion and chemicals, high tensile strength, and good electrical resistance. Challenges associated with the use of epoxy resins include the brittleness of the cured epoxy resins as a result of crosslinking Thus, there exists a need for epoxy-based materials with improved properties.

SUMMARY

In one aspect, disclosed is a compound having formula:

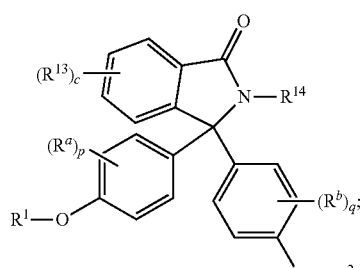
(I)

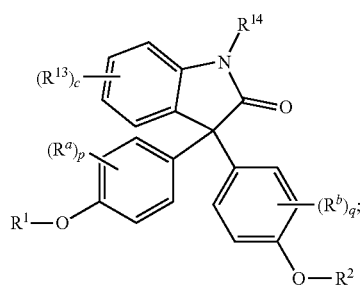
(II)

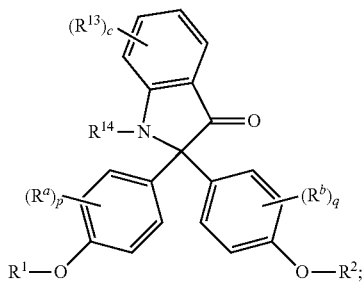
(III)

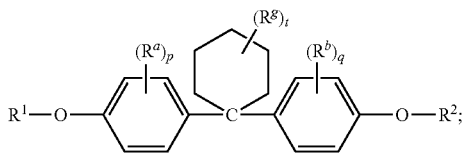
(IV)

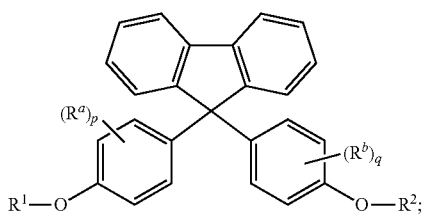
(V)

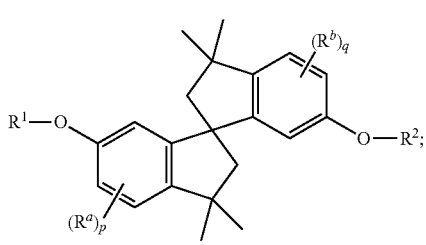
(VI)

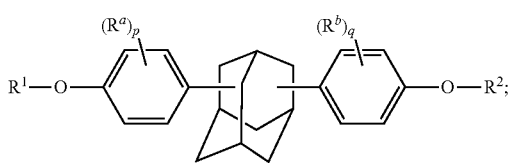
(VII)

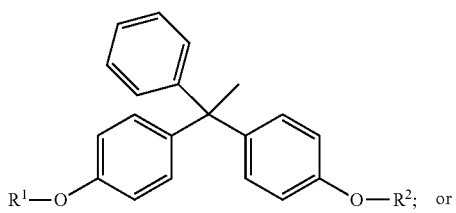
(VIII); or

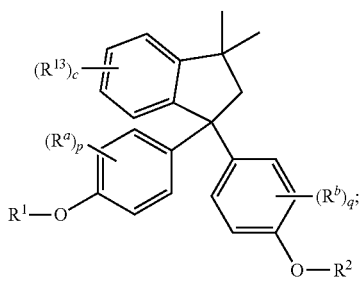
(IX)

wherein $R^1$ and $R^2$ at each occurrence are each independently selected from an epoxide-containing functional group; $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five, or six-membered cycloalkyl group; and t is 0 to 10.

In certain embodiments, $R^1$ and $R^2$ at each occurrence are each independently selected from an epoxide-containing group of formula:

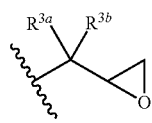

wherein $R^{3a}$ and $R^{3b}$ are each independently selected from hydrogen and $C_1$-$C_{12}$ alkyl.

In certain embodiments, $R^1$ and $R^2$ are each independently selected from:

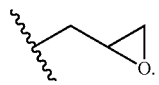

In certain embodiments, disclosed is a compound of formula:

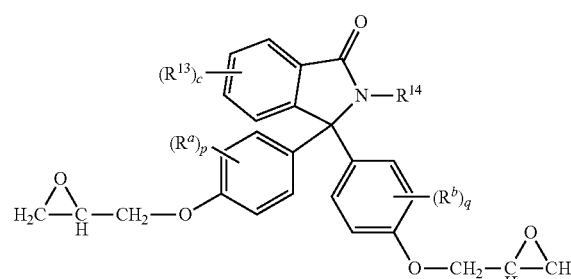

(1)

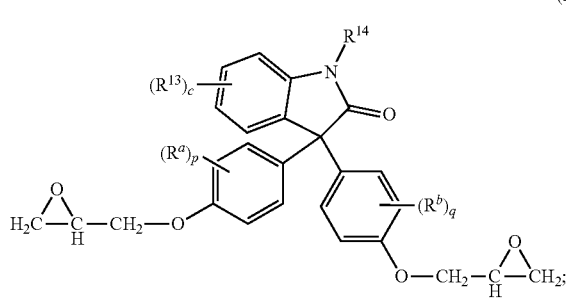

(2)

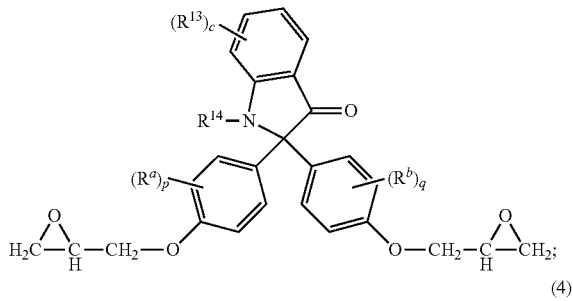

(3)

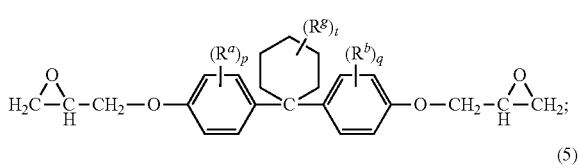

(4)

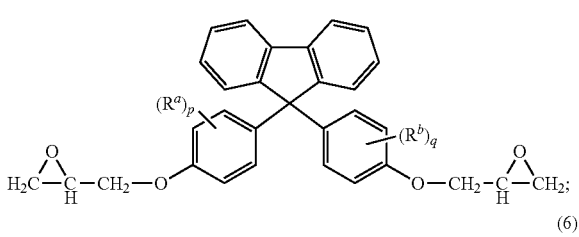

(5)

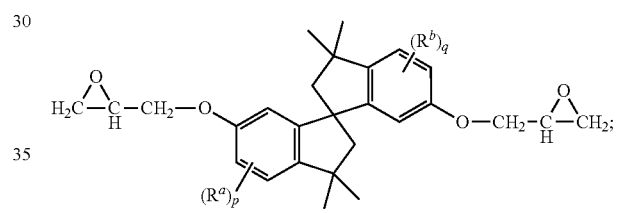

(6)

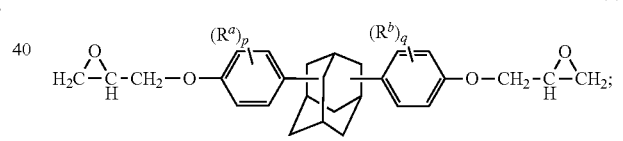

(7)

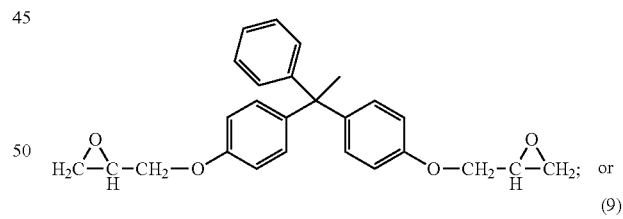

(8)

; or (9)

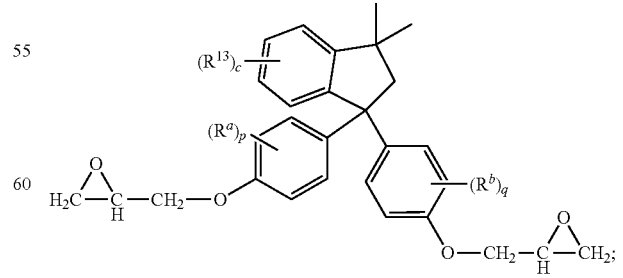

wherein $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five, or six-membered cycloalkyl group; and t is 0 to 10.

The epoxy can have a purity of 95% or greater, 97% or greater, 99% or greater as determined by high performance liquid chromatography (HPLC). The epoxy can be substantially free of oligomer impurities.

The viscosity of the epoxy resins can be inversely proportional with the purity of the resin. For example, a high purity diepoxide resin of formula (I) may have a lower viscosity compared to a lower purity diepoxide resin of formula (I).

The epoxy can have a melt/softening point of 85° C. or less, 80° C. or less, 75° C. or less, 70° C. or less, 65° C. or less, 60° C. or less, 55° C. or less, 50° C. or less, 45° C. or less, or 40° C. or less. The epoxy can have a melt/softening point of 85° C., 80° C., 75° C., 70° C., 65° C., 60° C., 55° C., 50° C., 45° C., or 40° C. The melting/softening point of the epoxy can be inversely proportional with the purity of the resin. For example, a high purity diepoxide resin of formula (I) may have a lower melt/softening point compared to a lower purity diepoxide resin of formula (I). Softening points can be determined according to ASTM E28-99, "Standard Test Methods for Softening Point of Resins Derived from Naval Stores by Ring-and-Ball Apparatus".

The epoxy can have formula (1-a), (2-a), or (4-b):

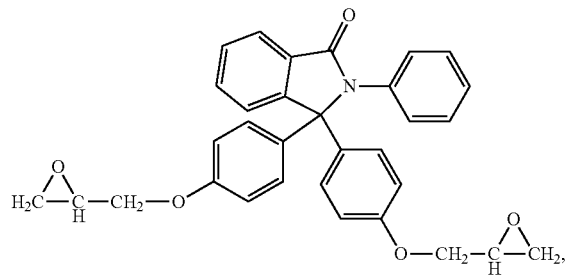

(1-a)

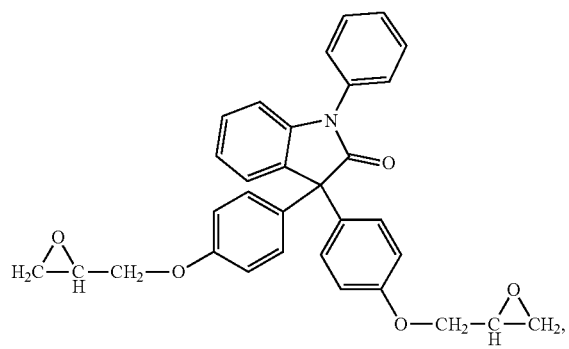

(2-a)

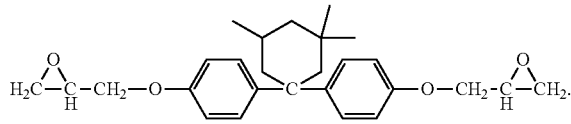

(4-b)

The epoxy can be derived from a compound of formula:

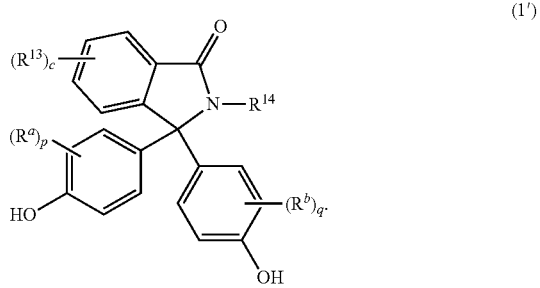

(1')

The epoxy can be derived from a compound of formula:

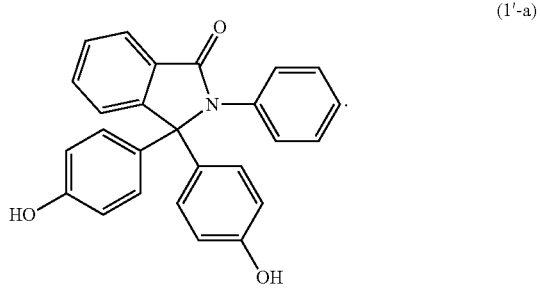

(1'-a)

The compound of formula (1'-a) can have less than 50 ppm of amino phenol impurities, less than 500 ppm of phenolphthalein, or 3 ppm or less of metal impurities, or a combination thereof.

In another aspect, disclosed is a process for preparing an epoxy of formula (1), comprising (a) providing a mixture of epichlorohydrin and a compound of formula (1'); (b) slowly adding a base to the mixture of (a) to provide a reaction mixture; and (c) stirring the reacting mixture for 8 to 12 hours at 20° C. to 24° C. The base can be sodium hydroxide or potassium hydroxide. The epoxy of formula (1) can have a purity of 99% or greater, as determined by high performance liquid chromatography (HPLC). The epoxy of formula (1) can have formula (1-a).

In another aspect, disclosed is a curable composition comprising: (i) at least one epoxy of formula (1)-(9); (ii) a curing promoter; and (iii) optionally an auxiliary epoxy resin different from the epoxy of (i).

The auxiliary epoxy resin can be selected from the group consisting of aliphatic epoxy resins, cycloaliphatic epoxy resins, bisphenol A epoxy resins, bisphenol-F epoxy resins, phenol novolac epoxy resins, cresol-novolac epoxy resins, biphenyl epoxy resins, polyfunctional epoxy resins, naphthalene epoxy resins, divinylbenzene dioxide, 2-glycidylphenylglycidyl ether, dicyclopentadiene-type epoxy resins, multi aromatic resin type epoxy resins, and mixtures thereof. The auxiliary epoxy resin can be a diglycidyl ether of 2,2-bis(4-hydroxyphenyl)propane.

The curing promoter can be an amine compound. The amine compound can be selected from isophoronediamine, triethylenetetraamine, diethylenetriamine, aminoethylpiperazine, 1,2- and 1,3-diaminopropane, 2,2-dimethylpropylenediamine, 1,4-diaminobutane, 1,6-diaminohexane, 1,7-diaminoheptane, 1,8-diaminooctane, 1,9-diaminononane, 1,12-diaminododecane, 4-azaheptamethylenediamine, N,N'-bis(3-aminopropyl)butane-1,4-diamine, cyclohexanediamine, dicyanamide, diamide diphenylmethane, diamide diphenylsulfonic acid (amine adduct), 4,4'-methylenedianiline, diethyltoluenediamine, m-phenylenediamine, p-phenylenediamine, melamine formaldehyde resins, urea formaldehyde resins, tetraethylenepentamine, 3-diethylaminopropylamine, 3,3'-iminobispropylamine, 2,4-bis(p-aminobenzyl)aniline, tetraethylenepentamine, 3-diethylaminopropylamine, 2,2,4- and 2,4,4-trimethylhexamethylenediamine, 1,2- and 1,3-diaminocyclohexane, 1,4-diamino-3,6-diethylcyclohexane, 1,2-diamino-4-ethylcyclohexane, 1,4-diamino-3,6-diethylcyclohexane, 1-cyclohexyl-3,4-diminocyclohexane, 4,4'-diaminondicyclohexylmethane, 4,4'-diaminodicyclohexylpropane, 2,2-bis(4-aminocyclohexyl)propane, 3,3'-dimethyl-4,4'-diaminodicyclohexylmethane, 3-amino-1-cyclohexaneaminopropane, 1,3- and 1,4-bis(aminomethyl)cyclohexane, m- and p-xylylenediamine, diethyl toluene diamines, and mixtures thereof. The amine compound can be a tertiary amine hardening accelerator. The tertiary amine hardening accelerator can be selected from triethylamine, tributylamine, dimethylaniline, diethylaniline, benzyldimethylamine (BDMA), α-methylbenzyldimethylamine, N,N-dimethylaminoethanol, N,N-dimethylaminocresol, and tri(N,N-dimethylaminomethyl)phenol. The amine compound can be an imidazole hardening accelerator selected from 2-methylimidazole, 2-ethylimidazole, 2-laurylimidazole, 2-heptadecylimidazole, 2-phenylimidazole, 4-methylimidazole, 4-ethylimidazole, 4-laurylimidazole, 4-heptadecylimidazole, 2-phenyl-4-methylimidazole, 2-phenyl-4-hydroxymethylimidazole, 2-ethyl-4-methylimidazole, 2-ethyl-4-hydroxymethylimidazole, 1-cyanoethyl-4-methylimidazole, 2-phenyl-4,5-dihydroxymethylimidazole, and mixtures thereof. The amine compound can be a cyclic amidine hardening accelerator selected from 4-diazabicyclo(2,2,2)octane (DABCO), diazabicycloundecene (DBU), 2-phenyl imidazoline, and mixtures thereof.

The curing promoter can be a phenolic hardener. The phenolic hardener can be selected from novolac type phenol resins, resole type phenol resins, aralkyl type phenol resins, dicyclopentadiene type phenol resins, terpene modified phenol resins, biphenyl type phenol resins, bisphenols, triphenylmethane type phenol resins, and mixtures thereof.

The curing promoter can be an anhydride hardener. The anhydride hardener can be selected from maleic anhydride (MA), phthalic anhydride (PA), hexahydro-o-phthalic anhydride (HEPA), tetrahydrophthalic anhydride (THPA), methyltetrahydrophthalic anhydride (MTHPA), methylhexahydrophthalic anhydride (MHHPA), nadic methyl anhydride (methyl himic anhydride, MHA), benzophenonetetracarboxylic diandydride (BTDA), tetrachlorophthalic anhydride (TCPA), pyromellitic dianhydride (PMDA), trimellitic anhydride (TMA), methyl-5-norbornene-2,3-dicarboxylic anhydride (MNA), hexahydrophthalic anhydride (1,2-cyclohexane dicarboxylic anhydride, (HHA)), and mixtures thereof.

The curing promoter can be selected from latent cationic cure catalysts, copper (II) salts of aliphatic or aromatic carboxylic acids, aluminum (III) salts of aliphatic or aromatic carboxylic acids, tin (II) salts of aliphatic or aromatic carboxylic acids, copper (II) β-diketonates, aluminum (III) β-diketonates, tin (IV) tetrachloride, boron trifluoride-trialkylamine complexes, and mixtures thereof. The curing promoter can be a latent cationic cure catalyst selected from diaryliodonium salts, phosphonic acid esters, sulfonic acid esters, carboxylic acid esters, phosphonic ylides, triarylsulfonium salts, benzylsulfonium salts, aryldiazonium salts, benzylpyridinium salts, benzylammonium salts, isoxazolium salts, and combinations thereof.

The curing promoter can be a latent cationic cure catalyst comprising a diaryliodonium salt having the structure $[(R^{10})(R^{11})I]^+ X^-$, wherein $R^{10}$ and $R^{11}$ are each independently a $C_6$-$C_{14}$ monovalent aromatic hydrocarbon radical, optionally substituted with from 1 to 4 monovalent radicals selected from $C_1$-$C_{20}$ alkyl, $C_1$-$C_{20}$ alkoxy, nitro, and chloro; and wherein $X^-$ is an anion. The curing promoter can having the structure $[(R^{10})(R^{11})I]^+ SbF_6^-$, wherein $R^{10}$ and $R^{11}$ are each independently a $C_6$-$C_{14}$ monovalent aromatic hydrocarbon radical, optionally substituted with from 1 to 4 monovalent radicals selected from $C_1$-$C_{20}$ alkyl, $C_1$-$C_{20}$ alkoxy, nitro, and chloro.

The curing promoter can be a latent cationic cure catalyst comprising 4-octyloxyphenyl phenyl iodonium hexafluoroantimonate. The curing promoter can be a copper (II) or aluminum (III) salt of an aliphatic or aromatic carboxylic acid selected from copper (II), tin (II), and aluminum (III) salts of acetate, stearate, gluconate, citrate, benzoate, and mixtures thereof. The curing promoter can be a copper (II) or aluminum (III) β-diketonate selected from copper (II) and aluminum (III) salts of acetylacetonate. The curing promoter can be a boron trifluoride-trialkylamine complex.

In another aspect, disclosed is a cured composition comprising the product obtained by curing the curable composition. The cured composition can exhibit a single Tg, such as a single Tg of greater than or equal to 200° C., greater than or equal to 225° C., or greater than or equal to 250° C.

In another aspect, disclosed is an article comprising the cured composition. The article can be selected from electrical components, computer components, printed circuit boards, and automotive, aircraft, and watercraft exterior and interior components. The article can be produced by a resin transfer molding process.

In another aspect, disclosed is a material comprising the cured composition. The material can be a coating, an adhesive, a composite, an encapsulant, a sealant, or a combination thereof. The composite can be a glass fiber based composite, a carbon fiber based composite, or a combination thereof. The material can be produced by a resin transfer molding process.

The compounds, compositions, methods, and processes are further described herein.

DETAILED DESCRIPTION

Figure 1:
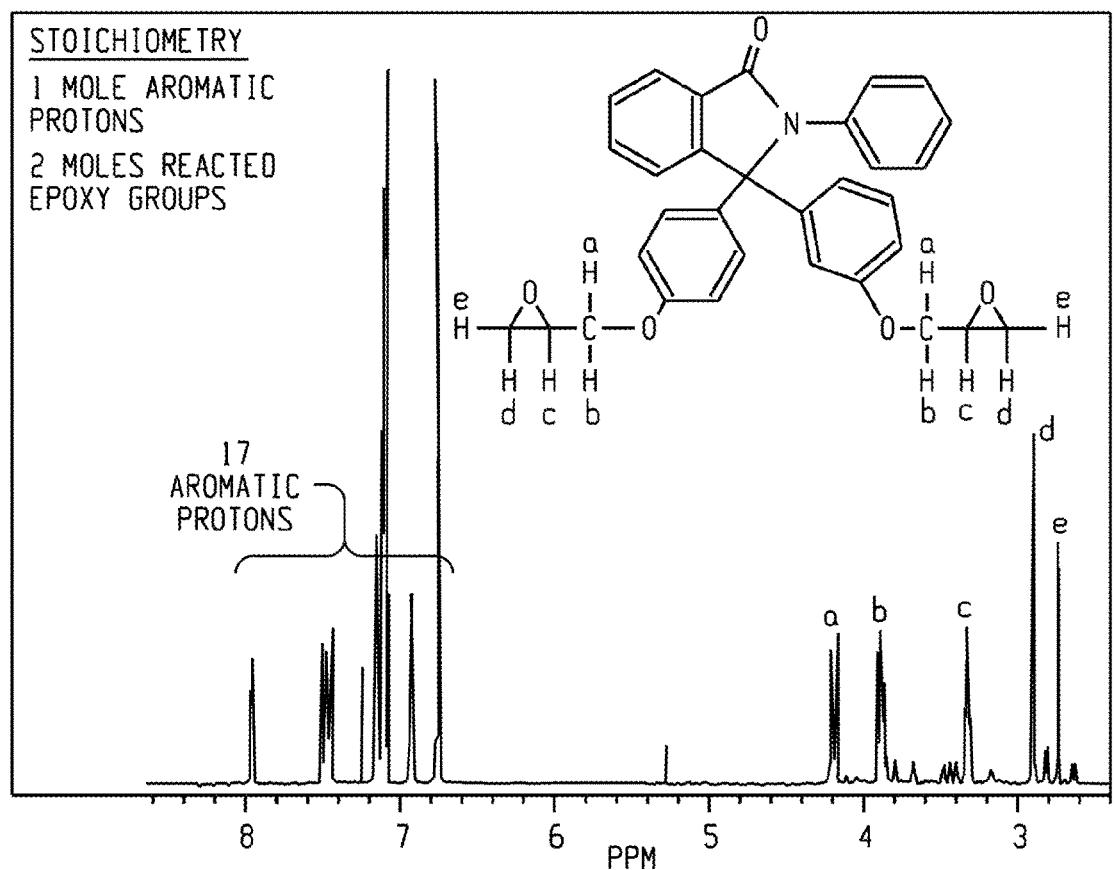
FIG. 1 depicts proton NMR analysis (400 MHz) of an exemplary epoxide compound. The NMR shows no indication of any secondary alcohol group (~4.4 ppm) from oligomerization.

The present disclosure relates to high heat, high purity compounds (e.g., diepoxides), methods for preparing the compounds, and curable compositions including the compounds. The disclosure also relates to materials and articles derived from the compounds and curable compositions. The disclosed compounds can be used to produce composites with good thermal and mechanical performance (e.g., high glass transition temperatures (Tg) and ductility), and may be particularly suited for transportation and aerospace applications. The compounds may be high heat, high purity epoxide compounds.

Thermal performance of thermosets (e.g., epoxy thermosets) has previously been accomplished by increasing the crosslink density of the composite network via multi-functional resins having, for example, three or four epoxy groups per molecule. Curing these multi-functional resins (e.g., with aromatic amine) results in a thermoset matrix with a very high crosslink density. The highly crosslinked nature of the matrix can, however, lead to an inherent brittleness. The disclosed compounds, by comparison, can provide a thermoset matrix with suitable heat resistance and ductility, without the high crosslink density that leads to brittleness. As such, the disclosed compounds may be employed to formulate epoxy resins with high Tg while maintaining or increasing the toughness of the resin. To achieve such a resin the crosslink density may be lowered by the use of a more rigid difunctional epoxy instead of tri- and/or tetrafunctional epoxy resins.

The disclosed resins may also provide the advantage of having low viscosities. The low viscosity resins can be used for production of parts via resin transfer molding processes. For example, the resins can be used to obtain a short fill time into a mold containing a glass preform without moving the glass preform. The mold may be isothermal and once the resin enters into the mold it may heat up and start to cure, with a concomitant increase in viscosity. The low viscosity resins can also be used for production of electronic moldings to encapsulate microchips, for example.

The low viscosity of the resins may be at least partially attributed to the high purity of the resins. For example, the disclosed epoxy resins may be substantially free of oligomeric impurities, as well as other impurities, such as phenolphthalein, metals, and other materials. Bisphenol A diglycidyl epoxy resins, by comparison, may contain oligomeric materials that can have a pronounced effect on viscosity. For example, in the synthesis of epoxy resins from bisphenols and epichlorohydrin, a 2:1 adduct can be formed along with higher order adducts (e.g., a 3:2 adduct) depending on stoichiometry and reaction conditions.

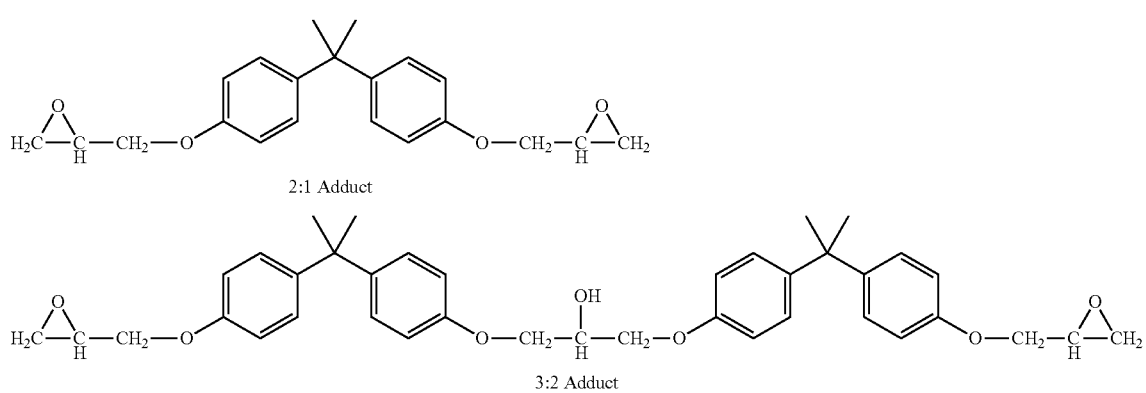

The effect of higher molecular weight adducts on viscosity appears in Table 1. When the purity goes from ~100 to 95% the viscosity increases over 50%. The disclosed epoxides and methods can provide high purity epoxide compositions that are substantially lacking in the oligomeric impurities, and as such, can provide lower viscosity materials.

TABLE 1

Effect of purity on viscosity*

| Epoxy resin grade | Purity, wt % 2:1 adduct | Viscosity @ 25° C., cPs |
| --- | --- | --- |
| DER 332 | ~100 | 5780 |
| DER 330 | 95 | 8760 |
| Epon 828 | 89 | 13250 |
| DER 317 | 83 | 20500 |

*Viscosity was measured using a Brookfield spindle viscometer; DER 332, 330, and 317 epoxy resins were from Dow Chemical; Epon 828 was from Momentive.

As another advantage, the disclosed resins, such as PPPBP-di-epoxy, may be solid at room temperature, making them useful as electronic molding compounds for chip encapsulation and for making prepregs (pre-impregnated cloth), as solvent is used.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

"Acrylatealkyl" as used herein may mean an acrylate appended to the parent molecular moiety through an alkyl, as defined herein. The acrylate may be substituted or unsubstituted. Representative examples of acrylatealkyl include, but are not limited to, $H_2C=CH_2-C(O)O-CH_2-$ and $H_2C=CH(CH_3)-C(O)O-CH_2-$.

"Alkenylalkyl" as used herein may mean an alkene appended to the parent molecular moiety through an alkyl, as defined herein.

"Alkyl" as used herein may mean a linear, branched, or cyclic hydrocarbyl group, such as a methyl group, ethyl group, n-propyl group, isopropyl group, n-butyl group, isobutyl group, tert-butyl group, n-pentyl group, isopentyl group, n-hexyl group, isohexyl group, cyclopentyl group, cyclohexyl group, and the like.

"Alkynylalkyl" as used herein may mean an alkyne appended to the parent molecular moiety through an alkyl, as defined herein.

"Aryl" as used herein may mean a substituted or unsubstituted aryl radical containing from 6 to 36 ring carbon atoms. Examples of aryl include, but are not limited to, a phenyl group, a bicyclic hydrocarbon fused ring system, or a tricyclic hydrocarbon fused ring system wherein one or more of the rings are a phenyl group.

"Arylalkyl" as used herein may mean an aryl, as defined herein, appended to the parent molecular moiety through an alkyl, as defined herein.

"Copolymer" as used herein may mean a polymer derived from two or more structural unit or monomeric species, as opposed to a homopolymer, which is derived from only one structural unit or monomer.

"$C_3$-$C_6$ cycloalkyl" as used herein may mean cyclopropyl, cyclobutyl, cyclopentyl, or cyclohexyl.

"Glass Transition Temperature" or "Tg" as used herein may mean the maximum temperature that a polymer or material will have one or more useful properties. These properties include impact resistance, stiffness, strength, and shape retention. The Tg may be measured using a differential scanning calorimetry method and expressed in degrees Celsius.

"Halo" as used herein may be a substituent to which the prefix is attached is substituted with one or more independently selected halogen radicals. For example, "$C_1$-$C_6$ haloalkyl" means a $C_1$-$C_6$ alkyl substituent wherein one or more hydrogen atoms are replaced with independently selected halogen radicals. Non-limiting examples of $C_1$-$C_6$ haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

"Halogen" or "halogen atom" as used herein may mean a fluorine, chlorine, and bromine or iodine atom.

"Heteroaryl" as used herein may mean any aromatic heterocyclic ring which may comprise an optionally benzo-condensed 5 or 6 membered heterocycle with from 1 to 3 heteroatoms selected among N, O or S. Non limiting examples of heteroaryl groups may include pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazotyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, and the like.

"Hindered phenol stabilizer" as used herein may mean 3,5-di-tert-butyl-4-hydroxyhydrocinnamic acid, octadecyl ester.

"Hydrocarbyl" as used herein refers to a monovalent moiety formed by removing a hydrogen atom from a hydrocarbon. Representative hydrocarbyls are alkyl groups having 1 to 25 carbon atoms, such as, for example, methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6 to 25 carbon atoms, such as ring-substituted and ring-unsubstituted forms of phenyl, tolyl, xylyl, naphthyl, biphenyl, tetraphenyl, and the like; arylalkyl groups having 7 to 25 carbon atoms, such as ring-substituted and ring-unsubstituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like.

"Hydroxyalkyl" refers to an alkyl group, as defined herein, substituted by at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

"PETS release agent" as used herein may mean pentaerythritol tetrastearate, mold release.

"Phosphite stabilizer" as used herein may mean tris-(2,4-di-tert-butylphenyl) phosphite.

"Straight or branched $C_1$-$C_3$ alkyl" or "straight or branched $C_1$-$C_3$ alkoxy" as used herein may mean methyl, ethyl, n-propyl, isopropyl, methoxy, ethoxy, n-propoxy and isopropoxy.

Unless otherwise indicated, each of the foregoing groups may be unsubstituted or substituted, provided that the substitution does not significantly adversely affect synthesis, stability, or use of the compound.

The terms "structural unit" and "monomer" are interchangeable as used herein.

"Thermal stability" as used herein refers to resistance of a polymer to molecular weight degradation under thermal conditions. Thus, a polymer with poor thermal stability may show significant molecular weight degradation under thermal conditions, such as during extrusion, molding, thermoforming, hot-pressing, and like conditions. Molecular weight degradation may also be manifest through color formation and/or in the degradation of other properties such as weatherability, gloss, mechanical properties, and/or thermal properties. Molecular weight degradation can also cause significant variation in processing conditions such as melt viscosity changes.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Disclosed are compounds (also referred to herein as monomers) useful for preparation of thermoset compositions. The monomers can be used to impart heat resistance to materials and articles derived from compositions comprising the monomers.

The compounds (e.g., diepoxides) can have a purity of greater than or equal to 90%, greater than or equal to 91%, greater than or equal to 92%, greater than or equal to 93%, greater than or equal to 94%, greater than or equal to 95%, greater than or equal to 96%, greater than or equal to 97%, greater than or equal to 98%, greater than or equal to 99%, greater than or equal to 99.1%, greater than or equal to 99.2%, greater than or equal to 99.3%, greater than or equal to 99.4%, greater than or equal to 99.5%, greater than or equal to 99.6%, greater than or equal to 99.7%, greater than or equal to 99.8%, or greater than or equal to 99.9%, as determined by high performance liquid chromatography (HPLC).

The compounds can have a metal impurity content of 3 ppm or less, 2 ppm or less, 1 ppm or less, 500 ppb or less, 400 ppb or less, 300 ppb or less, 200 ppb or less, or 100 ppb or less. The metal impurities may be iron, calcium, zinc, aluminum, or a combination thereof. The compounds can have an unknown impurities content of 0.1 wt % or less. The compounds can have a color APHA value of 40 or less, 35 or less, 30 or less, 25 or less, 20 or less, 19 or less, 18 or less, 17 or less, 16 or less, or 15 or less, as measured using test method ASTM D1209.

The disclosed compounds can have formula (I)-(IX):

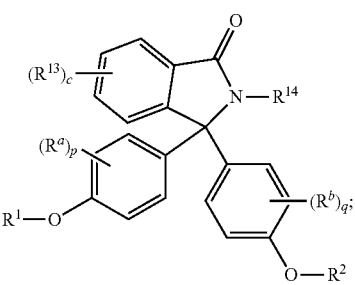

(I)

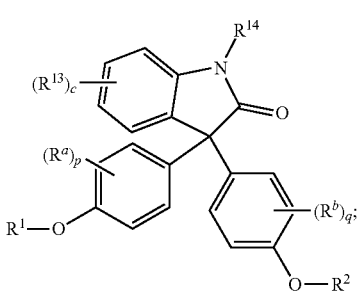

(II)

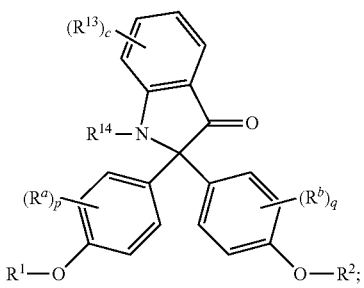

(III)

-continued

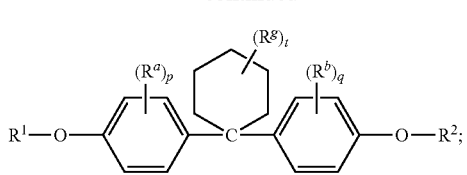
(IV)

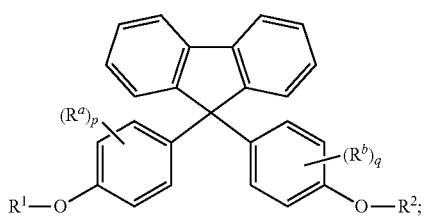
(V)

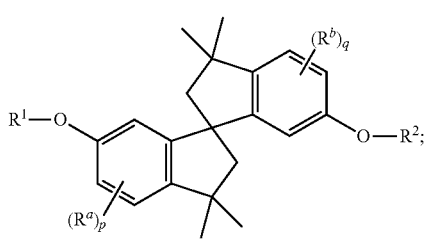
(VI)

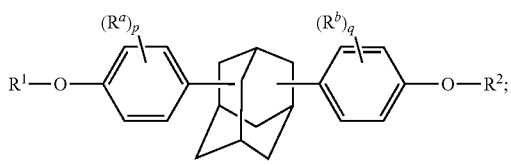
(VII)

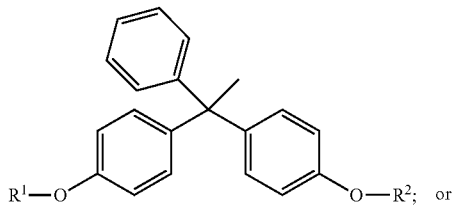
(VIII)

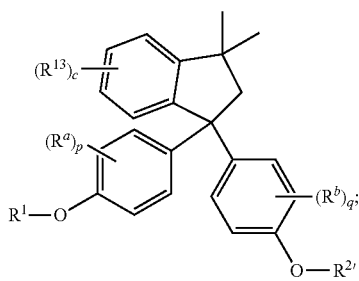
(IX)

wherein $R^1$ and $R^2$ at each occurrence are each independently selected from an epoxide-containing functional group; $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five, or six-membered cycloalkyl group; and t is 0 to 10.

In certain embodiments, $R^1$ and $R^2$ at each occurrence are each independently selected from:

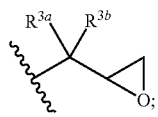

wherein $R^{3a}$ and $R^{3b}$ are each independently selected from hydrogen and $C_1$-$C_{12}$ alkyl.

In certain embodiments, $R^1$ and $R^2$ are each independently selected from:

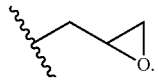

In certain embodiments, the disclosed compounds are diepoxides. The epoxides may be substantially free of epoxide oligomer impurities. The epoxides may have an oligomer impurity content of less than or equal to 3%, less than or equal to 2%, less than or equal to 1%, less than or equal to 0.5%, less than or equal to 0.4%, less than or equal to 0.3%, less than or equal to 0.2%, or less than or equal to 0.1%, as determined by high performance liquid chromatography. The epoxides can have an epoxy equivalent weight corresponding to purity of the bisepoxide of 95% purity or greater, 96% purity or greater, 97% purity or greater, 98% purity or greater, 99% purity or greater, or 100% purity. Epoxy equivalent weight (EEW) is the weight of resin in grams that contains one mole of epoxy groups. It is also the molecular weight of the resin divided by the number of epoxy groups in one molecule of resin.

The epoxides can have formula (1)-(9), or a combination thereof,

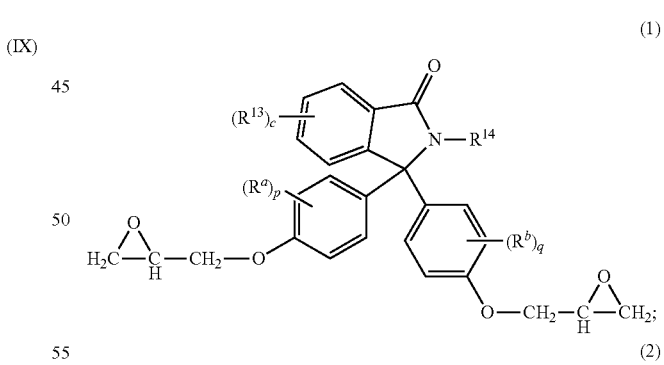
(1)

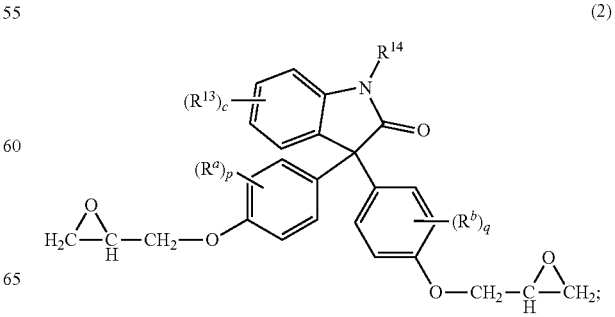
(2)

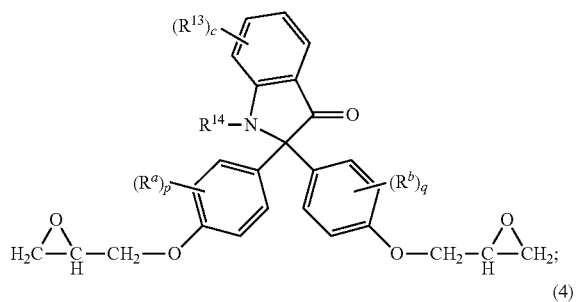
(3)

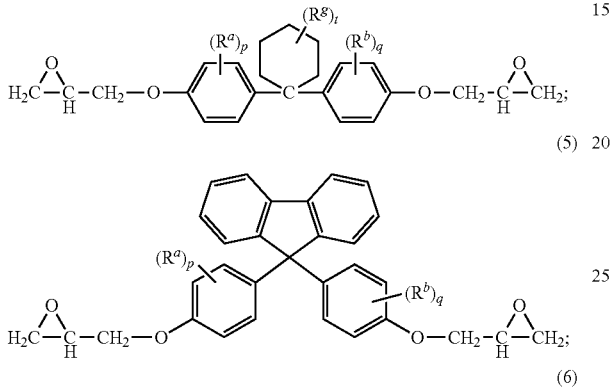
(4)

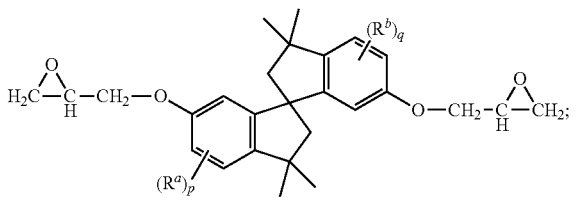
(5)

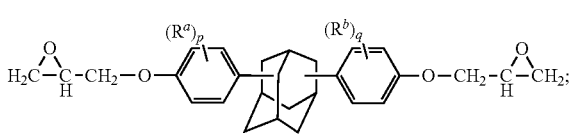
(6)

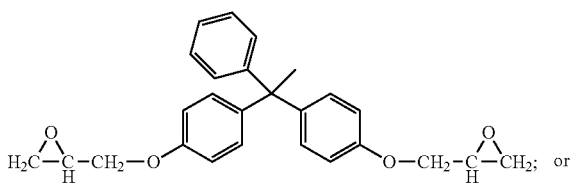
(7)

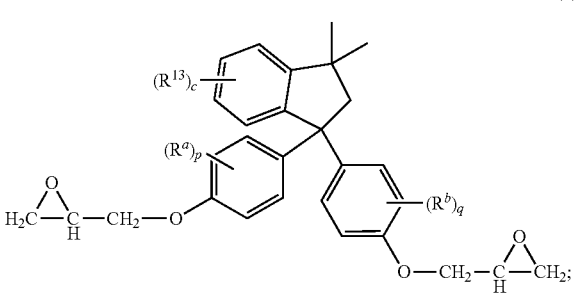
(8)

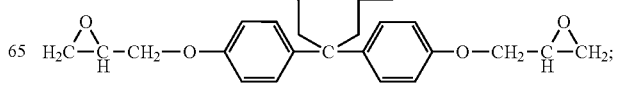 or
(9)

wherein $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five, or six-membered cycloalkyl group; and t is 0 to 10.

The epoxides can have formula (1-a), (2-a), (3-a), (4-a), (4-b), (4-c), (5-a), (6-a), (7-a), (8-a), (9-a), or a combination thereof,

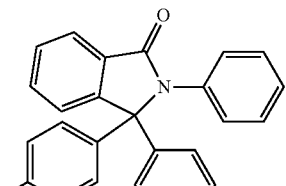
(1-a)

(2-a)

(3-a)

(4-a)

(4-b)

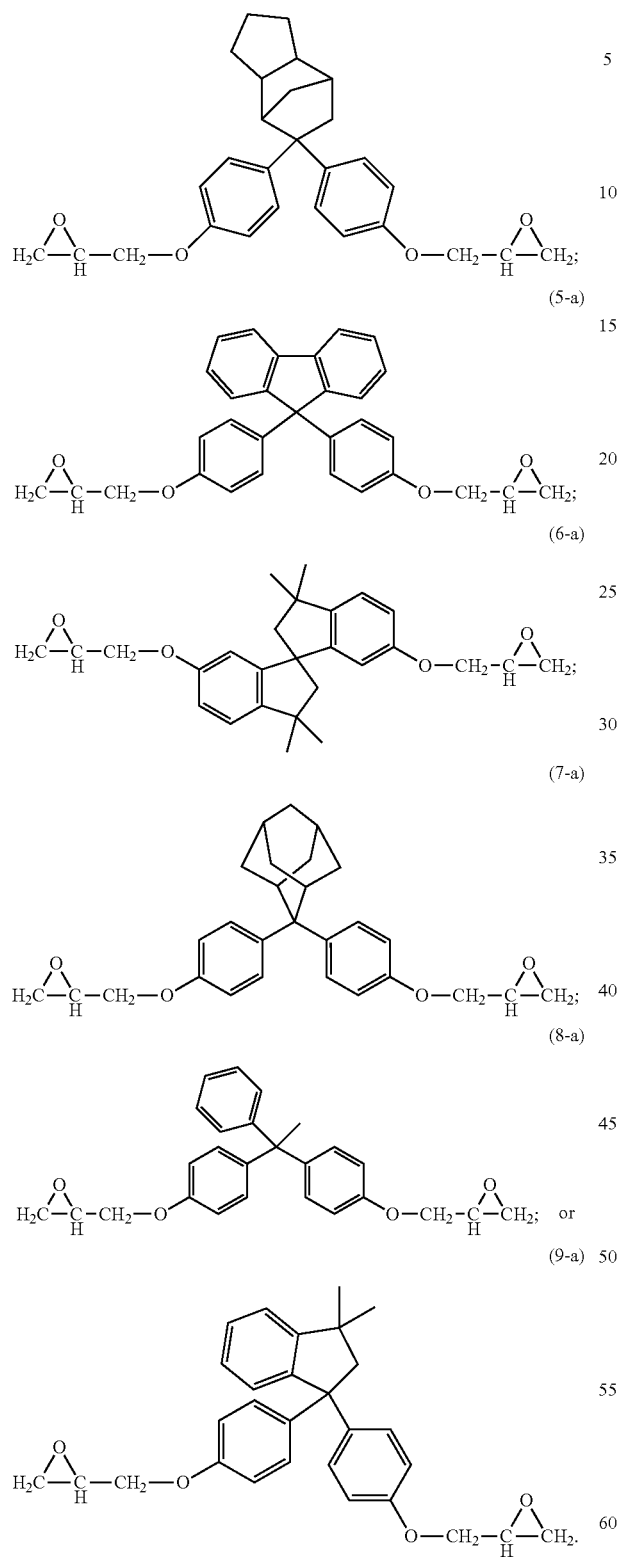

The epoxides of formula (1-a), (2-a), and (3-a), for example, can have an epoxy equivalent weight of 263 g/mol, 262 g/mol, 261 g/mol, 260 g/mol, 259 g/mol, 258 g/mol, 257 g/mol, 256 g/mol, 255 g/mol, 254 g/mol, 253 g/mol, or 252 g/mol. The epoxides of formula (1-a), (2-a), and (3-a), for example, can have an epoxy equivalent weight of 252.5 g/mol.

The epoxides may be derived from a corresponding bisphenol. The epoxides may be derived from a bisphenol of formula (1')-(9'), or a combination thereof,

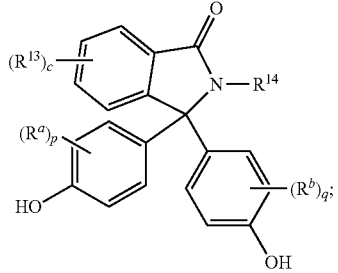

(1')

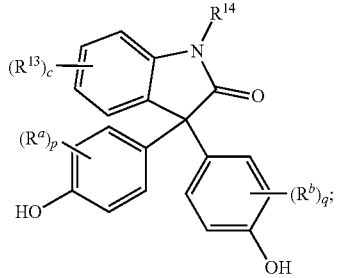

(2')

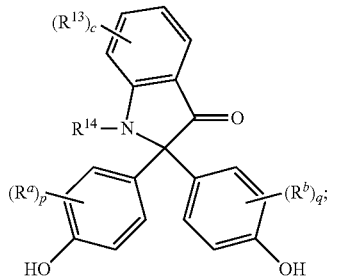

(3')

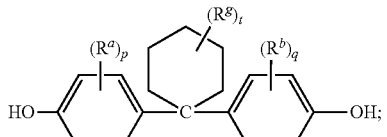

(4')

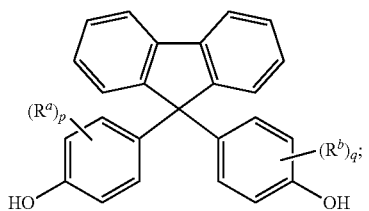

(5')

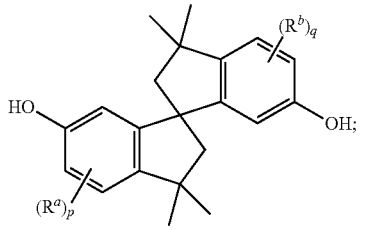

(6')

(7')

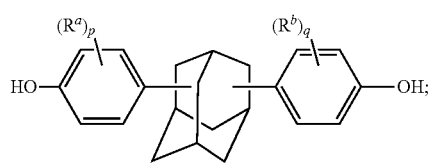

(8')

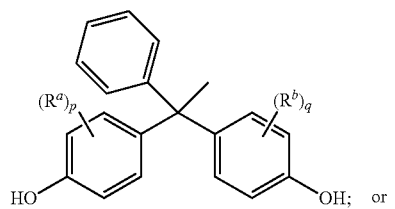
or (9')

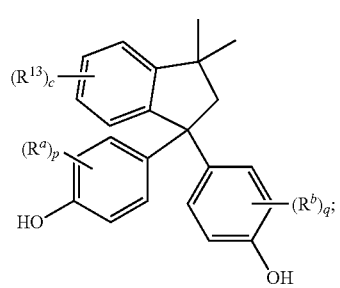

wherein $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five, or six-membered cycloalkyl group; and t is 0 to 10.

The epoxides may be derived from a bisphenol of formula (1'-a), (2'-a), (3'-a), (4'-a), (4'-b), (4'-c), (5'-a), (6'-a), (7'-a), (8'-a), (9'-a), or a combination thereof, (1'-a)

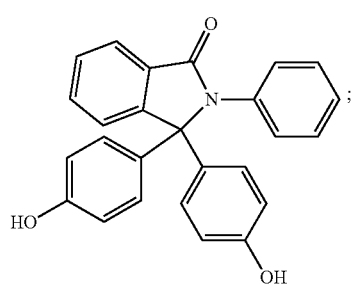

(2'-a)

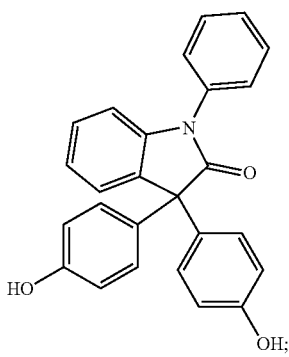

(3'-a)

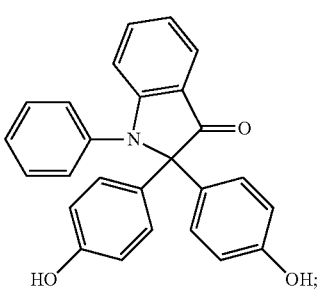

(4'-a)

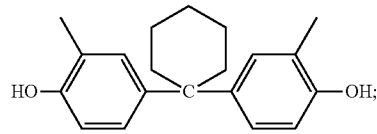

(4'-b)

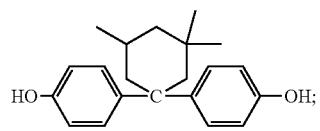

(4'-c)

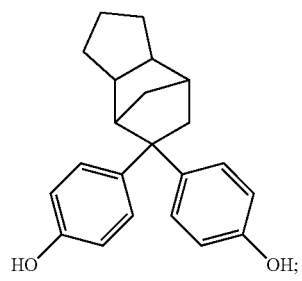

(5'-a)

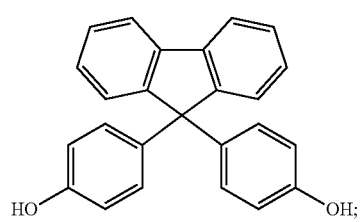

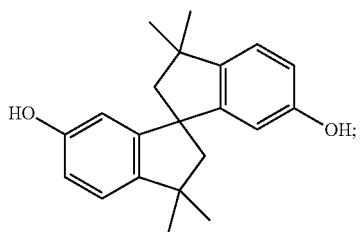
(6'-a)

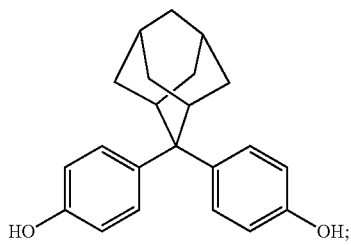
(7'-a)

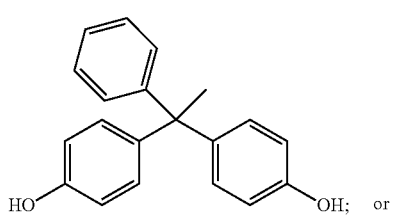
(8'-a) or

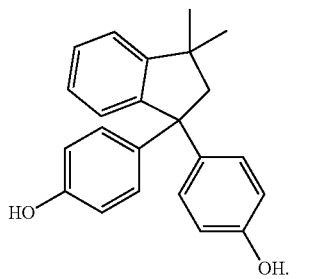
(9'-a)

The bisphenols may have a purity of 97% or greater, 98% or greater, 99% or greater, 99.5% or greater, 99.8% or greater, 99.90% or greater, or 99.95% or greater. The bisphenols can have an aminophenol impurity content of 200 ppm or less, 150 ppm or less, 100 ppm or less, 90 ppm or less, 80 ppm or less, 70 ppm or less, 60 ppm or less, 50 ppm or less, 40 ppm or less, 30 ppm or less, 20 ppm or less, or 10 ppm or less. The amino phenol impurity may be 2-phenyl-3-(4-aminophenyl)-3-(4-hydroxyphenyl)phthalimidine. The bisphenols can have a phenolphthalein impurity content of 1,000 ppm or less, 750 ppm or less, 500 ppm or less, 400 ppm or less, 300 ppm or less, 200 ppm or less, 100 ppm or less, 50 ppm or less. The bisphenols can have a metal impurity content of 3 ppm or less, 2 ppm or less, 1 ppm or less, 500 ppb or less, 400 ppb or less, 300 ppb or less, 200 ppb or less, or 100 ppb or less. The metal impurities may be iron, calcium, zinc, aluminum, or a combination thereof. The bisphenols can have an unknown impurities content of 0.1 wt % or less. The bisphenols can have a color APHA value of 40 or less, 35 or less, 30 or less, 25 or less, 20 or less, 19 or less, 18 or less, 17 or less, 16 or less, or 15 or less, as measured using test method ASTM D1209.

The disclosed epoxides of formula (1)-(9) can be prepared from a corresponding bisphenol compound [e.g., a bisphenol of formula (1')-(9')]. The bisphenol can be provided in a mixture with an epoxide source, such as epichlorohydrin. The resultant mixture can be treated with a catalytic amount of base at a selected temperature. Suitable bases include, but are not limited to, carbonates (e.g., sodium bicarbonate, ammonium carbonate, or dissolved carbon dioxide), and hydroxide bases (e.g., sodium hydroxide, potassium hydroxide, or ammonium hydroxide). The base may be added as a powder (e.g., powdered sodium hydroxide). The base may be added slowly (e.g., over a time period of 60 to 90 minutes). The temperature of the reaction mixture may be maintained at 20° C. to 24° C., for example. The reaction may be stirred for a selected time period (e.g., 5 hours to 24 hours, or 8 hours to 12 hours). The reaction may be quenched by addition of an aqueous solvent, optionally along with one or more organic solvents (e.g., ethyl acetate). The aqueous layer can be extracted (e.g., with ethyl acetate), and the organic extract can be dried and concentrated. The crude product can be purified (e.g., by silica gel chromatography) and isolated. The isolated product may be obtained in a yield of 80% or greater, 85% or greater, or 90% or greater.

The purity of the isolated product may be greater than or equal to 90%, greater than or equal to 91%, greater than or equal to 92%, greater than or equal to 93%, greater than or equal to 94%, greater than or equal to 95%, greater than or equal to 96%, greater than or equal to 97%, greater than or equal to 98%, greater than or equal to 99%, greater than or equal to 99.1%, greater than or equal to 99.2%, greater than or equal to 99.3%, greater than or equal to 99.4%, greater than or equal to 99.5%, greater than or equal to 99.6%, greater than or equal to 99.7%, greater than or equal to 99.8%, or greater than or equal to 99.9%, as determined by high performance liquid chromatography (HPLC). The isolated product may be substantially free of oligomeric impurities.

Also disclosed are curable compositions including the disclosed high heat, high purity epoxides. The epoxides can blended with one or more additional components to provide curable compositions. For example, the curable compositions can further include curing promoters, auxiliary epoxy resins, flame retardants, fillers, reinforcing fibers, dyes, pigments, colorants, antioxidants, heat stabilizers, light stabilizers, plasticizers, lubricants, flow modifiers, drip retardants, antiblocking agents, antistatic agents, flow-promoting agents, processing aids, substrate adhesion agents, mold release agents, toughening agents, low-profile additives, stress-relief additives, and combinations thereof.

The curable compositions can include the disclosed high heat, high purity epoxides in an amount of 1 wt % to 99.9 wt %, 3 wt % to 50 wt %, 5 wt % to 40 wt %, or 10 wt % to 30 wt %, based on total weight of the curable composition.

The curable compositions, when cured, may have a Tg of greater than or equal to 145° C., greater than or equal to 150° C., greater than or equal to 155° C., greater than or equal to 160° C., greater than or equal to 165° C., greater than or equal to 170° C., greater than or equal to 175° C., greater than or equal to 180° C., greater than or equal to 185° C., greater than or equal to 190° C., greater than or equal to 200° C., greater than or equal to 210° C., greater than or equal to 220° C., greater than or equal to 230° C., greater than or equal to 240° C., greater than or equal to 250° C., greater than or equal to 260° C., greater than or equal to 270° C., greater than or equal to 280° C., greater than or equal to 290° C., or greater than or equal to 300° C., as measured using a differential scanning calorimetry method. In any of the foregoing embodiments, the Tg cn bel less than 450° C., or less than 420° C. Differential scanning calorimetry (DSC) can be conducted with a heating rate of 10° C./minute or 20° C./minute. The cured composition can exhibit a single Tg, as opposed to two or more Tgs, indicating that the epoxy is covalently bound to the epoxy resin matrix of the cured composition. In other words, the epoxy may not exist as a separate phase within the epoxy resin matrix. Depending on the type and relative amounts of epoxy components and curing promoters, the glass transition may range from 100° C. to 300° C., or 150° C. to 200° C., for example.

The cured compositions can exhibit good impact strength. In some embodiments, the cured composition exhibits an unnotched Izod impact strength of at least 400 joules per meter, specifically 400 to 600 joules per meter, more specifically 450 to 550 joules per meter, and still more specifically 480 to 520 joules per meter, as measured at 23° C. with a hammer energy of 2 foot-pounds in accordance with ASTM D 4812-06.

The cured compositions can exhibit good ductility. The cured compositions can exhibit good fracture toughness, unnotched Izod impact strength, and good tensile elongation.

The cured compositions can exhibit increased char formation on pyrolysis.

The cured compositions can exhibit low moisture absorption.

The cured compositions can exhibit decreased shrinkage upon curing.

The cured compositions can exhibit decreased dielectric properties.

The cured compositions can exhibit a dielectric constant of 2.8 to 3.2, specifically 2.9 to 3.1, and more specifically, 3.00 to 3.06, as measured at 1,000 megahertz in accordance with IPC-TM-650 2.5.5.9.

The cured compositions can exhibit a loss tangent of 0.011 to 0.017, specifically 0.012 to 0.016, and more specifically 0.013 to 0.015, as measured at 1,000 megahertz in accordance with IPC-TM-650 2.5.5.9.

The cured compositions can exhibit a water absorption of less than or equal to 5 weight percent (wt %), specifically less than or equal to 4 wt %, more specifically less than or equal to 3 wt %, and still more specifically less than or equal to 2 wt %, measured after immersion in deionized water at 80° C. for 250 hours.

The cured composition may preferably exhibit a coefficient of thermal expansion (CTE) below its Tg of not greater than 30 micrometer/meter-° C. (μm/m-° C.), preferably not greater than 25 μm/m-° C., more preferably not greater than 20 μm/m-° C.

The cured compositions can exhibit a number of additional advantageous properties simultaneously.

The curable composition can include a curing promoter. The term "curing promoter" as used herein encompasses compounds whose roles in curing epoxy resins are variously described as those of a hardener, a hardening accelerator, a curing catalyst, and a curing co-catalyst, among others. Hardeners are coreactive curing agents. Hardeners react with the epoxy groups and/or the secondary hydroxyl groups of the epoxy resin. Suitable hardeners for epoxy resins are known in the art and include, for example, amines, dicyandiamide, polyamides, amidoamines, Mannich bases, anhydrides, phenol-formaldehyde resins, carboxylic acid functional polyesters, polysulfides, polymercaptans, isocyanates, cyanate esters, and combinations thereof.

In some embodiments, the curing promoter comprises an amine. The amine can be a polyamine, a tertiary amine, an amidine, and combinations thereof. Examples of suitable polyamines include amine hardeners such as isophoronediamine, triethylenetetraamine, diethylenetriamine, aminoethylpiperazine, 1,2- and 1,3-diaminopropane, 2,2-dimethylpropylenediamine, 1,4-diaminobutane, 1,6-diaminohexane, 1,7-diaminoheptane, 1,8-diaminooctane, 1,9-diaminononane, 1,12-diaminododecane, 4-azaheptamethylenediamine, N,N'-bis(3-aminopropyl)butane-1,4-diamine, cyclohexanediamine, 4,4'-methylenedianiline, diethyltoluenediamine, m-phenylenediamine, p-phenylenediamine, tetraethylenepentamine, 3-diethylaminopropylamine, 3,3'-iminobispropylamine, 2,4-bis(p-aminobenzyl)aniline, tetraethylenepentamine, 3-diethylaminopropylamine, 2,2,4- and 2,4,4-trimethylhexamethylenediamine, 1,2- and 1,3-diaminocyclohexane, 1,4-diamino-3,6-diethylcyclohexane, 1,2-diamino-4-ethylcyclohexane, 1,4-diamino-3,6-diethylcyclohexane, 1-cyclohexyl-3,4-diaminocyclohexane, 4,4'-diaminondicyclohexylmethane, 4,4'-diaminodicyclohexylpropane, 2,2-bis(4-aminocyclohexyl)propane, 3,3'-dimethyl-4,4'-diaminodicyclohexylmethane, 3-amino-1-cyclohexaneaminopropane, 1,3- and 1,4-bis(aminomethyl)cyclohexane, m- and p-xylylenediamine, diethyl toluene diamines, and combinations thereof. In some embodiments, the curing promoter comprises a hardener selected from the group consisting of m-phenylenediamine, 4,4'-diaminodiphenylmethane, and combinations thereof.

Examples of suitable amine compounds further include tertiary amine hardening accelerators such as triethylamine, tributylamine, dimethylaniline, diethylaniline, benzyldimethylamine (BDMA) α-methylbenzyldimethylamine, N,N-dimethylaminoethanol, N,N-dimethylaminocresol, tri(N,N-dimethylaminomethyl)phenol, and combinations thereof. Examples of suitable amine compounds further include imidazole hardening accelerators such as 2-methylimidazole, 2-ethylimidazole, 2-laurylimidazole, 2-heptadecylimidazole, 2-phenylimidazole, 4-methylimidazole, 4-ethylimidazole, 4-laurylimidazole, 4-heptadecylimidazole, 2-phenyl-4-methylimidazole, 2-phenyl-4-hydroxymethylimidazole, 2-ethyl-4-methylimidazole, 2-ethyl-4-hydroxymethylimidazole, 1-cyanoethyl-4-methylimidazole, 2-phenyl-4,5-dihydroxymethylimidazole, and combinations thereof. Examples of suitable amine compounds further include cyclic amidine hardening accelerators such as 4-diazabicyclo(2,2,2)octane (DABCO), diazabicycloundecene (DBU), 2-phenyl imidazoline, and combinations thereof.

The curing promoter can comprise other amine compounds. Examples of other suitable amine compounds include hardeners such as ketimines, which are the reaction products of ketones and primary aliphatic amines; polyetheramines, which are the reaction products of polyols derived from ethylene oxide or propylene oxide with amines; amine-terminated polyamides, prepared by the reaction of dimerized and trimerized vegetable oil fatty acids with polyamines; amidoamines, imidazolines, and combinations thereof, for example the reaction product of diethylene triamine and tall-oil fatty acid. Suitable amine hardeners include aliphatic amine compounds, such as diethylene triamine (DETA), triethylene tetramine (TETA), tetraethylene pentamine (TEPA), diethylaminopropylamine (DEAPA), methylene diamine, N-aminoethylpyrazine (AEP), m-xylylene diamine (MXDA) and the like; aromatic amine compounds such as m-phenylene diamine (MPDA), 4,4'-diaminodiphenylmethane (MDA), diaminodiphenylsulfone (DADPS), diaminodiphenylether and the like; and secondary or tertiary amine compounds such as phenylmethyldimethylamine (BDMA), dimethylaminomethylphenol (DMP-10), tris(dimethylaminomethyl)phenol (DMP-30), piperidine, 4,4'-diaminodicyclohexylmethane, 1,4-diaminocyclohexane, 2,6-diaminopyridine, mphenylenediamine, p-phenylenediamine, 4,4'-diaminodiphenylmethane, 2,2'-bis(4-aminophenyl)propane, benzidine, 4,4'-diaminophenyl oxide, 4,4'-diaminodiphenylsulfone, bis(4-aminophenyl)phenylphosphine oxide, bis(4-aminophenyl) methylamine, 1,5-diaminonaphthalene, m-xylenediamine, p-xylenediamine, hexamethylenediamime, 6,6'-diamine-2, 2'-pyridyl, 4,4'-diaminobenzophenone, 4,4'-diaminoazobenzene, bis(4-aminophenyl)phenylmethane, 1,1-bis(4-aminophenyl)cyclohexane, 1,1-bis(4-amino-3-methylphenyl) cyclohexane, 2,5-bis(aminophenyl)-1,3,4-oxadiazole, 2,5-bis(p-aminophenyl)-1,3,4-oxadiazole, 2,5-bis(aminophenyl) thiazo(4,5-d)thiazole, 5,5'-di(m-aminophenyl)-(2,2)-bis-(1, 3,4-oxadiazolyl), 4,4'-diaminodiphenylether, 4,4'-bis(p-aminophenyl)-2,2'-dithiazole, m-bis(4-p-aminophenyl-2-thiazolyl)benzene, 4,4'-diaminobenzanilide, 4,4'-diaminophenyl benzoate, N,N'-bis(4-aminobenzyl)-p-phenylenediamine, and 4,4'-methylenebis(2-chloroaniline); melamine, 2-amino-s-triazine, 2-amino-4-phenyl-s-triazine, 2-amino-4-phenyl-s-triazine, 2-amino-4,6-diethyl-s-triazine, 2-amino-4,6-diphenyl-s-triazine, 2-amino-4,6-bis(p-methoxyphenyl)-s-triazine, 2-amino-4-anilino-s-triazine, 2-amino-4-phenoxy-s-triazine, 2-amino-4-chloro-s-triazine, 2-amino-4-aminomethyl-6-chloro-s-triazine, 2-(p-aminophenyl)-4,6-dichloro-s-triazine, 2,4-diamino-s-triazine, 2,4-diamino-6-methyl-s-triazine, 2,4-diamino-6-phenyl-s-triazine, 2,4-diamino-6-benzyl-s-triazine, 2,4-diamino-6-(p-aminophenyl)-s-triazine, 2,4-diamino-6-(m-aminophenyl)-s-triazine, 4-amino-6-phenyl-s-triazine-2-ol, and 6-amino-s-triazine-2,4-diol, and the like, and mixtures thereof.

Further amine hardeners include isophoronediamine, triethylenetetraamine, diethylenetriamine, aminoethylpiperazine, 1,2- and 1,3-diaminopropane, 2,2-dimethyl propylenediamine, 1,4-diaminobutane, 1,6-diaminohexane, 1,7-diaminoheptane, 1,8-diaminooctane, 1,9-diaminononane, 1,12-diaminododecane, 4-azaheptamethylene diamine, N,N'-bis(3-aminopropyl) butane-1,4-diamine, cyclohexanediamine, dicyandiamine, diamide diphenylmethane, diamide diphenylsulfonic acid (amine adduct), 4,4'-methylenedianiline, diethyltoluenediamine, m-phenylene diamine, melamine formaldehyde, tetraethylenepentamine, 3-diethylaminopropylamine, 3,3'-iminobispropylamine, 2, 4-bis(p-aminobenzyl)aniline, tetraethylenepentamine, 3-diethylaminopropylamine, 2,2,4- and 2,4,4-trimethylhexamethylenediamine, 1,2- and 1,3-diaminocyclohexane, 1,4-diamino-3,6-diethylcyclohexane, 1,2-diamino-4-ethylcyclohexane, 1,4-diamino-3,6-diethylcyclohexane, 1-cyclohexyl-3,4-diamino-cyclohexane, 4,4'-diaminondicyclohexylmethane, 4,4'-diaminodicyclohexylpropane, 2,2-bis(4-aminocyclohexyl) propane, 3,3'-dimethyl-4,4'-diaminodicyclohexylmethane, 3-amino-1-cyclohexaneaminopropane, 1,3- and 1,4-bis (aminomethyl)cyclohexane, m- and p-xylylenediamine, and mixtures thereof.

Further exemplary hardeners include 1-benzyl-2-methylimidazole, 4,4'-diaminodiphenyl-methane, 2-methylimidazole, 2-ethyl-4-methylimidazole (manufactured and sold by Wako Pure Chemical Industries, Ltd., Japan), 2-ethyl-4-methylimidazoline, 2-ethyl-4-methylimidazole low viscosity, 2-benzyl-4-methylimidazole, 2-benzyl-4-methylimidazoline, 2-ethylimidazole, 2-phenylimidazole, 2-phenyl-4,5-dihydroxymethyimidazole, 1-(2-cyanoethyl)-2-ethyl-4-methylimidazole, 1-(2-cyanoethyl)-2-phenyl-4,5-di(cyanoethoxymethyl) imidazole, and 1-cyanoethyl-2-methylimidazole.

The curing promoter can comprise an anhydride hardener. Examples of suitable anhydrides include maleic anhydride (MA), phthalic anhydride (PA), hexahydro-o-phthalic anhydride (HEPA), tetrahydrophthalic anhydride (THPA), methyltetrahydrophthalic anhydride (MTHPA), methylhexahydrophthalic anhydride (MHHPA), nadic methyl anhydride (methyl-5-norbornene-2,3-dicarboxylic anhydride methyl himic anhydride, MHA), benzophenonetetracarboxylic dianydride (BTDA), tetrachlorophthalic anhydride (TCPA), pyromellitic dianhydride (PMDA), trimellitic anhydride (TMA), hexahydrophthalic anhydride (1,2-cyclohexane dicarboxylic anhydride, (HHA)), and combinations thereof.

The curing promoter can comprise a phenol-formaldehyde resin. Suitable phenol-formaldehyde resins include, for example, novolac type phenol resins, resole type phenol resins, aralkyl type phenol resins, dicyclopentadiene type phenol resins, terpene modified phenol resins, biphenyl type phenol resins, bisphenol type phenol resins, triphenylmethane type phenol resins, and combinations thereof.

The curing promoter can comprise a Mannich base. Examples of Mannich bases are the reaction products of an amine with phenol and formaldehyde, melamine-formaldehyde resins, urea-formaldehyde resins, and combinations thereof.

In addition to the tertiary amines listed above, the curing promoter can comprise other hardening accelerators. Suitable examples of other hardening accelerators are substituted ureas, for example 3-phenyl-1,1-dimethyl urea; the reaction product of phenyl isocyanate with dimethylamine; the reaction product of toluene diisocyanate with dimethylamine; quaternary phosphonium salts, such as tetraalkyl and alklytriphenyl phosphonium halide; and combinations thereof.

The curing promoter can comprise a metal salt, for example a copper (II) or aluminum (III) salt of an aliphatic or aromatic carboxylic acid. Suitable examples of such salts include the copper (II), tin (II), and aluminum (III) salts of acetate, stearate, gluconate, citrate, benzoate, and like anions, as well as combinations thereof. The curing promoter can comprise a copper (II) or aluminum (III) β-diketonate. Suitable examples of such metal diketonates include the copper (II) and aluminum (III) salts of acetylacetonate. The curing promoter can comprise a boron trifluoride-trialkylamine complex. An illustrative boron trifluoride-trialkylamine complex is boron trifluoride-trimethylamine complex.

The curing promoter can comprise a latent cationic cure catalyst. Latent cationic cure catalysts are used, for example, in UV-cured epoxy resin compositions. Latent cationic cure catalysts include, for example, diaryliodonium salts, phosphonic acid esters, sulfonic acid esters, carboxylic acid esters, phosphonic ylides, triarylsulfonium salts, benzylsulfonium salts, aryldiazonium salts, benzylpyridinium salts, benzylammonium salts, isoxazolium salts, and combinations thereof. For example, the curing promoter can be a latent cationic cure catalyst comprising a diaryliodonium salt having the structure $[(R^{10})(R^{11})I]^+X^-$ wherein $R^{10}$ and $R^{11}$ are each independently a $C_6$-$C_{14}$ monovalent aromatic hydrocarbon radical, optionally substituted with from 1 to 4 monovalent radicals selected from $C_1$-$C_{20}$ alkyl, $C_1$-$C_{20}$ alkoxy, nitro, and chloro; and wherein $X^-$ is an anion.

In some embodiments, the curing promoter is a latent cationic cure catalyst comprising a diaryliodonium salt having the structure $[(R^{10})(R^{11})I]^+$ $SbF_6^-$ wherein $R^{10}$ and $R^{11}$ are each independently a $C_6$-$C_{14}$ monovalent aromatic hydrocarbon radical, optionally substituted with from 1 to 4 monovalent radicals selected from $C_1$-$C_{20}$ alkyl, $C_1$-$C_{20}$ alkoxy, nitro, and chloro. In some embodiments, the curing promoter is a latent cationic cure catalyst comprising 4-octyloxyphenyl phenyl iodonium hexafluoroantimonate.

The amount of curing promoter will depend on the type of curing promoter, as well as the identities and amounts of the other components of the curable composition. For example, when the curing promoter is a latent cationic cure catalyst, it can be used in an amount of 0.1 to 10 parts by weight per 100 parts by weight total of the disclosed epoxide and the auxiliary epoxy resin (if present). As another example, when the curing promoter is a copper (II) or aluminum (III) beta-diketonate, it can be used in an amount of 1 to 10 parts by weight per 100 parts by weight of the disclosed epoxide and the auxiliary epoxy resin (if present). As yet another example, when the curing promoter is an amine hardener, it can be used in an amount of 2 to 40 parts by weight, per 100 parts by weight of the disclosed epoxide and the auxiliary epoxy resin (if present). As yet another example, when the curing promoter is an imidazole hardening accelerator, it can be used in an amount of 0.01 to 5 parts by weight, per 100 parts by weight of the disclosed epoxide and the auxiliary epoxy resin (if present).

In some embodiments, the curing promoter comprises a hardener, and the curable composition comprises the curing promoter in an amount of 0.1 to 50 wt %, specifically 0.5 to 30 wt %, more specifically 1 to 20 wt %, and still more specifically, 2 to 10 wt %, based on the weight of the curable composition.

Suitable soft and hard acid base complexes as curing promoters include acid-base complexes such as boron trifluoride-trialkylamine complex, and the like. An illustrative boron trifluoride-trialkylamine complex is boron trifluoride-trimethylamine complex.

When the curing promoter comprises a hardener, its amount can be specified in terms of equivalents relative to total epoxy equivalents. For example, when the curing promoter comprises an amine hardener, the disclosed epoxide, the curing promoter, and auxiliary epoxy resin provide a ratio of total epoxy equivalents to total amine equivalents of 1:1 to 1.3:1, specifically 1.1:1 to 1.2:1, and still more specifically 1.1:1 to 1.2:1.

The curable composition can include an auxiliary epoxy resin. The auxiliary epoxy resin can have formula:

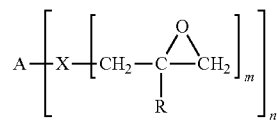

wherein A is an organic or inorganic radical of valence n, X is oxygen or nitrogen, m is 1 or 2 and consistent with the valence of X, R is hydrogen or methyl, n is 1 to 1000, specifically 1 to 8, more specifically 2 or 3 or 4.

Suitable classes of epoxy resins include, for example, aliphatic epoxy resins, cycloaliphatic epoxy resins, bisphenol A epoxy resins, bisphenol-F epoxy resins, bisphenol-S type epoxy resin, phenol novolac epoxy resins, cresol-novolac epoxy resins, biphenyl epoxy resins, isocyanurate type epoxy resin, hydantoin type epoxy resin, cycloaliphatic epoxy resin, polyfunctional epoxy resins, naphthalene epoxy resins, divinylbenzene dioxide, 2-glycidylphenyl-glycidyl ether, dicyclopentadiene-type epoxy resins, multi aromatic resin type epoxy resins, and the like, and combinations thereof.

Other suitable classes of epoxy resins may include, for example, halogenated hydantoin type epoxy resin, biphenyl type epoxy resins, triphenylmethane type epoxy resin, tetra phenyl-glycidyl-ether ethane (4 functionality epoxy resin), various kinds of novolak type epoxy resin, etc.

Suitable epoxies include those having the following structures:

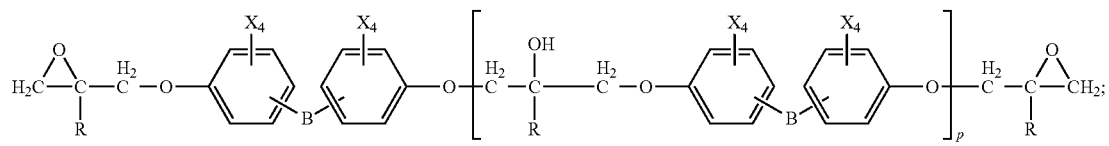

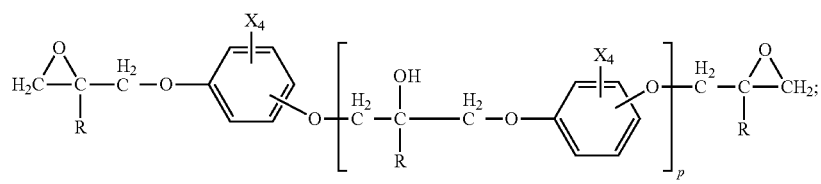

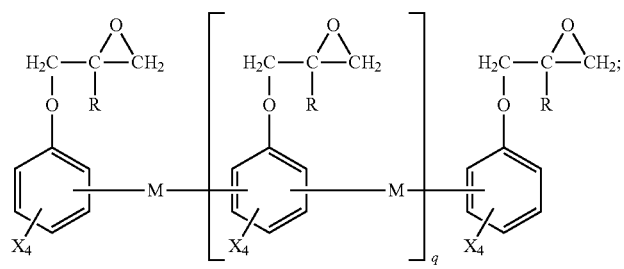

-continued

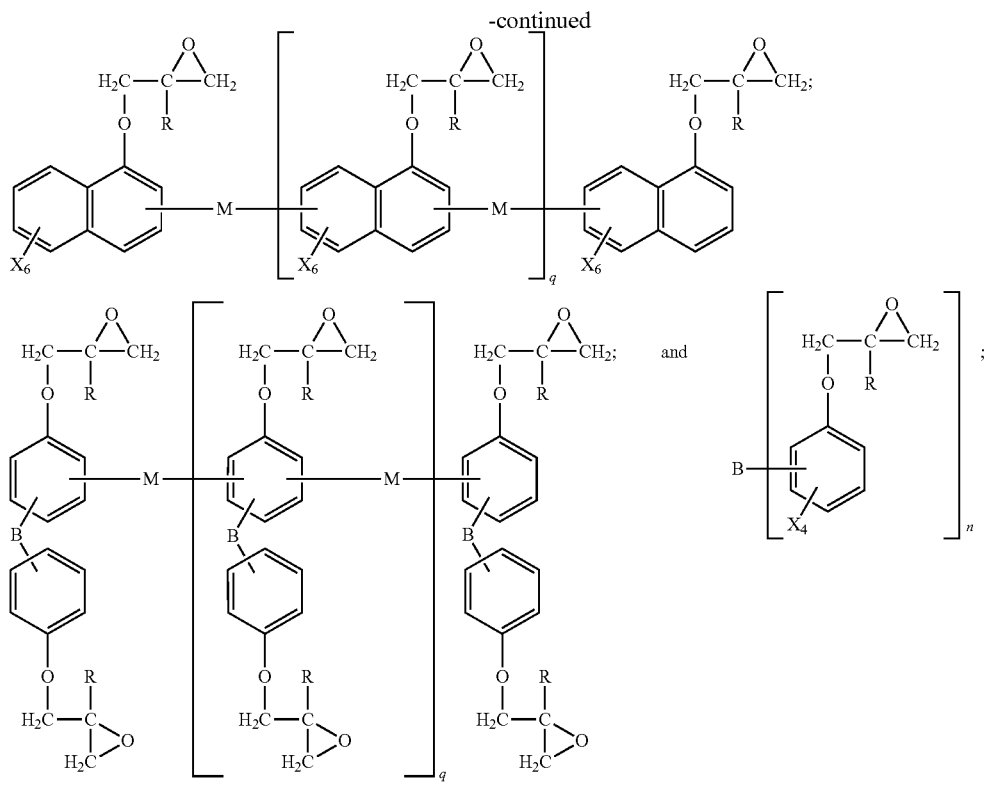

wherein each occurrence of R is independently hydrogen or methyl; each occurrence of M is independently C1-C18 hydrocarbylene optionally further comprising a member or members selected from oxirane, carboxy, carboxamide, ketone, aldehyde, alcohol, halogen, nitrile; each occurrence of X is independently hydrogen, chloro, fluoro, bromo, C1-C18 hydrocarbyl optionally further comprising a member or members selected from carboxy, carboxamide, ketone, aldehyde, alcohol, halogen, and nitrile; each occurrence of B is independently a carbon-carbon single bond, C1-C18 hydrocarbyl, C1-C12 hydrocarbyloxy, C1-C12 hydrocarbylthio, carbonyl, sulfide, sulfonyl, sulfinyl, phosphoryl, silane, or such groups further comprising a member or members selected from carboxyalkyl, carboxamide, ketone, aldehyde, alcohol, halogen, and nitrile; n is 1 to 20; and each occurrence of p and q is independently 0 to 20.

Suitable epoxy resins for many applications include those produced by the reaction of epichlorohydrin or epibromohydrin with a phenolic compound. Suitable phenolic compounds include resorcinol, catechol, hydroquinone, 2,6-dihydroxynaphthalene, 2,7-dihydroxynapthalene, 2-(diphenylphosphoryl)hydroquinone, bis(2,6-dimethylphenol)2,2'-biphenol, 4,4-biphenol, 2,2',6,6'-tetramethylbiphenol, 2,2',3,3',6,6'-hexamethylbiphenol, 3,3',5,5'-tetrabromo-2,2'6,6'-tetramethylbiphenol, 3,3'-dibromo-2,2',6,6'-tetramethylbiphenol, 2,2',6,6'-tetramethyl-3,3'5-dibromobiphenol, 4,4'-isopropylidenediphenol (bisphenol A), 4,4'-isopropylidenebis(2,6-dibromophenol) (tetrabromobisphenol A), 4,4'-isopropylidenebis(2,6-dimethylphenol) (teramethylbisphenol A), 4,4'-isopropylidenebis(2-methylphenol), 4,4'-isopropylidenebis(2-allylphenol), 4,4'-(1,3-phenylenediisopropylidene)bisphenol (bisphenol M), 4,4'-isopropylidenebis(3-phenylphenol), 4,4'-(1,4-phenylenediisoproylidene)bisphenol (bisphenol P), 4,4'-ethylidenediphenol (bisphenol E), 4,4'-oxydiphenol, 4,4'-thiodiphenol, 4,4'-thiobis(2,6-dimethylphenol), 4,4'-sulfonyldiphenol, 4,4'-sulfonylbis(2,6-dimethylphenol) 4,4'-sulfinyldiphenol, 4,4'-hexafluoroisoproylidene)bisphenol (Bisphenol AF), 4,4'-(1-phenylethylidene)bisphenol (Bisphenol AP), bis(4-hydroxyphenyl)-2,2-dichloroethylene (Bisphenol C), bis(4-hydroxyphenyl)methane (Bisphenol-F), bis(2,6-dimethyl-4-hydroxyphenyl)methane, 4,4'-(cyclopentylidene)diphenol, 4,4'-(cyclohexylidene)diphenol (Bisphenol Z), 4,4'-(cyclododecylidene)diphenol 4,4'-(bicyclo [2.2.1]heptylidene)diphenol, 4,4'-(9H-fluorene-9,9-diyl) diphenol, 3,3-bis(4-hydroxyphenyl)isobenzofuran-1(3H)-one, 1-(4-hydroxyphenyl)-3,3-dimethyl-2,3-dihydro-1H-inden-5-ol, 1-(4-hydroxy-3,5-dimethylphenyl)-1,3,3,4,6-pentamethyl-2,3-dihydro-1H-inden-5-ol, 3,3,3',3'-tetramethyl-2,2',3,3'-tetrahydro-1,1'-spirobi[indene]-5,6'-diol (spirobiindane), dihydroxybenzophenone (bisphenol K), tris(4-hydroxyphenyl)methane, tris(4-hydroxyphenyl) ethane, tris(4-hydroxyphenyl)propane, tris(4-hydroxyphenyl)butane, tris(3-methyl-4-hydroxyphenyl)methane, tris(3, 5-dimethyl-4-hydroxyphenyl)methane, tetrakis(4-hydroxyphenyl)ethane, tetrakis(3,5-dimethyl-4-hydroxyphenyl)ethane, bis(4-hydroxyphenyl) phenylphosphine oxide, dicyclopentadienylbis(2,6-dimethyl phenol), dicyclopentadienyl bis(2-methylphenol), dicyclopentadienyl bisphenol, and the like and mixtures thereof. In some examples, the epoxy resin comprises a bisphenol A diglycidylether epoxy resin.

Other suitable epoxy resins include N-glycidyl phthalimide, N-glycidyltetrahydrophthalimide, phenyl glycidyl ether, p-butylphenyl glycidyl ether, styrene oxide, neohexene oxide, ethylene glycol diglycidyl ether, polyethylene glycol diglycidyl ether, propylene glycol diglycidyl ether, polypropylene glycol diglycidyl ether, tetramethyleneglycol diglycidyl ether, polytetramethylene glycol diglycidyl ether, resorcinol-type epoxy compounds, phenol novolac-type epoxy compounds, ortho-cresol novolac-type epoxy compounds, adipic acid diglycidyl ester, sebacic acid diglycidyl ester, and phthalic acid diglycidyl ester.

Other epoxy resins include the glycidyl ethers of phenolic resins such as the glycidyl ethers of phenol-formaldehyde novolac, alkyl substituted phenol-formaldehyde resins including cresol-formaldehyde novolac, t-butylphenol-formaldehyde novolac, sec-butylphenol-formaldehyde novolac, tert-octylphenol-formaldehyde novolac, cumylphenol-formaldehyde novolac, decylphenol-formaldehyde novolac. Other useful epoxies are the glycidyl ethers of bromophenol-formaldehyde novolac, chlorophenolformaldehyde novolac, phenol-bis(hydroxymethyl)benzene novolac, phenol-bis(hydroxymethylbiphenyl) novolac, phenol-hydroxybenzaldehyde novolac, phenol-dicylcopentadiene novolac, naphthol-formaldehyde novolac, naphthol-bis(hydroxymethyl)benzene novolac, naphthol-bis(hydroxymethylbiphenyl) novolac, naphthol-hydroxybenzaldehyde novolac, and naphthol-dicylcopentadiene novolacs, and the like, and mixtures thereof.

Other suitable epoxy resins include the polyglycidyl ethers of polyhydric aliphatic alcohols. Examples of such polyhydric alcohols include 1,4-butanediol, 1,6-hexanediol, polyalkylene glycols, glycerol, trimethylolpropane, 2,2-bis(4-hydroxycyclohexyl)propane, and pentaerythritol.

Further suitable epoxy resins are polyglycidyl esters which are obtained by reacting epichlorohydrin or similar epoxy compounds with an aliphatic, cycloaliphatic, or aromatic polycarboxylic acid, such as oxalic acid, adipic acid, glutaric acid, phthalic, isophthalic, terephthalic, tetrahydrophthalic or hexahydrophthalic acid, 2,6-naphthalenedicarboxylic acid, and dimerized fatty acids. Examples are diglycidyl terephthalate and diglycidyl hexahydrophthalate. Moreover, polyepoxide compounds which contain the epoxide groups in random distribution over the molecule chain and which can be prepared by emulsion copolymerization using olefinically unsaturated compounds that contain these epoxide groups, such as, for example, glycidyl esters of acrylic or methacrylic acid, can be used.

Examples of further epoxy resins that can be used are those based on heterocyclic ring systems, for example hydantoin epoxy resins, triglycidyl isocyanurate and its oligomers, triglycidyl-p-aminophenol, triglycidyl-p-aminodiphenyl ether, tetraglycidyldiaminodiphenylmethane, tetraglycidyldiaminodiphenyl ether, tetrakis(4-glycidyloxyphenyl)ethane, urazole epoxides, uracil epoxides, and oxazolidinone-modified epoxy resins.

Other examples are polyepoxides based on aromatic amines, such as aniline, for example N,N-diglycidylaniline, diaminodiphenylmethane and N,N-dimethylaminodiphenylmethane or N,N-dimethylaminodiphenyl sulfone and cycloaliphatic epoxy resins such as 3,4-epoxycyclohexylmethyl-3,4-epoxycyclohexane carboxylate, 4,4'-(1,2-epoxyethyl)biphenyl, 4,4'-di(1,2-epoxyethyl)diphenyl ether, and bis(2,3-epoxycyclopentyl)ether.

Examples of mono-functional epoxy include 2-ethylhexyl glycidyl ether, butyl glycidyl ether, phenyl glycidyl ether, t-butyl glycidyl ether, o-cresyl glycidyl ether, and nonyl phenol glycidyl ether.

Oxazolidinone-modified epoxy resins can also be used, such as those disclosed in *Angew. Makromol. Chem.*, vol. 44, (1975), pages 151-163, and U.S. Pat. No. 3,334,110 to Schramm. An example is the reaction product of bisphenol A diglycidyl ether with diphenylmethane diisocyanate in the presence of an appropriate accelerator.

Epoxy resin oligomers may be prepared by condensation of an epoxy resin with a phenol such as a bisphenol. A typical example is the condensation of bisphenol A with a bisphenol A diglycidyl ether to produce an oligomeric diglycidyl ether. In another example a phenol dissimilar to the one used to derive the epoxy resin may be used. For example tetrabromobisphenol A may be condensed with bisphenol A diglycidyl ether to produce an oligomeric diglycidyl ether containing halogens.

Further suitable polyepoxide compounds as well as curing agents for epoxy resins are described in Henry Lee and Kris Neville, "Handbook of Epoxy Resins" McGraw-Hill Book Company, 1967, and Henry Lee "Epoxy Resins", American Chemical Society, 1970.

Some specific useful epoxy resins for blending with the disclosed epoxides include: YX400H (supplied by Japan Epoxy Resins Co., Ltd, epoxy equivalent 195) as a biphenyl type epoxy resin, 3,3',5,5'-tetramethyl-[1,1'-biphenyl]-4,4'-glycidyl ether (biphenyl type epoxy); 195XL (supplied by Sumitomo Chemical Co., Ltd., epoxy equivalent 195) as a cresol novolak type epoxy resin, dicyclopentadiene type epoxy; EBS400T (supplied by Sumitomo Chemical Co., Ltd., epoxy equivalent 400) as a flame-retardant bisphenol type epoxy resin; Tetrabromobisphenol A epoxy (supplied by Dainippon. Ink And Chemicals, Incorporated, trade name: EPICLON-153); brominated bisphenol A type epoxy resin, Trifunctional epoxy resin, Thermosetting epoxy resin, Liquid form Epoxy resin; Tetramethylbisphenoldiglycidyl ether (YX4000: supplied by Japan Epoxy Resins Co., Ltd: epoxy equivalent 190); Bisphenol A glycidyl ether epoxy resin (AER331, manufactured and sold by Asahi Kasei Kogyo Kabushiki Kaisha, Japan; epoxy equivalent: 189); Bisphenol A epoxy: DER-331L, supplied by Dow Chemical Japan Ltd; Phenol novolak type epoxy: EPPN-201, supplied by Nippon Kayaku Co., Ltd.; Bisphenol A type epoxy resin (trade name: Epikote 1001, supplied by Yuka Shell Epoxy K.K.); Cresol novolak type epoxy resin (trade name: ESCN-220F, supplied by Sumitomo Chemical Co., Ltd.); epoxy resin (trade name: Epikote 5045); Epoxy resin (trade name: ESCN220F); brominated bisphenol A type epoxy resin, which is a polyfunctional epoxy resin and super high resistant epoxy resin (trade name: EPPN501H, supplied by Nippon Kayaku Co., Ltd., weight per epoxy equivalent 170); and also epoxy resin, which is a triphenylmethane type epoxy resin (trade name: EPPN501H, supplied by Nippon Kayaku Co., Ltd, weight per epoxy equivalent 164); and also EPPN-052H, supplied by Nippon Kayaku Co., Ltd.); Phenol novolak type epoxy resin (trade name: EPN1182, manufactured by Asahi Kasei Epoxy Co., Ltd., epoxy equivalent of 179 g/eq); Cresol novolac type epoxy resin (trade name: ECN1299, manufactured by Asahi Kasei Epoxy Co., Ltd., epoxy equivalent of 219 g/eq); thermosetting epoxy resin (trade name: EPON 11511360, manufactured by Shell Chemical Company); Liquid-form epoxy resin (tradename: EF-450, produced by Japan REC Co. Ltd); Bisphenol A type epoxy resin (tradename: Epiclon 850S, manufactured by Dainippon Ink & Chemicals, Inc., weight per epoxy equivalent 180); Brominated novolac bisphenol A type epoxy resin (trade name: BREN-S, made by Nippon Kayaku Co., Ltd); and also BREN-105, BREN-304, supplied by Nippon Kayaku Co., Ltd); O-cresol novolac type epoxy resin (trade name: EOCN-102S, manufactured by Nippon Kayaku Co., Ltd); and also EOCN-1020, supplied by Nippon Kayaku Co., Ltd); Phenol novolac type epoxy resin (trade name: EPPN-201, manufactured by Nippon Kayaku Co., Ltd); High purity liquid epoxy resin (trade name: RE-310, manufactured by Nippon Kayaku Co., Ltd; and also RE-303, manufactured by Nippon Kayaku Co., Ltd); Epoxy resin (trade name: Epiclon 153, made by Dainippon Ink & Chemicals, Inc.); Epoxy resin (trade name: Epicoat 1031, supplied by Shell Chemical Company); The epoxy resin, which has a DCPD (dicylopentadiene) skeleton expressed (made by Tohto Kasei Co., Ltd.); Bisphenol A type epoxy resin (trade name: YD-134, made by Tohto Kasei Co., Ltd, weight per epoxy equivalent 250); Brominated bisphenol A type epoxy resin (trade name: YDB-400, made by Tohto Kasei Co., Ltd., weight per epoxy equivalent 400); Brominated bisphenol A type epoxy resin (trade name: YDB-500, made by Tohto Kasei Co., Ltd., weight per epoxy equivalent 500); Bisphenol A type epoxy resin (trade name: YD-115, made by Tohto Kasei Co., Ltd., weight per epoxy equivalent 190); Cresol novolak type epoxy resin (trade name: YDCN-220, made by the Tohto Kasei Co., Ltd.); Epoxy resin which has a naphthalene skeleton (trade name: ESN365, made by Nippon Steel Chemical); Brominated bisphenol A type epoxy resin, (trade name: NC7300L, made by Nippon Kayaku Co., Ltd); Brominated bisphenol A type epoxy resin, (trade name: SM6200, made by Arakawa Chemicals); Cresol novolak type epoxy resin (trade name: YDCN-704, made by Tohto Kasei Co., Ltd., weight per epoxy equivalent 220); Epoxy resin (trade name: YDB400, made by Tohto Kasei Co., Ltd.); Epoxy resin (trade name: EPON1031, made by Shell Chemical Company); Bisphenol A type epoxy resin and its bromination thing (trade name: DER542, Dow Chemical); Organic-functions epoxy resin (trade name: Epicoat 1032H, made by Shell Chemical Company); 4 organic-functions epoxy compounds III (tradename: EXA4700, made by Dainippon Ink); 4 organic-functions epoxy compounds II (trade name: EPICLON430, made by Dainippon Ink); 4 organic-functions epoxy compound I (trade name: EPICORT1031S, made by Shell Chemical Company); Bisphenol A type epoxy resin (trade name: D.E.N485, made by the Dow Chemical Co.); 1,6-bis(2,3-epoxy propoxy)naphthalene (trade name: HP4032, made by Dainippon Ink & Chemicals, Inc., weight per epoxy equivalent 272); Epoxy resin 3: formula (a) resin (trade name: VG3101, made by Mitsui Petrochemical Industries, Ltd., weight per epoxy equivalent 209); Bisphenol A type epoxy resin (trade name: Epicoat 828, the product made from Shell Chemical Company, 380 weight per epoxy equivalent molecular weights 184-194); 4 organic-functions epoxy resin, Tetraglycidyl ether diaminodiphenylmethane (trade name: Epicoat 604, the product made from Shell Chemical Company, 470 weight per epoxy equivalent molecular weights 230-270); Biphenyl type epoxy resin (trade name: EpicoatYX-4000H, the product made from Shell Chemical Company, weight per epoxy equivalents 195); Biphenyl type epoxy resin, (trade name: YX4000H, made by Shell Chemical Company, weight per epoxy equivalent 195); Cresol novolak type epoxy resin (trade name: 195XL, made by Sumitomo Chemical Co., Ltd, weight per epoxy equivalent 195); Fire-resistant bisphenol A type epoxy resin, (trade name: Electronic Broking Systems 400T, made by Sumitomo Chemical Co., Ltd., weight per epoxy equivalent 400); Cresol novolak type epoxy resin for biphenyl type epoxy resin.

The auxiliary epoxy resin can be a solid at room temperature. Thus, in some embodiments, the epoxy resin has a softening point of 25° C. to 150° C. Softening points can be determined according to ASTM E28-99 (2004), "Standard Test Methods for Softening Point of Resins Derived from Naval Stores by Ring-and-Ball Apparatus". The auxiliary epoxy resin can be a liquid or a softened solid at room temperature. Thus, in some embodiments, the auxiliary epoxy resin has a softening point less than 25° C.

The curable composition can comprise the auxiliary epoxy resin in an amount of 0 to 99 wt %, specifically 1 to 99 wt %, more specifically 10 to 90 wt %, still more specifically 40 to 85 wt %, and even more specifically 50 to 80 wt %, based on the total weight of the curable composition.

The curable composition can comprise 1 to 99.9 wt % of a disclosed high heat, high purity epoxide, and 0.1 to 50 wt % of the curing promoter, based on the total weight of the curable composition. In other embodiments, the curable composition comprises 1 to 99.9 wt % of a disclosed high heat, high purity epoxide, 0.1 to 50 wt % of the curing promoter, and 1 to 99 wt % of the auxiliary epoxy resin, based on the total weight of the curable composition.

Many applications dictate that materials meet various standards for flame retardancy. To achieve the required properties, flame retardants can be included in the curable composition.

Suitable flame retardants include phosphorus salts having the formula:

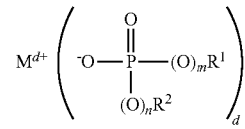

wherein $M^{d+}$ is a metal ion or an onium ion; d is 1, 2, 3, or 4 according to the identity of M and its oxidation state; each occurrence of $R^1$ and $R^2$ is independently C1-C18 hydrocarbyl; and each occurrence of m and n is independently 0 or 1. As described herein, the term "hydrocarbyl", whether used by itself, or as a prefix, suffix, or fragment of another term, refers to a residue that contains only carbon and hydrogen. The residue may be aliphatic or aromatic, straight-chain, cyclic, bicyclic, branched, saturated, or unsaturated. It may also contain combinations of aliphatic, aromatic, straight chain, cyclic, bicyclic, branched, saturated, and unsaturated hydrocarbon moieties. The hydrocarbyl residue, when so stated however, may contain heteroatoms over and above the carbon and hydrogen members of the substituent residue. Thus, when specifically noted as containing such heteroatoms, the hydrocarbyl or hydrocarbylene residue may also contain carbonyl groups, amino groups, hydroxyl groups, or the like, or it may contain heteroatoms within the backbone of the hydrocarbyl residue. In some cases, Md+ is an onium ion. Suitable onium ions include, for example, ammonium cation (NH4+), mono-(C1-C12)-hydrocarbyl ammonium cations, di-(C1-C12)-hydrocarbyl ammonium cations, tri-(C1-C12)-hydrocarbyl ammonium cations, tetra-(C1-C12)-hydrocarbyl ammonium cations, phosphonium cation (PH4+), mono-(C1-C12)-hydrocarbyl phosphonium cations, di-(C1-C12)-hydrocarbyl phosphonium cations, tri-(C1-C12)-hydrocarbyl phosphonium cations, tetra-(C1-C12)-hydrocarbyl phosphonium cations, sulfonium cation (SH3+), mono-(C1-C12)-hydrocarbyl sulfonium cations, di-(C1-C12)-hydrocarbyl sulfonium cations, tri-(C1-C12)-hydrocarbyl sulfonium cations, and the like, and combinations thereof. In some other cases, Md+ is a metal ion. Suitable metal ions include, for example, ions of magnesium, calcium, aluminum, antimony, tin, germanium, titanium, zinc, iron, zirconium, cerium, bismuth, strontium, manganese, lithium, sodium, potassium, and the like, and combinations thereof.

Exemplary organophosphate ester flame retardants include, but are not limited to, phosphate esters comprising phenyl groups, substituted phenyl groups, or a combination of phenyl groups and substituted phenyl groups, bis-aryl phosphate esters based upon resorcinol such as, for example, resorcinol bis-diphenylphosphate, as well as those based upon bis-phenols such as, for example, bis-phenol A bis-diphenylphosphate.

In certain embodiments, the flame retardant materials composition comprises a metal dialkyl phosphinate. As used herein, the term "metal dialkyl phosphinate" refers to a salt comprising at least one metal cation and at least one dialkyl phosphinate anion. The metal dialkyl phosphinate can have formula:

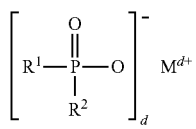

wherein $R^1$ and $R^2$ are each independently C1-C6 alkyl; M is calcium, magnesium, aluminum, or zinc; and d is 2 or 3. Examples of R1 and R2 include methyl, ethyl, n-propyl, isopropyl, n-butyl, tert-butyl, n-pentyl, and phenyl. In some other cases, $R^1$ and $R^2$ are ethyl, M is aluminum, and d is 3 (that is, the metal dialkyl phosphinate is aluminum tris(diethyl phosphinate)).

In certain embodiments, the organophosphate ester includes a bis-aryl phosphate of formula:

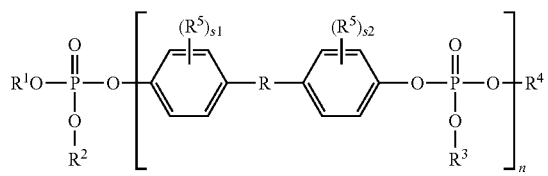

wherein R, $R^5$ and $R^6$ are independently at each occurrence an alkyl group having 1 to 5 carbons and $R^1$-$R^4$ are independently an alkyl, aryl, arylalkyl or alkylaryl group having 1 to 10 carbons; n is an integer equal to 1 to 25; and s1 and s2 are independently an integer equal to 0 to 2. In some embodiments $OR^1$, $OR^2$, $OR^3$ and $OR^4$ are independently derived from phenol, a monoalkylphenol, a dialkylphenol or a trialkylphenol. It is well known that the bis-aryl phosphate is derived from a bisphenol. Exemplary bisphenols include 2,2-bis(4-hydroxyphenyl)propane (so-called bisphenol A), 2,2-bis(4-hydroxy-3-methylphenyl)propane, bis(4-hydroxyphenyl)methane, bis(4-hydroxy-3,5-dimethylphenyl)methane and 1,1-bis(4-hydroxyphenyl)ethane. In one example, the bisphenol comprises bisphenol A.

In certain embodiments, the composition comprises a nitrogen-containing flame retardant comprising a nitrogen-containing heterocyclic base and a phosphate or pyrophosphate or polyphosphate acid. In some example, the nitrogen-containing flame retardant has the formula:

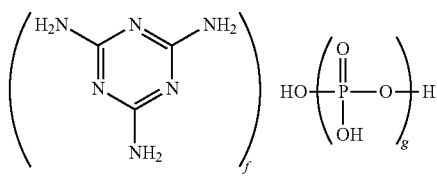

wherein g is 1 to 10,000 and the ratio of f to g is 0.5:1 to 1.7:1, specifically 0.7:1 to 1.3:1, more specifically 0.9:1 to 1.1:1. This formula includes species in which one or more protons are transferred from the polyphosphate group to the melamine group(s). When g is 1, the nitrogen-containing flame retardant is melamine phosphate (CAS Reg. No. 20208-95-1). When g is 2, the nitrogen-containing flame retardant is melamine pyrophosphate (CAS Reg. No. 15541 60-3). When g is, on average, greater than 2, the nitrogen-containing flame retardant is melamine polyphosphate (CAS Reg. No. 56386-64-2). In some other examples, the nitrogen containing flame retardant is melamine pyrophosphate, melamine polyphosphate, or a mixture thereof. When the nitrogen-containing flame retardant is melamine polyphosphate, g has an average value of greater than 2 to 10,000, specifically 5 to 1,000, more specifically 10 to 500. When the nitrogen containing flame retardant is melamine polyphosphate, g has an average value of greater than 2 to 500.

Methods for preparing melamine phosphate, melamine pyrophosphate, and melamine polyphosphate are known in the art, and all are commercially available. For example, melamine polyphosphates may be prepared by reacting polyphosphoric acid and melamine, as described, for example, in U.S. Pat. No. 6,025,419 to Kasowski et al., or by heating melamine pyrophosphate under nitrogen at 290° C. to constant weight, as described in International Patent Application No. WO98/08898 A1 to Jacobson et al.

The composition can include a phosphine compound selected from trihydrocarbylphosphines, trihydrocarbylphosphine oxides, and combinations thereof. The phosphine compound may be a trihydrocarbylphosphine.

The trihydrocarbylphosphine may have formula $PR^3R^4R^5$ wherein $R^3$-$R^5$ are each independently C1-C12 hydrocarbyl, with the proviso that the trihydrocarbylphosphine has at least six carbon atoms. In the context of the trihydrocarbylphosphine and the trihydrocarbylphosphine oxide discussed below, the hydrocarbyl substituent may include, in addition to carbon and hydrogen, a hydroxy substituent (e.g., the hydrocarbyl substituent may be 4-hydroxyphenyl), or an ether oxygen (e.g., the hydrocarbyl substituent may be 4-phenoxyphenyl). Suitable trihydrocarbylphosphines include, for example, triphenylphosphine, allyldiphenylphosphine, diallylphenylphosphine, triallylphosphine, bis(1-naphthyl)(4-hydroxyphenyl)phosphine, bis(4-hydroxyphenyl)(1-naphthyl)phosphine, tris(4-hydroxyphenyl) phosphine, tris(1-naphthyl)phosphine, tris(2-naphthyl)phosphine, bis(4-phenoxyphenyl)(4-hydroxyphenyl)phosphine, bis(4-hydroxyphenyl)(4-phenoxyphenyl)phosphine, tris(4-phenoxyphenyl)phosphine, bis(2,4,5-trimethylphenyl)(4-hydroxyphenyl)phosphine, bis(4-hydroxyphenyl)(2,4,5-trimethylphenyl)phosphine, tris(2,4,5-trimethylphenyl) phosphine, bis(tert-butyl)(4-hydroxyphenyl)phosphine, bis(4-hydroxy-phenyl)(tert-butyl)phosphine, tris(tertbutyl) phosphine, and the like, and combinations thereof.

The phosphine compound may be a trihydrocarbylphosphine oxide. The trihydrocarbylphosphine oxide may have formula $O=PR^3R^4R^5$ wherein $R^3$-$R^5$ are each independently C1-C12 hydrocarbyl, with the proviso that the trihydrocarbylphosphine oxide has at least six carbon atoms. Suitable trihydrocarbylphosphine oxides include, for example, triphenylphosphine oxide, allyldiphenylphosphine oxide, diallylphenylphosphine oxide, triallylphosphine oxide, bis(1-naphthyl)(4-hydroxyphenyl)phosphine oxide, bis(4-hydroxyphenyl)(1-naphthyl)phosphine oxide, tris(4-hydroxyphenyl)phosphine oxide, tris(1-naphthyl)phosphine oxide, tris(2-naphthyl)phosphine oxide, bis(4-phenoxyphenyl)(4-hydroxyphenyl)phosphine oxide, bis(4-hydroxyphenyl)(4-phenoxyphenyl)phosphine oxide, tris(4-phenoxyphenyl)phosphine oxide, bis(2,4,5-trimethylphenyl)(4-hydroxyphenyl)phosphine oxide, bis(4-hydroxyphenyl)(2,4,5-trimethylphenyl)phosphine oxide, tris(2,4,5-trimethylphenyl)phosphine oxide, bis(tert-butyl)(4-hydroxyphenyl)phosphine oxide, bis(4-hydroxy-phenyl)(tert-butyl)phosphine oxide, tris(tert-butyl)phosphine oxide, and the like, and combinations thereof.

The composition may comprise 5 to 95 parts by weight of the phosphorus salt, based on 100 parts by weight total of the phosphorus salt and the phosphine compound. Within this range, the phosphorus salt amount may be at least 10 parts by weight, or at least 20 parts by weight. Also within this range, the phosphorus salt amount may be up to 90 wt %, or up to 80 wt %.

In certain embodiments, the composition may comprise metal hydroxides. Suitable metal hydroxides include all those capable of providing fire retardance, as well as combinations thereof. The metal hydroxide can be chosen to have substantially no decomposition during processing of the fire additive composition and/or flame retardant thermoplastic composition. Substantially no decomposition is defined herein as amounts of decomposition that do not prevent the flame retardant additive composition from providing the desired level of fire retardance. Exemplary metal hydroxides include, but are not limited to, magnesium hydroxide (for example, CAS No. 1309-42-8), aluminum hydroxide (for example, CAS No. 21645-51-2), cobalt hydroxide (for example, CAS No. 21041-93-0) and combinations of two or more of the foregoing. In some cases, the metal hydroxide has an average particle size less than or equal to 10 micrometers and/or a purity greater than or equal to 90 wt %. In some example it is desirable for the metal hydroxide to contain substantially no water, i.e. a weight loss of less than 1 wt % during drying at 120° C. for 1 hour. In some example the metal hydroxide can be coated, for example, with stearic acid or other fatty acid.

Exemplary flame retardant materials include aluminum tris(diethylphosphinate) by itself or in conjunction with a phosphine oxide selected from triphenylphosphine oxide, allyldiphenylphosphine oxide, and combinations thereof. Suitable trihydrocarbylphosphine oxides include, for example, triphenylphosphine oxide, allyldiphenylphosphine oxide, diallylphenylphosphine oxide, triallylphosphine oxide, bis(1-naphthyl)(4-hydroxyphenyl)phosphine oxide, bis(4-hydroxyphenyl)(1-naphthyl)phosphine oxide, tris(4-hydroxyphenyl)phosphine oxide, tris(1-naphthyl)phosphine oxide, tris(2-naphthyl)phosphine oxide, bis(4-phenoxyphenyl)(4-hydroxyphenyl)phosphine oxide, bis(4-hydroxyphenyl)(4-phenoxyphenyl)phosphine oxide, tris(4-phenoxyphenyl)phosphine oxide, bis(2,4,5-trimethylphenyl)(4-hydroxyphenyl)phosphine oxide, bis(4-hydroxyphenyl)(2,4,5-trimethylphenyl)phosphine oxide, tris(2,4,5-trimethylphenyl)phosphine oxide, bis(tert-butyl)(4-hydroxyphenyl)phosphine oxide, bis(4-hydroxy-phenyl)(tert-butyl)phosphine oxide, tris(tert-butyl)phosphine oxide, 9,10-dihydro-9-oxa-10-phosphaphenanthrene-10-oxide, 9,10-dihydro-9-oxa-10-(2,5-dioxotetrahydro-3-furanylmethyl)-10-phosphaphenanthrene-10-oxide and the like, and combinations thereof.

Suitable green FR components are various types, which include Al(OH)3, Mg(OH)2, phosphorous & nitrogen containing compounds and also phosphorous based phenanthrene-10-oxide. Specific examples are a phosphorus compound, which does not contain a halogen atom in the molecule i.e. 9,10-dihydro-9-oxa-10-phosphaphenanthrene-10-oxide, 9,10-dihydro-9-oxa-10-(2,5-dioxotetrahydro-3-furanylmethyl)-10-phosphaphenanthrene-10-oxide etc. It could also be Boron nitride (for epoxy with rubber), phosphorous containing polyester polyol, condensed type phosphoric ester compound, guanidine sulfamate, guanidine phosphate and guanylurea phosphate, phosphazene based compounds, and tris(2-hydroxyphenyl)-phosphine oxide. Commercial phosphoric ester and phosphazene compound can be also used as added type of phosphorus compounds. Phosphoric ester, may be chosen from aromatic condensed phosphoric-acid ester, triphenyl phosphate, Cresyl, and di-2,6-xylenyl phosphate can be used. Among phosphoric ester, as aromatic condensed-phosphoric-acid ester, a 1,3-phenylene-bis(dixylenyl phosphate), a 1,3-phenylene-bis(diphenyl phosphate), etc can be used. As a phosphazene compound, phenoxy phosphazene oligomer, phenoxy toly-loxy phosphazene oligomer, methoxy phenoxy phosphazene oligomer, etc can be used. In the above-mentioned phosphorus compounds, phenoxy phosphazene oligomer and methoxy phenoxy phosphazene oligomer are preferred with respect to the solubility and hydrolysis resistance over a solvent.

In certain embodiments, the composition comprises a flame retardant selected from the group consists of an organophosphate ester, a metal dialkyl phosphinate, a nitrogen-containing flame retardant, metal hydroxides and mixtures thereof. There is no particular restriction on the types of flame retardants that may be used except that the flame retardant is suitably stable at the temperatures employed during electronic materials applications processes. Exemplary flame retardants include melamine (CAS No. 108-78-1), melamine cyanurate (CAS No. 37640-57-6), melamine phosphate (CAS No. 20208-95-1), melamine pyrophosphate (CAS No. 15541-60-3), melamine polyphosphate (CAS #218768-84-4), melam, melem, melon, zinc borate (CAS No. 1332-07-6), boron phosphate, red phosphorous (CAS No. 7723-14-0), organophosphate esters, monoammonium phosphate (CAS No. 7722-76-1), diammonium phosphate (CAS No. 7783-28-0), alkyl phosphonates (CAS No. 78-38-6 and 78-40-0), metal dialkyl phosphinate, ammonium polyphosphates (CAS No. 68333-79-9), low melting glasses and combinations of two or more of the foregoing flame retardants. In some examples, the organophosphate ester is selected from tris(alkylphenyl) phosphate (for example, CAS No. 89492-23-9 or CAS No. 78-33-1), resorcinol bis-diphenylphosphate (for example, CAS No. 57583-54-7), bis-phenol A bisdiphenylphosphate (for example, CAS No. 181028-79-5), triphenyl phosphate (for example, CAS No. 115-86-6), tris(isopropylphenyl) phosphate (for example, CAS No. 68937-41-7) and mixtures of two or more of the foregoing organophosphate esters.

Some other flame retardants include decabromodiphenylethane, decabromodiphenylether (AFR1021, manufactured and sold by Asahi Glass Co., Ltd., Japan); brominated epoxy compounds, non-reactive organic brominated compound e.g: Saytex 8010, SR-245 & pentabromo-diphenyl ether, triphenylphosphine, Sb2O3 (PATOX-M, manufactured and sold by NIHON SEIKO CO., LTD., Japan) as auxiliary FR.

As phosphorus compounds, "KD-302S" by Chemiprokasei Kaisha Ltd, that is phenoxy tolyloxy phosphazene, and the product "PX-200" made from Daihachi Chemicals Industry Ltd., which is aromatic phosphoric ester. Moreover as Mg(OH)2 (magnesium hydroxide), the product having mean particle diameter of 0.9 micrometer was used. "CL303", which is aluminium hydroxide, (mean particle diameter of 3 micrometers) made by Sumitomo Chemical Co., Ltd.

The curable composition can include an inorganic filler. Suitable inorganic fillers include, for example, alumina, silica (including fused silica and crystalline silica), boron nitride (including spherical boron nitride), aluminum nitride, silicon nitride, magnesia, magnesium silicate, glass fibers, glass mat, and combinations thereof. Suitable glass fibers include those based on E, A, C, ECR, R, S, D, and NE glasses, as well as quartz. The glass fiber can have a diameter of 2 to 30 micrometers, specifically 5 to 25 micrometers, more specifically 5 to 15 micrometers. The length of the glass fibers before compounding can be 2 to 7 millimeters, specifically 1.5 to 5 millimeters. Alternatively, longer glass fibers or continuous glass fibers can be used. The glass fiber can, optionally, include an adhesion promoter to improve its compatibility with the poly(arylene ether), the auxiliary epoxy resin, or both. Adhesion promoters include chromium complexes, silanes, titanates, zircon-aluminates, propylene maleic anhydride copolymers, reactive cellulose esters and the like. Suitable glass fiber is commercially available from suppliers including, for example, Owens Corning, Nippon Electric Glass, PPG, and Johns Manville.

Suitable fillers include fused silica powder, fumed silica, spherical silica, thiourea, Al2O3, talc, kaolin, clay (aluminium silicate), antimony trioxide, glass fibers (chopped, milled and cloth), glass bubbles, hollow glass microsphere, aramid fibers, and quartz. It is preferable that the inorganic filler is at least one selected from the group consisting of SiO2, Al2O3, MgO, SiO2, BN, AlN and Si3N4. With this configuration, a suitable thermal expansion coefficient and a thermal conductivity required for the semiconductor package can be obtained. When Al2O3, BN and AlN are employed, a module with high thermal conductivity can be obtained. When MgO is employed, a favorable thermal conductivity can be obtained and a thermal expansion coefficient can be increased. When SiO2 (especially, amorphous SiO2) is employed, a lightweight module having a small thermal expansion coefficient and a small dielectric constant can be obtained. Inorganic powder Titanium dioxide system ceramics, barium titanate series ceramics, Lead titanate system ceramics, strontium titanate system ceramics, titanic acid calcium series ceramics, It is characterized by being titanic acid bismuth system ceramics, titanic acid magnesium system ceramics, and at least one sort of ceramics selected from groups which consist of lead zirconate system ceramics.

Exemplary fillers include an inorganic insulating filler (trade name: baked talc, average particle diameter 0.4 µm, supplied by Nippon Talc K.K.); Al2o3 90 wt % (produced by Showa Denko K.K., 'AS-40', spherical form 12 µm); Aluminium hydroxide (Sumitomo Chemical inorganic filler), Glassiness balloon (Toshiba Ballotini "HSC-110"), Magnesium hydroxide (made by Kyowa Chemical Industry); Silica powder object used the trade name by an ADOMA textile company "ADOMA fine SO-25R" (mean particle diameter of 0.6 micrometer); Silica powder object used the trade name by an ADOMA textile company "ADOMA fine SO-25R" (mean particle diameter of 0.6 micrometer); Titanium dioxide used lot number TR-840 by Fuji Titanium Industry Co., Ltd.; a titanium dioxide with a mean particle diameter of 0.3 micrometer [Fuji Titanium Industry Co., Ltd. make and trade name TR-840].

When an inorganic filler is utilized, the curable composition can comprise 2 to 900 parts by weight of inorganic filler, based on 100 parts by weight total of the disclosed high heat, high purity epoxide, the curing promoter, and the auxiliary epoxy resin. In some embodiments, the curable composition comprises 100 to 900 parts by weight inorganic filler, specifically 200 to 800 parts by weight inorganic filler, and more specifically 300 to 700 parts by weight inorganic filler, based on 100 parts by weight total high heat, high purity epoxide, curing promoter, and auxiliary epoxy resin. In some embodiments, the curable composition comprises less than 50 parts by weight inorganic filler, or less than 30 parts by weight inorganic filler, or less than 10 parts by weight inorganic filler, based of 100 parts by weight total of the disclosed epoxide, the curing promoter, and the auxiliary epoxy resin. In some embodiments, the curable composition can be substantially free of inorganic filler (that is, the composition can comprises less than 0.1 wt % of added inorganic filler, based 100 parts by weight of the disclosed epoxide, the curing promoter, and the auxiliary epoxy resin).

The curable composition can include inorganic filler and fiber treating agents. Exemplary treating agents include: γ-glycidoxypropyltrimethoxysilane [a powder obtained by treating 360.50 parts (78.08% by weight) of a fused silica powder with 2.13 parts (0.46% by weight) of γ-glycidoxypropyltrimethoxysilane], and γ-aminopropyltrimethoxysilane. Coupling agent: 0.3 wt % (produced by AJINOMOTO CO., INC. titanate based-coupling agent '46B'); As a silane coupling agent used for a surface treatment, gamma-aminopropyl trimethoxysilane, gamma-aminopropyl triethoxysilane, gamma-(2-aminoethyl) aminopropyl trimethoxysilane, etc. are mentioned, for example. These may be used independently or may be used together.

There is no limitation in particular the amount of the silane coupling agent used at the time of carrying out a surface treatment, and it is 0.5 to 5.0 weight section still more preferably 0.3 to 10 weight section preferably to raw material talc 100 weight section. When there is too much amount of the silane coupling agent used, there is a possibility that the heat resistance after the lamination application of pressure of an epoxy resin composition may fall. On the other hand, when there is too little amount of the silane coupling agent used, there is a possibility that a resin streak may arise at the time of the lamination application of pressure of an epoxy resin composition.

The curable composition can include rubbers. Exemplary rubbers include carboxyl-terminated butadiene acrylonitrile liquid polymers (CTBN), phenol-terminated butadiene acrylonitrile liquid polymers (PTBN), secondary amine-terminated butadiene acrylonitrile liquid polymers (ATBN), hydroxyl-terminated butadiene acrylonitrile liquid polymers (HTBN), carboxyl-terminated butadiene liquid polymers (CTB), and also following KRATON type polymers i.e., block copolymers, SBS rubbers (styrene-butadiene-styrene block copolymers), SEP rubbers (styrene-ethylene/propylene block copolymers), SEBS rubbers (styrene ethylene/butylene-styrene block copolymers), and liquid polyolefin hydrocarbons. Butadiene acrylonitrile copolymerization rubber ("N220" by Japan Synthetic Rubber Co., Ltd.: 41% of the weight of the amounts of combined acrylonitrile); polyvinyl-acetal resin ("6000AS" by DENKI KAGAKU KOGYO K.K.: 91% of the amount of acetalization); Elastomer SBS [Asahi Chemical Co., Ltd. make and trade name tough PUREN A] or NBR [Ube Industries, Ltd. make and trade name CTBN; Styrene butadiene copolymer (SBS)

[Asahi Chemical Industry Co., Ltd. make and trade name ASAPUREN] can also be used.

The curable composition can include solvents. Suitable solvents may include, for example, a C3-C8 ketone, a C4-C8 N,N-dialkylamide, a C4-C16 dialkyl ether, a C6-C12 aromatic hydrocarbon, a C1-C3 chlorinated hydrocarbon, a C3-C6 alkyl alkanoate, a C2-C6 alkyl cyanide, or a mixture thereof. The carbon number ranges refer to the total number of carbon atoms in the solvent molecule. For example, a C4-C16 dialkyl ether has 4 to 16 total carbon atoms, and the two alkyl groups can be the same or different. As another example, the 2 to 6 carbons in the "C2-C6 alkyl cyanides" include the carbon atom in the cyanide group. Specific ketone solvents include, for example, acetone, methyl ethyl ketone, methyl isobutyl ketone, and mixtures thereof. Specific C4-C8 N,N-dialkylamide solvents include, for example, dimethylformamide, dimethylacetamide, N-methyl-2-pyrrolidone (Chemical Abstracts Service Registry No. 872-50-4), and the like, and mixtures thereof. Specific dialkyl ether solvents include, for example, tetrahydrofuran, ethylene glycol monomethylether, dioxane, and the like, and mixtures thereof. In some embodiments, the C4-C16 dialkyl ethers include cyclic ethers such as tetrahydrofuran and dioxane. In some embodiments, the C4-C16 dialkyl ethers are noncyclic. The dialkyl ether may, optionally, further include one or more ether oxygen atoms within the alkyl groups and one or more hydroxy group substituents on the alkyl groups. The aromatic hydrocarbon solvent may or may not comprise an ethylenically unsaturated solvent. Specific aromatic hydrocarbon solvents include, for example, benzene, toluene, xylenes, and the like, and mixtures thereof. The aromatic hydrocarbon solvent is preferably unhalogenated. That is, it does not include any fluorine, chlorine, bromine, or iodine atoms. Specific C3-C6 alkyl alkanoates include, for example, methyl acetate, ethyl acetate, methyl propionate, ethyl propionate, and the like, and mixtures thereof. Specific C2-C6 alkyl cyanides include, for example, acetonitrile, propionitrile, butyronitrile, and mixtures thereof. In some examples, the solvent is acetone. In certain embodiments, the solvent is methyl ethyl ketone. In certain embodiments, the solvent is methyl isobutyl ketone. In certain embodiments, the solvent is N-methyl-2-pyrrolidone. In certain embodiments, the solvent is ethylene glycol monomethyl ether. Examples include, for example, methyl ethyl ketone (MEK), toluene, MEK and DMF.

When a solvent is utilized, the curable composition can comprise 2 to 100 parts by weight of the solvent, based on 100 parts by weight total of the disclosed high heat, high purity epoxide, the curing promoter, and the auxiliary epoxy resin. Specifically, the solvent amount can be 5 to 80 parts by weight, more specifically 10 to 60 parts by weight, and even more specifically 20 to 40 parts by weight, based on 100 parts by weight total of the disclosed epoxide, the curing promoter, and the auxiliary epoxy resin. The solvent can be chosen, in part, to adjust the viscosity of the curable composition. Thus, the solvent amount can depend on variables including the type and amount of the disclosed epoxide, the type and amount of curing promoter, the type and amount of auxiliary epoxy resin, and the processing temperature used for impregnation of the reinforcing structure with the curable composition.

The curable composition can include one or more additional additives. Suitable additional additives include, for example, dyes, pigments, colorants, antioxidants, heat stabilizers, light stabilizers, plasticizers, lubricants, flow modifiers, drip retardants, antiblocking agents, antistatic agents, flow-promoting agents, processing aids, substrate adhesion agents, mold release agents, toughening agents, low-profile additives, stress-relief additives, and combinations thereof. Exemplary additional additives include, for example, tetrafluoroethylene resin, natural carnauba; 6,6'-(sulfonyl)bis (3,4-dihydro-3-phenyl-2H-1,3-benzoxazine); and polyhedral oligomeric silsesquioxane (POSS) based components; and the like.

The curable compositions can be subjected to various treatments to cure the composition (e.g., initiate reaction of a disclosed epoxy and/or auxiliary epoxy with a curing promoter, such as a polyamine). There is no particular limitation on the method by which the composition may be cured. The composition may, for example, be cured thermally or by using irradiation techniques, including UV irradiation and electron beam irradiation. When heat curing is used, the temperature selected may be 80° C. to 300° C., and preferably 120° C. to 240° C. The heating period may be 1 minute to 10 hours, though such heating period may advantageously be 1 minute to 6 hours, more preferably 3 hours to 5 hours. Such curing may be staged to produce a partially cured and often tack-free resin, which then is fully cured by heating for longer periods or temperatures within the aforementioned ranges.

The disclosed epoxides, curable compositions, and cured compositions can be used in a variety of applications and articles, including any applications where conventional epoxides are currently used. Exemplary uses and applications include coatings such as protective coatings, sealants, weather resistant coatings, scratch resistant coatings, and electrical insulative coatings; adhesives; binders; glues; composite materials such as those using carbon fiber and fiberglass reinforcements. When utilized as a coating, the disclosed compounds and compositions can be deposited on a surface of a variety of underlying substrates. For example, the compositions can be deposited on a surface of metals, plastics, glass, fiber sizings, ceramics, stone, wood, or any combination thereof. The disclosed compositions can be used as a coating on a surface of a metal container, such as those commonly used for packaging and containment in the paint and surface covering industries. In some instances the coated metal is aluminum or steel.

Articles that can be prepared using the disclosed curable compositions include, for example, electrical components and computer components. Articles that can be prepared using the disclosed curable compositions include, for example, automotive, aircraft, and watercraft exterior and interior components. In certain embodiments, the disclosed curable compositions are used for the production of composite materials for use in the aerospace industry.

In certain embodiments, an article comprises the cured composition obtained by curing a curable composition comprising a disclosed epoxide, a curing promoter, optionally, an auxiliary epoxy resin, and optionally one or more additional additives. The curable composition can be used in forming composites used for printed circuit boards. Methods of forming composites for use in printed circuit boards are known in the art and are described in, for example, U.S. Pat. No. 5,622,588 to Weber, U.S. Pat. No. 5,582,872 to Prinz, and U.S. Pat. No. 7,655,278 to Braidwood.

Additional applications for the curable compositions include, for example, acid bath containers; neutralization tanks; aircraft components; bridge beams; bridge deckings; electrolytic cells; exhaust stacks; scrubbers; sporting equipment; stair cases; walkways; automobile exterior panels such as hoods and trunk lids; floor pans; air scoops; pipes and ducts, including heater ducts; industrial fans, fan housings, and blowers; industrial mixers; boat hulls and decks;

marine terminal fenders; tiles and coatings; building panels; business machine housings; trays, including cable trays; concrete modifiers; dishwasher and refrigerator parts; electrical encapsulants; electrical panels; tanks, including electrorefining tanks, water softener tanks, fuel tanks, and various filament-wound tanks and tank linings; furniture; garage doors; gratings; protective body gear; luggage; outdoor motor vehicles; pressure tanks; printed circuit boards; optical waveguides; radomes; railings; railroad parts such as tank cars; hopper car covers; car doors; truck bed liners; satellite dishes; signs; solar energy panels; telephone switchgear housings; tractor parts; transformer covers; truck parts such as fenders, hoods, bodies, cabs, and beds; insulation for rotating machines including ground insulation, turn insulation, and phase separation insulation; commutators; core insulation and cords and lacing tape; drive shaft couplings; propeller blades; missile components; rocket motor cases; wing sections; sucker rods; fuselage sections; wing skins and flairings; engine narcelles; cargo doors; tennis racquets; golf club shafts; fishing rods; skis and ski poles; bicycle parts; transverse leaf springs; pumps, such as automotive smog pumps; electrical components, embedding, and tooling, such as electrical cable joints; wire windings and densely packed multi-element assemblies; sealing of electromechanical devices; battery cases; resistors; fuses and thermal cut-off devices; coatings for printed wiring boards; casting items such as capacitors, transformers, crankcase heaters; small molded electronic parts including coils, capacitors, resistors, and semiconductors; as a replacement for steel in chemical processing, pulp and paper, power generation, and wastewater treatment; scrubbing towers; pultruded parts for structural applications, including structural members, gratings, and safety rails; swimming pools, swimming pool slides, hot-tubs, and saunas; drive shafts for under the hood applications; dry toner resins for copying machines; marine tooling and composites; heat shields; submarine hulls; prototype generation; development of experimental models; laminated trim; drilling fixtures; bonding jigs; inspection fixtures; industrial metal forming dies; aircraft stretch block and hammer forms; vacuum molding tools; flooring, including flooring for production and assembly areas, clean rooms, machine shops, control rooms, laboratories, parking garages, freezers, coolers, and outdoor loading docks; electrically conductive compositions for antistatic applications; for decorative flooring; expansion joints for bridges; injectable mortars for patch and repair of cracks in structural concrete; grouting for tile; machinery rails; metal dowels; bolts and posts; repair of oil and fuel storage tanks, and numerous other applications.

Methods of forming a composite can include impregnating a reinforcing structure with a curable composition; partially curing the curable composition to form a prepreg; and laminating a plurality of prepregs; wherein the curable composition comprises a disclosed epoxide, a curing promoter, optionally, an auxiliary epoxy resin, and optionally, one or more additional additives.

Reinforcing structures suitable for prepreg formation are known in the art. Suitable reinforcing structures include reinforcing fabrics. Reinforcing fabrics include those having complex architectures, including two or three-dimensional braided, knitted, woven, and filament wound. The curable composition is capable of permeating such complex reinforcing structures. The reinforcing structure can comprise fibers of materials known for the reinforcement of plastics material, for example fibers of carbon, glass, metal, and aromatic polyamides. Suitable reinforcing structures are described, for example, in Anonymous (Hexcel Corporation), "Prepreg Technology", March 2005, Publication No. FGU 017b; Anonymous (Hexcel Corporation), "Advanced Fibre Reinforced Matrix Products for Direct Processes", June 2005, Publication No. ITA 272; and Bob Griffiths, "Farnborough Airshow Report 2006", CompositesWorld.com, September 2006. The weight and thickness of the reinforcing structure are chosen according to the intended use of the composite using criteria well known to those skilled in the production of fiber reinforced resin composites. The reinforced structure can contain various finishes suitable for the epoxy matrix.

The method of forming the composite comprises partially curing the curable composition after the reinforcing structure has been impregnated with it. Partial curing is curing sufficient to reduce or eliminate the wetness and tackiness of the curable composition but not so great as to fully cure the composition. The resin in a prepreg is customarily in the partially cured state, and those skilled in the thermoset arts, and particularly the reinforced composite arts, understand the concept of partial curing and how to determine conditions to partially cure a resin without undue experimentation. References herein to properties of the "cured composition" refer to a composition that is substantially fully cured. For example, the resin in a laminate formed from prepregs is typically substantially fully cured. One skilled in the thermoset arts can determine whether a sample is partially cured or substantially fully cured without undue experimentation. For example, one can analyze a sample by differential scanning calorimetry to look for an exotherm indicative of additional curing occurring during the analysis. A sample that is partially cured will exhibit an exotherm. A sample that is substantially fully cured will exhibit little or no exotherm. Partial curing can be effected by subjecting the curable-composition-impregnated reinforcing structure to a temperature of 133 to 140° C. for 4 to 10 minutes.

Commercial-scale methods of forming composites are known in the art, and the curable compositions described herein are readily adaptable to existing processes and equipment. For example, prepregs are often produced on treaters. The main components of a treater include feeder rollers, a resin impregnation tank, a treater oven, and receiver rollers. The reinforcing structure (E-glass, for example) is usually rolled into a large spool. The spool is then put on the feeder rollers that turn and slowly roll out the reinforcing structure. The reinforcing structure then moves through the resin impregnation tank, which contains the curable composition. The varnish impregnates the reinforcing structure. After emerging from the tank, the coated reinforcing structure moves upward through the vertical treater oven, which is typically at a temperature of 175 to 200° C., and the solvent of the varnish is boiled away. The resin begins to polymerize at this time. When the composite comes out of the tower it is sufficiently cured so that the web is not wet or tacky. The cure process, however, is stopped short of completion so that additional curing can occur when laminate is made. The web then rolls the prepreg onto a receiver roll.

While the above-described curing methods rely on thermal curing, it is also possible to effect curing with radiation, including ultraviolet light and electron beams. Combinations of thermal curing and radiation curing can also be used.

In certain embodiments, a composite is formed by a method comprising impregnating a reinforcing structure with a curable composition; partially curing the curable composition to form a prepreg; and laminating a plurality of prepregs; wherein the curable composition comprises a disclosed epoxide, a curing promoter, optionally, an auxiliary epoxy resin, and optionally, one or more additional additives.

In certain embodiments, a printed circuit board comprises a composite formed by a method comprising impregnating a reinforcing structure with a curable composition; partially curing the curable composition to form a prepreg; and laminating a plurality of prepregs; wherein the curable composition comprises a disclosed epoxide, a curing promoter, optionally, an auxiliary epoxy resin, and optionally, one or more additional additives.

Processes useful for preparing the articles and materials include those generally known to the art for the processing of thermosetting resins. Such processes have been described in the literature as in, for example, Engineered Materials Handbook, Volume 1, Composites, ASM International Metals Park, Ohio, copyright 1987 Cyril A. Dostal Senior Ed, pp. 105-168 and 497-533, and "Polyesters and Their Applications" by Bjorksten Research Laboratories, Johan Bjorksten (pres.) Henry Tovey (Ch. Lit. Ass.), Betty Harker (Ad. Ass.), James Henning (Ad. Ass.), Reinhold Publishing Corporation, New York, 1956. Processing techniques include resin transfer molding; sheet molding; bulk molding; pultrusion; injection molding, including reaction injection molding (RIM); atmospheric pressure molding (APM); casting, including centrifugal and static casting open mold casting; lamination including wet or dry lay up and spray lay up; also included are contact molding, including cylindrical contact molding; compression molding; including vacuum assisted resin transfer molding and chemically assisted resin transfer molding; matched tool molding; autoclave curing; thermal curing in air; vacuum bagging; pultrusion; Seeman's Composite Resin Infusion Manufacturing Processing (SCRIMP); open molding, continuous combination of resin and glass; and filament winding, including cylindrical filament winding. In certain embodiments, an article can be prepared from the disclosed curable compositions via a resin transfer molding process.

EXAMPLES

Glass transition temperatures ($T_g$) can be measured on a TA Instruments 2920 M-DS. The thermal scans can range from 30 to 250° C. under a nitrogen atmosphere with a heating rate of 20° C./min.

Samples for Scanning Electronic Microscopy (SEM) can be cut to size, microtomed to obtain a fresh, flat surface for analysis, and etched in toluene at 23° C. for 15 seconds. Then the samples can be coated with gold. The samples can be examined using a Carl Zeiss AG-EVO® 40 Series scanning electron microscope. The conditions may be SEM mode, a probe current of 40 picoamps, HV (high vacuum), and an acceleration voltage of 20 kilovolts.

Dielectric constants and dissipation factors can be measured at 23° C. according to IPC-TM-650 2.5.5.9. Test samples may be in the shape of rectangular prisms having dimensions of 5 centimeters by 5 centimeters by 3.5 millimeters. The samples can be conditioned at 23° C. and 50% relative humidity for a minimum of 24 hours before testing. The measuring cell can be a Hewlett-Packard Impedance Material Analyzer Model 4291B and have a width of 27.5 centimeters, a height of 9.5 centimeters, and a depth of 20.5 centimeters. The electrodes can be Hewlett-Packard Model 16453A and have a diameter of 7 millimeters. Measurements can be conducted using a capacitance method, sweeping a range of frequencies when DC voltage is applied to the dielectric materials. The applied voltage can be 0 2 millivolt to 1 volt at the frequency range of 1 megahertz to 1 gigahertz. Values for dielectric constants (Dk, relative permittivity) and loss tangent (Df, dissipation factor) at frequencies of 100 megahertz, 500 megahertz, and 1000 megahertz (1 gigahertz) can be recorded.

Unnotched Izod impact strength, expressed in joules per meter (J/m), can be measured at 23° C. with a hammer energy of 2 foot-pounds in accordance with ASTM D 4812-2006, "Standard Test Method for Unnotched Cantilever Beam Impact Strength of Plastics". Reported values can reflect an average of 5 specimens per composition.

Softening point determinations were made in accordance with ASTM E28-1999.

$^1$H-NMR spectroscopy was carried out using an Agilent 600 MHz spectrometer. $CDCl_3$ was used as solvent.

HPLC: The purity of reaction samples and products were evaluated by determining the area percentage purity of bisphenol glycidyl ether, impurities and other related compounds by HPLC. Each peak in the chromatogram was integrated and the purities are reported as the area % purity. Each analysis was repeated with triplicate sample preparation and triplicate injections. The HPLC method used is outlined in Table 2.

TABLE 2

| HPLC method | |
|---|---|
| Method name | PPPBP epoxy |
| Wavelength | 230 nm |
| Column | Agilent Zorbax -C18, 4.6 × 150 mm, 5 μm |
| Column oven temperature | 30° C. |
| Injection Vol. | 5 μL |
| Flow rate | 1.00 mL/min |
| Data acquisition | 30 mins |

| Gradient Program | Time | % Milli Q water (With 0.02% OPA) | % Acetonitrile |
|---|---|---|---|
| | 0.00 | 80 | 20 |
| | 10.00 | 80 | 20 |
| | 15.00 | 10 | 90 |
| | 22.00 | 10 | 90 |
| | 23.00 | 80 | 20 |
| | 30.00 | 80 | 20 |

Head Space Gas Chromatography: This method was adopted to estimate the residual epichlorohydrin remaining in reaction samples. The quantification of residual epichlorohydrin in PPPBP glycidyl ether was carried out by dissolving the sample in dimethyl sulfoxide and subsequently analyzed using headspace gas chromatography. The method has detection capability up to 5 ppm in sample matrix. After creation of a calibration curve for epichlorohydrin, the concentration of epichlorohydrin in a sample can be calculated by using the following equation: ECH (ppm)=(Sample concentration obtained from the calibration plot ppm (mcg/ml)×dilution (5 ml))/Sample weight (g). The GC method used is outlined in Table 3.

TABLE 3

| Chromatographic conditions | |
|---|---|
| Column | HP5, 30 m × 0.32 mm (ID) × 250 um thickness |
| Column oven temperature | 40° C. (5 min)-250° C. (2 min, 10° C./min) |
| Flow rate | 1.00 mL/min |
| Inlet temperature | 250° C. |
| FID temperature | 300° C. |

TABLE 3-continued

| Split ratio | 10:1 |
|---|---|
| Headspace conditions | |
| Oven temperature | 120° C. |
| Loop temperature | 130° C. |
| Transfer line temperature | 135° C. |
| Vial equilibration time | 30 min |
| GC cycle time | 40 min |
| Injection duration | 0.5 min |

Example 1. Synthesis of 1,1-bis(4-epoxyphenyl)-N-phenylphthalimidane

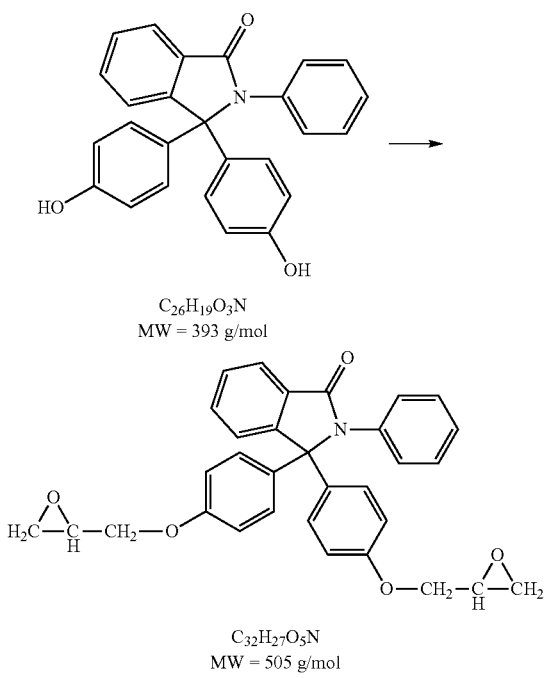

Figure 2:
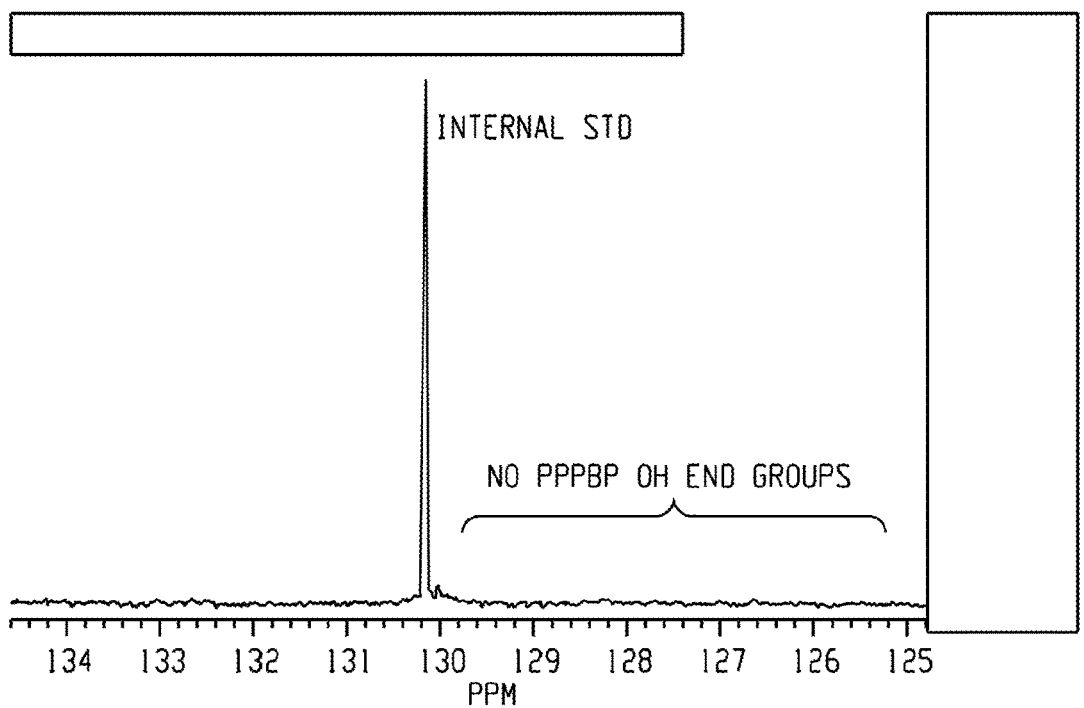
FIG. 2 depicts a $^{31}$P NMR analysis of an exemplary epoxide compound.

To a mixture of PPPBP (100 grams, 254 mmol) in 225 ml epichlorohydrin (1.182 g/ml, 266 grams, 2874 mmol, 11.3 equivalents) was slowly added powdered potassium hydroxide (13.1 grams, 40.6 mmol, 0.16 equiv.). The resultant mixture was stirred at room temperature overnight. The reaction was worked up by treating with water and ethyl acetate. The aqueous layer was re-extracted with ethyl acetate. The combined organic layers were washed with brine and dried over anhydrous $Na_2SO_4$. There was a total of 164 grams of crude product as a clear oil (theoretical yield was 128 grams). The residue was purified by silica gel chromatography. The product was eluted with 9:1 $CH_2Cl_2$/$Et_2O$ (methylene chloride/diethyl ether). The fractions were checked with HPLC. There were 12 fractions. Fractions 109 were combined and dried under vacuum. The yield was 108 grams (84% isolated yield). The purity by HPLC was 99% (by area percent) and the water content by Karl Fisher titration was 0.22%. $^1$H NMR analysis (400 MHz) showed the correct structure (FIG. 1). There was no indication of any secondary alcohol group (~4.4 ppm) from oligomerization. $^{31}$P NMR showed no detectible levels of phenolic groups indicating complete reaction of PPPBP (FIG. 2). DSC showed a transition around 45° C. Thermogravimetric analysis at 800° C. showed 0.17 wt % residue (very little inorganic residue).

Epoxy equivalent weight (EEW) is the weight of resin in grams that contains one mole of epoxy groups. It is also the molecular weight of the resin divided by the number of epoxy groups in one molecule of resin. Table 2 shows epoxy equivalent weight of the product epoxide in purities of 95% to 100%. The product epoxide, as shown in Example 1, is a 2:1 reaction product of epichlorohydrin and PPPBP. One impurity can be the 3:2 oligomer, which is a 3:2 reaction product of epichlorohydrin and PPPBP. Table 4 shows that as purity increases of the product epoxide of Example 1, the EEW reaches 252.5 g/mol.

TABLE 4

| Epoxy equivalent weight | |
|---|---|
| Purity wt % | Epoxy equivalent weight grams/equivalent |
| 100 | 252.5 |
| 99 | 254.7 |
| 98 | 257.0 |
| 97 | 259.2 |
| 96 | 261.5 |
| 95 | 263.7 |

Figure 3:
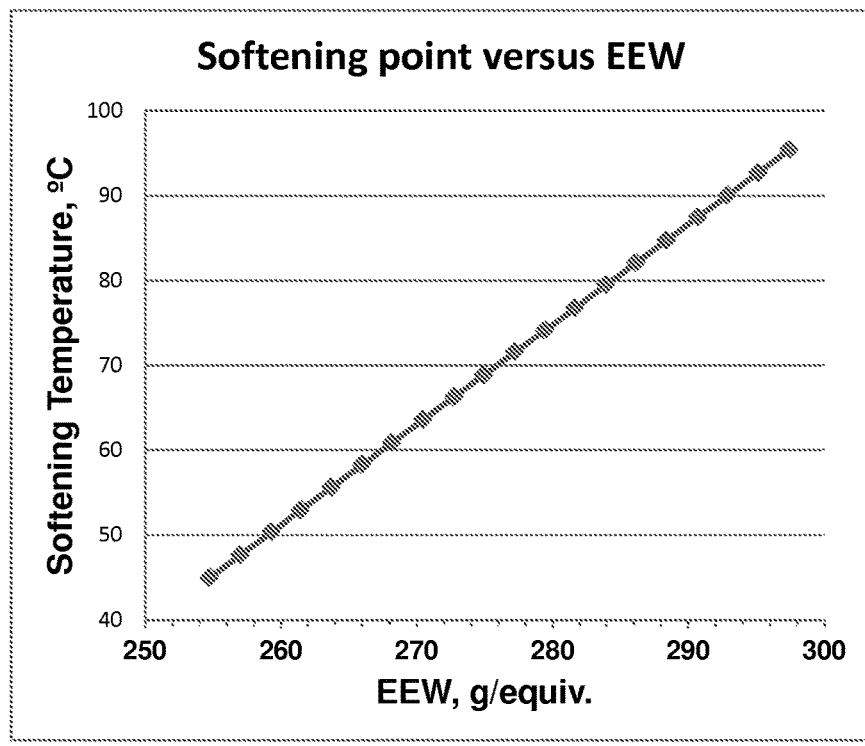
FIG. 3 depicts softening point as a function of epoxy equivalent weight.

Table 5 and FIG. 3 show the melting/softening point of the product of Example 1 as a function of epoxy equivalent weight. The product of Example 1 is a solid at room temperature. At 99% purity, the material softens around 45° C. As the amount of oligomer impurity increases, the melting/softening point also increases.

TABLE 5

| Softening point versus EEW | | | | |
|---|---|---|---|---|
| Entry No. | 2:1 adduct | 3:2 adduct | EEW, g/equiv | Softening point, ° C. |
| 1 | 1 | 0 | 252.5 | |
| 2 | 0.99 | 0.01 | 254.745 | 45 |
| 3 | 0.98 | 0.02 | 256.99 | 47.65 |
| 4 | 0.97 | 0.03 | 259.235 | 50.3 |
| 5 | 0.96 | 0.04 | 261.48 | 52.95 |
| 6 | 0.95 | 0.05 | 263.725 | 55.6 |
| 7 | 0.94 | 0.06 | 265.97 | 58.25 |
| 8 | 0.93 | 0.07 | 268.215 | 60.9 |
| 9 | 0.92 | 0.08 | 270.46 | 63.55 |
| 10 | 0.91 | 0.09 | 272.705 | 66.2 |
| 11 | 0.9 | 0.1 | 274.95 | 68.85 |
| 12 | 0.89 | 0.11 | 277.195 | 71.5 |
| 13 | 0.88 | 0.12 | 279.44 | 74.15 |
| 14 | 0.87 | 0.13 | 281.685 | 76.8 |
| 15 | 0.86 | 0.14 | 283.93 | 79.45 |
| 16 | 0.85 | 0.15 | 286.175 | 82.1 |
| 17 | 0.84 | 0.16 | 288.42 | 84.75 |
| 18 | 0.83 | 0.17 | 290.665 | 87.4 |
| 19 | 0.82 | 0.18 | 292.91 | 90.05 |
| 20 | 0.81 | 0.19 | 295.155 | 92.7 |
| 21 | 0.8 | 0.2 | 297.4 | 95.35 |

Softening points for entries 3-21 were calculated.

For some molding operations, a lower softening point is better than a high softening point (e.g., 45° C. may be better than 95° C.). The higher temperature the faster the cure. During operations such as resin transfer molding, good flow is preferred. However, as resins cure the viscosity increases, which impedes flow. Resin transfer molding to make composites involves having a preform glass or carbon fiber mat or 3-dimensional glass or carbon fiber structure in the mold.

The resin is transferred into the mold at such a rate as to not move the fiber based material. If the resin cures too much during resin transfer, the higher viscosity resin can move the fibrous material. The disclosed resins, via lower softening points, as well as other disclosed advantageous properties, can provide superior moldability compared to known resins, such as those disclosed in WO 2013/183735 wherein resins with higher EEW, higher oligomer content, and higher softening temperatures are disclosed.

Example 2. Evaluation of 1,1-bis(4-epoxyphenyl)-N-phenylphthalimidane in Cured Castings A comparison of 1,1-bis(4-epoxyphenyl)-N-phenylphthalimidane with BPA epoxy (Epon 828; diglycidyl ether of bisphenol A) and TGDDM (N,N,N',N'-tetraglycidyl-4,4'-diaminodiphenylmethane) was done by making and evaluating cured epoxy castings. The curative was dissolved in the epoxy with warming. The mixture was placed in an oven at 100° C. After 30 minutes the temperature was increased to 150° C. After 30 minutes the temperature was increased to 200° C. Upon reaching 200° C., the oven was turned off and allowed to cool overnight. Samples were submitted for analysis by differential scanning calorimetry. The results are shown in Table 6. Clearly, 1,1-bis(4-epoxyphenyl)-N-phenylphthalimidane gave much higher Tgs versus BPA Epoxy (Epon 828) and similar Tgs versus the tetra-functional TGDDM epoxy.

TABLE 6

Differential scanning calorimetry analysis of cured epoxy

| | Epoxy | | |
| --- | --- | --- | --- |
| Curing Agent | Epon 828 Tg (° C.) | DGE PPPBP Tg (° C.) | TGDDM Tg (° C.) |
| 4,4'-methylenedianiline (DMA) | 151.3 | 191.7 | 207.4 |
| m-phenylene diamine (MPD) | 185.4 | 211.5 | — |
| 4-aminophenyl sulfone (DDS) | 173.4 | 250.1 | 254.1 |
| Ethancure 100 | 163 | 221.2 | 206.2 |
| 2,4-EMI | 129.5 | 153.4 | 174.4 |

Figure 4:
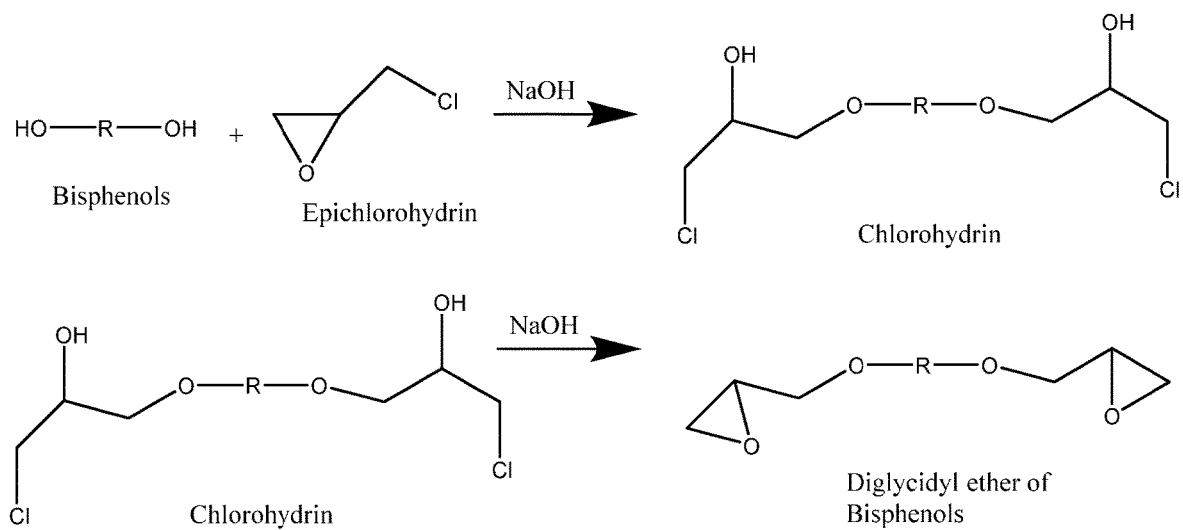
FIG. 4 is a reaction scheme illustrating the mechanism of diglycidyl ether formation.
Figure 5:
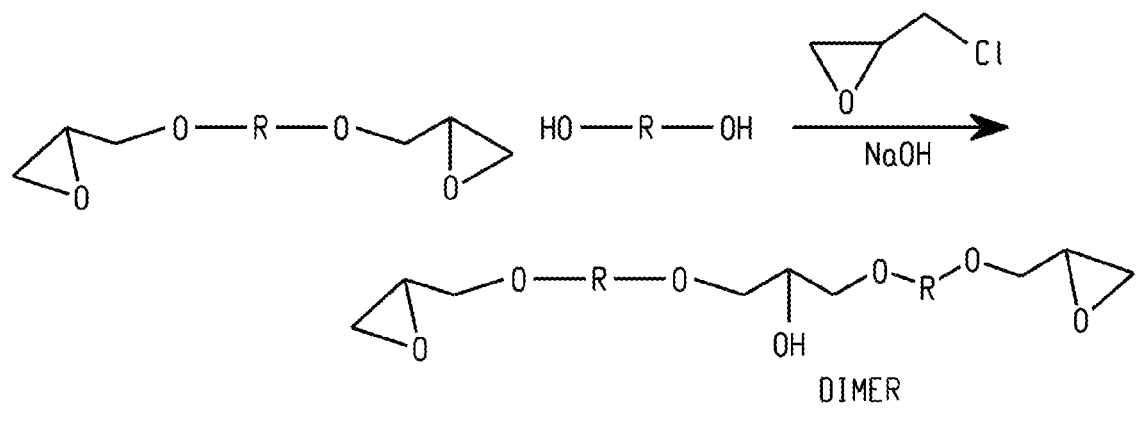
FIG. 5 is a reaction scheme illustrating the formation of oligomeric byproducts in the diglycidyl ether formation reaction.

Example 3. Improved Method for the Formation of the Diglycidyl Ether of Bisphenols Reaction of a bisphenol with epichlorohydrin proceeds through the mechanism as shown in FIG. 4. Bisphenol reacts with epichlorohydrin in the presence of base to form chlorohydrin. The chlorohydrin intermediate undergoes base catalyzed ring closure to form the epoxy ether of bisphenol. However, the presence of base in the reaction mixture not only results in conversion of chlorohydrins to the desired diglycidyl ether, but also may promote undesired oligomerization byproducts, as shown in FIG. 5.

To minimize the extent of oligomer formation, the reaction conditions were modified to improve the yield of the desired glycidyl ether. The following experiments describe the effect of temperature, reaction time, solvent, and other reaction variables on the purity of the desired product. Table 7 provides a list of compounds utilized in the synthetic studies. The employed synthetic process included reaction of bisphenols (listed in Table 7) with epichlorohydrin in the presence of a base (either KOH or NaOH) and a phase transfer catalyst, (tetrabutylammonium bromide (TBAB)).

TABLE 7

| Materials | Code | Supplier | purity |
| --- | --- | --- | --- |
| 3,3'-bis(hydroxylphenyl)-N-phenyl phthalimidine | PPPBP | SABIC | ≥99% |
| 2,2'-(((3,3,3',3'-tetramethyl-2,2',3,3'-tetrahydro-1,1'-spirobi[indene]-6,6'-diyl)bis(oxy))bis(methylene))bis(oxirane)) | SBIBP | SABIC | ≥99% |
| 2,2'-((((3,3,5-trimethylcyclohexane-1,1-diyl)bis(4,1-phenylene))bis(oxy))bis(methylene))bis(oxirane)) | BPI | SABIC | ≥99% |
| 2,2'-((((1-phenylethane-1,1-diyl)bis(4,1-phenylene))bis(oxy))bis(methylene))bis(oxirane)) | BisAP | SABIC | ≥99% |
| Epichlorohydrin | ECH | Fluka | ≥99.5% |
| Tetrabutylammonium Bromide | TBAB | Aldrich | ≥98% |
| Sodium Hydroxide | NaOH | SD fine Chemical, India | 97% |
| Potassium Hydroxide | KOH | | |
| Dichloromethane | DCM | Aldrich | 99.5% |
| Methanol | CH$_3$OH | MERCK | 99.7% |
| Acetonitrile | AN | MERCK | HPLC grade |
| Methyl Ethyl Ketone | MEK | Fischer Scientific | 99% |
| Chloroform | CHCl$_3$ | MERCK | 99.4% |
| Hexane | | MERCK | 95% |
| Sodium Sulphite | Na$_2$SO$_3$ | Aldrich | ≥98% |
| Sodium Sulphate (Anhyd) | Na$_2$SO$_4$ | SD Fine Chemical | 99.5% |

Synthesis of diglycidyl ether of PPPBP

Reaction 1: PPPBP (1 g; 0.00254 moles) and epichlorohydrin (ECH) (2.44 g; 0.02874 moles) were added to a four necked RB flask and stirred with a magnetic stirrer (500 RPM). KOH pellets (0.57 g or 0.01 moles) were added slowly followed by TBAB (0.131 g; 0.00041 moles). The reaction mass was stirred continuously for 20 hours at RT. The initial insoluble mass was extracted with water and ethyl acetate. The washing was continued until a neutral aqueous layer was obtained. The aqueous layer was discarded and the ethyl acetate fraction was separated. The organic layer was dried over $Na_2SO_4$, filtered and evaporated to provide the crude product. The crude product was characterized by LCMS, which showed only unreacted monomer and chlorohydrin intermediates in the product mixture. This result may be a result of the viscous nature of the reaction mixture, which made stirring difficult.

Reaction 2: PPPBP (3.93 g), TBAB (1.6 g) and epichlorohydrin (18.5 g) were added to a four necked RB flask and stirred with a magnetic stirrer. The reaction mass was stirred continuously (500 RPM) for 1 hour at RT and then temperature was raised to 70° C. for 4 hours. The reaction mixture was then allowed to cool to RT and continue stirring overnight. The viscous product was subjected to vacuum distillation and excess epichlorohydrin removed (70-100° C.). The resulting solid was treated with EtOAc and washed with water. The EtOAc extract was dried over $Na_2SO_4$, filtered and evaporated to provide the crude product. The product obtained was characterized by LCMS, which showed no unreacted monomer, but a significant amount of chlorohydrin intermediate present with minor amounts of the desired diglycidyl ether. This result indicated that the reaction could not be completed without addition of a base.

Reaction 3: PPPBP (7.869 g), TBAB (0.128 g) and DCM (40 mL) were added to a four necked flask. The mixture was stirred using a magnetic bead at 500-700 rpm. Epichlorohydrin (5.55 g) was added and the mixture was stirred for 15 minutes. A 50% aq. solution of KOH (2.276 g) was added dropwise through a dropping funnel. The color of the aqueous layer turned pink. The stirring was continued and the 50% KOH solution was added within 2 hours. The reaction was allowed to stir for an additional 2 hours. The reaction mixture contained unreacted white powder which was filtered off. The DCM layer was washed with water until neutral pH (3×). The organic layer was dried over $Na_2SO_4$, filtered and evaporated to provide the crude product. The product obtained was characterized by LCMS, which showed increased amounts of the desired diglycidyl ether, but also dimerization (monochlorohydrin monoepoxy dimer and diepoxy dimer).

Reaction 4: PPPBP (3.93 g), TBAB (0.064 g), DCM (10 mL) and water (20 mL) were added to a four necked flask. The mixture was stirred using a magnetic bead at 500-700 rpm. Solutions of epichlorohydrin (2.77 g) in DCM and KOH (1.138 g; 50% aq. solution) were added dropwise simultaneously over 2 hours. The color of the aqueous layer became pink. The reaction was further allowed to continue until the organic layer became clear (4-5 hrs). The reaction mixture was washed with water until it achieved neutral pH (3×). The solvent was then evaporated. The crude product was characterized by LCMS. This method did not result in significant change in product purity and dimerization products were still observed.

Reaction 5: PPPBP (3.93 g), TBAB (1.61 g) and epichlorohydrin (18.509 g/15.65 mL) were added to a three necked flask. The reactants were stirred using a magnetic bead at 500-700 rpm at 30° C. The reactants started to dissolve and then the reaction temperature was gradually raised to 70° C. The reaction mass became a homogeneous solution. The solution was stirred for an additional 2 hours and a first sample was withdrawn for HPLC analysis. The stirring was continued for one additional hour. Then, a 50% aqueous solution of NaOH (1.2 g) was added dropwise over a period of 3 hours. On complete addition of the NaOH solution the reaction was allowed to stir an additional 1 hour. Aliquots were removed at intervals throughout the reaction and analyzed by HPLC. The reaction mixture was washed with water until it achieved neutral pH (3×). The solvent was evaporated and the purity of the crude product was determined by HPLC.

Figure 6:
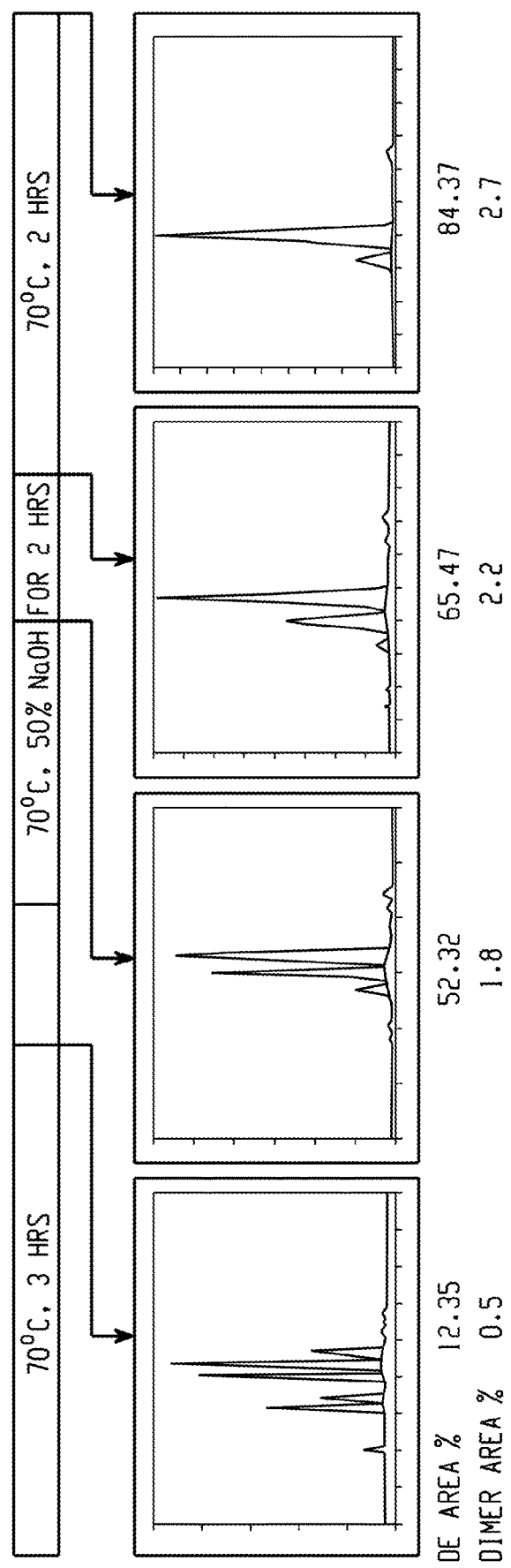
FIG. 6 is a series of HPLC chromatograms showing the progress of formation of the PPPBP diglycidyl ether.

FIG. 6 shows the progress of the reaction from reaction 5. It demonstrates that diglycidyl ether formation (DE area %) significantly increased after base addition. This indicates that addition of base promoted ring closure of the chlorohydrin intermediates. However, addition of base also increased dimer formation and the dimer peak increases in area at higher retention times.

The procedure from reaction 5 was utilized as a basis for further improvement of the reaction in an attempt to obtain crude product with higher purity. The representative procedure of the reaction is given below. The details of the variation of reaction conditions variation and corresponding results obtained are shown in Table 8.

Representative Procedure:

Step A: PPPBP (3.93 g), TBAB (1.61 g) and epichlorohydrin (18.509 g/15.65 mL) were added to a three necked flask. The reactants were stirred using a magnetic bead at 500-700 rpm at elevated temperature (30-90° C.) for 40 minutes.

Step B: 50% aqueous solution of NaOH (1.2 g) was added dropwise over 3 hours.

Step C: On complete addition of NaOH solution the reaction was stirred an additional 1 hour. The reaction mixture was washed with water until it achieved neutral pH (3×). The solvent was evaporated and the crude product was characterized by HPLC.

TABLE 8

| Reaction | 6 | 7 | 8 | 9 | 10 | 11 | 12 | 13 | 14 |
|---|---|---|---|---|---|---|---|---|---|
| Temperature (° C.) | 90 | 70 | 50 | 30 | 50 | RT | 50 | 50 | 50 |
| Step A (Time, Min) | 40 | 40 | 60 | 300 | 60 | 300 | 40 | 60 | 60 |
| Step B (Time, Min) | 150 | 150 | 120 | 120 | 180 | 120 | 150 | 0 | 0 |
| Step C (Time, Min) | 120 | 120 | 120 | 2880 | 120 | 1440 | 120 | 360 | 360 |
| Purity (HPLC area %) | 91.8 | 92.5 | 93.6 | 87.8 | 91.7 | 88.4 | 94.8 | 91.8 | 79.09 |

The best results were obtained with the conditions of reactions 8 and 12, in which the reactions were carried out at 50° C.

The crude product obtained in reaction 8 was purified by silica gel column chromatography. 47 g of silica gel was packed to form the column. DCM/Methanol (99/1) was used as eluent. Elution was initiated by DCM and gradually the solvent polarity was increased by adding methanol. Collected fractions were monitored by TLC. The product containing fractions were combined. The purity of the product was determined to be 98.7% (HPLC area %).

Residual Epichlorohydrin Removal:

A variety of methods were employed to remove excess epichlorohydrin from the crude reaction mixture:

Drying of Crude Product: Crude product containing 700-800 ppm of epichlorohydrin was dried in a vacuum oven for 6 hours at different temperatures. As 100° C. the residual epichlorohydrin was found to be 46.2 ppm.

Hexane treatment: Crude PPPBP diepoxy (1 g) (714 ppm epichlorohydrin) was treated with hexane (30 mL). The mixture was refluxed at 60° C. and then filtered. The residue was washed with hexane and dried in an air circulated thermostatic oven at a variety of temperatures (50-120° C.) for 6 hours. The samples were analyzed for residual epichlorohydrin by head space gas chromatography. The best results were observed when the product was dried at 120° C. for 6 hours, resulting in a concentration of 37 ppm epichlorohydrin.

Water treatment: Crude PPPBP diepoxy (1 g) was treated with water (30 mL). The mixture was refluxed at 100° C. and then filtered. The residue was washed with water and dried in an air circulated thermostatic oven at 100° C. for 6 hours. The samples were analyzed for residual epichlorohydrin by head space gas chromatography technique. The residual epichlorohydrin was found to be 51 ppm.

Aqueous Sodium sulfite treatment: Crude PPPBP diepoxy (1 g) was treated with 10 volumes of aqueous sodium sulfite solution (3.5-10 wt %). The mixture was refluxed at 100° C. and then filtered. The residue was washed with water and dried in an air circulated thermostatic oven at 100° C. for 6 hours. The samples were analyzed for residual epichlorohydrin by head space gas chromatography technique. The samples treated with 3.7% sodium sulphite solution reduced residual epichlorohydrin to 32 ppm. On increasing the level of sodium sulphite to 10 wt %, the residual levels were lowered to a non-detectable range (<5 ppm).

Figure 7:
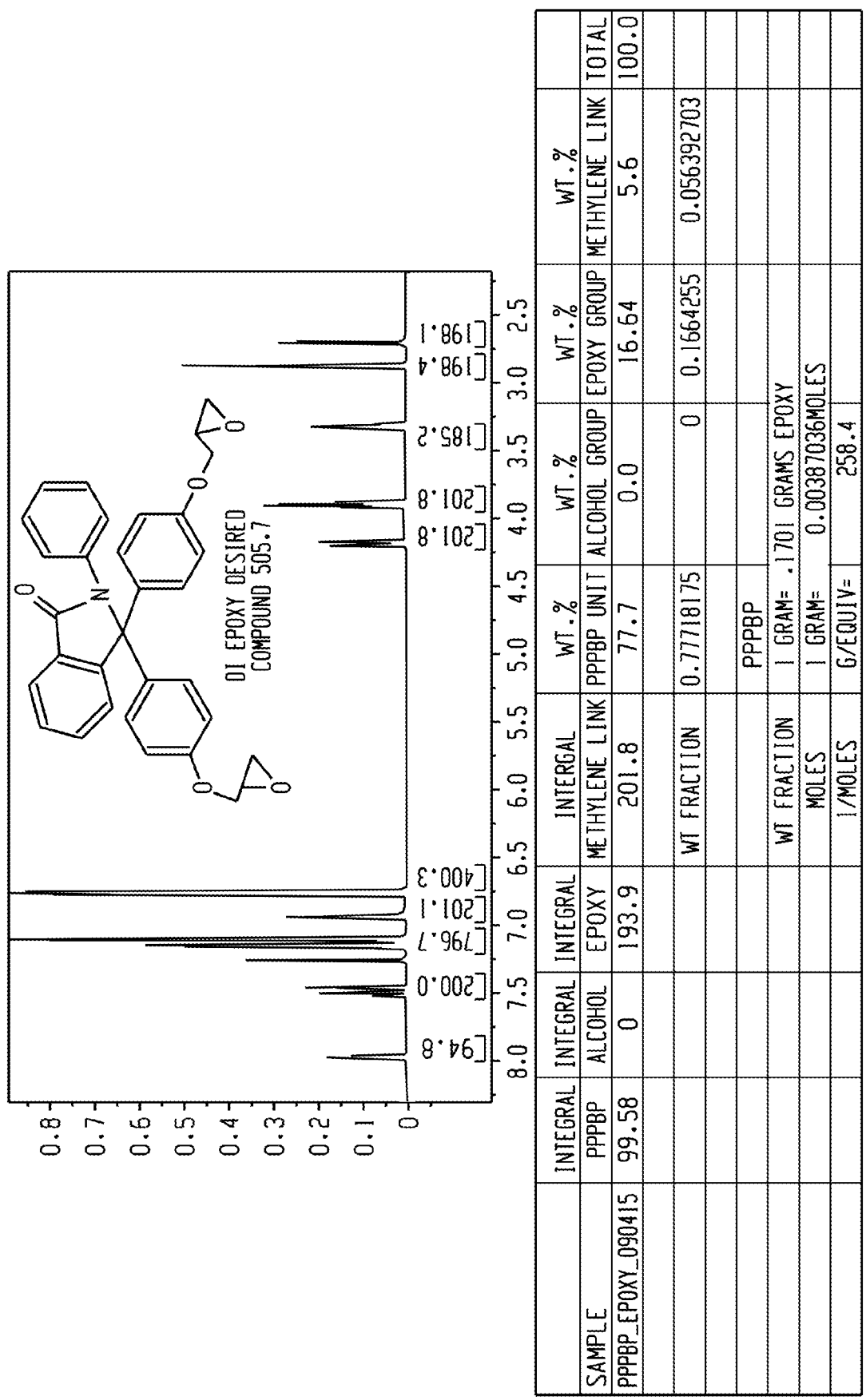
FIG. 7 is an $^1$H-NMR spectrum of the PPPBP diglycidyl ether and a table showing the calculated EEW of the same compound.

Structural Characterization $^1$H-NMR spectroscopy: The $^1$H-NMR spectra of the desired product is the same as that in FIG. 1. The $^1$H-NMR spectroscopy was also used to estimate the epoxy equivalent weight of the sample. FIG. 7 illustrates the method used to determine EEW, which was calculated to be 258.4.

Thermal Characterization

Figure 8:
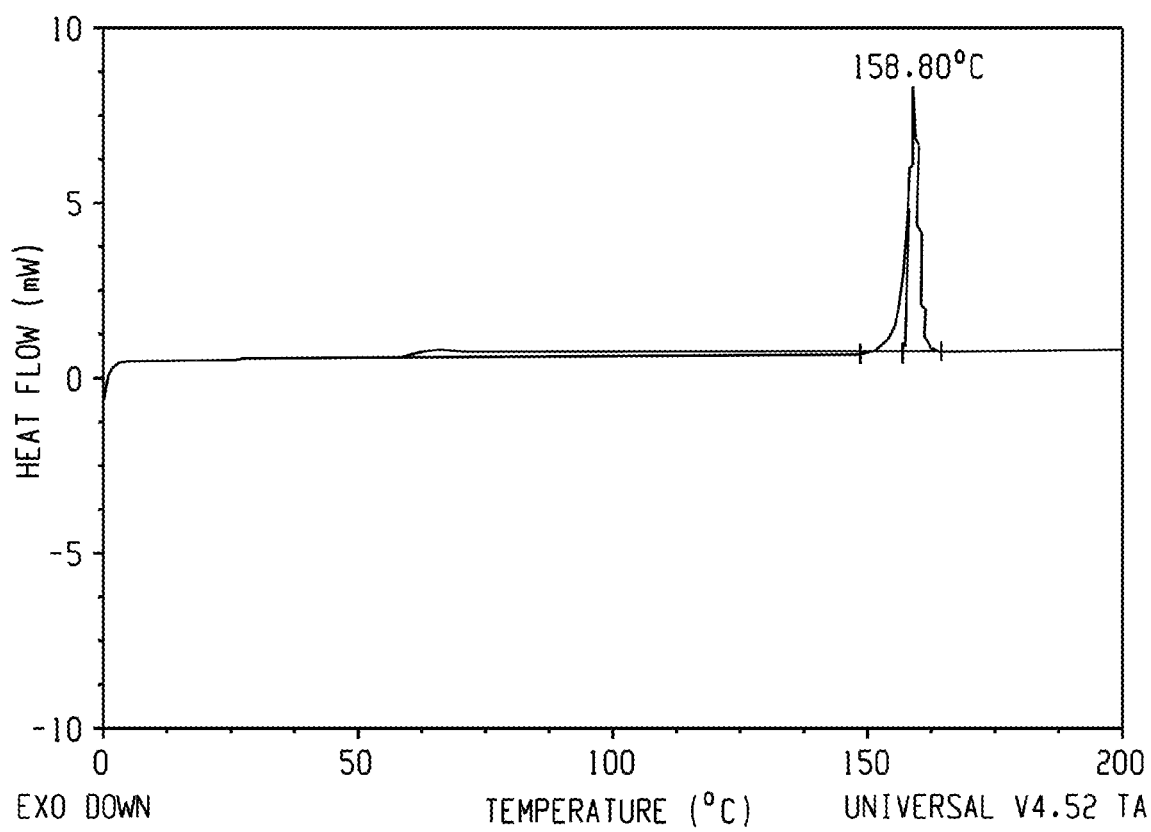
FIG. 8 is a thermogram of the PPPBP diglycidyl ether.

Differential Calorimetry: Thermal characterization was performed with a DSC Q1000 machine. The scan was done up to 200° C. at a rate of 10° C./min under a nitrogen atmosphere. The thermogram of the column chromatography purified sample is shown in FIG. 8. The sample showed a Tg of 60° C. and a sharp melting endotherm at 158.8° C.

Figure 9A:
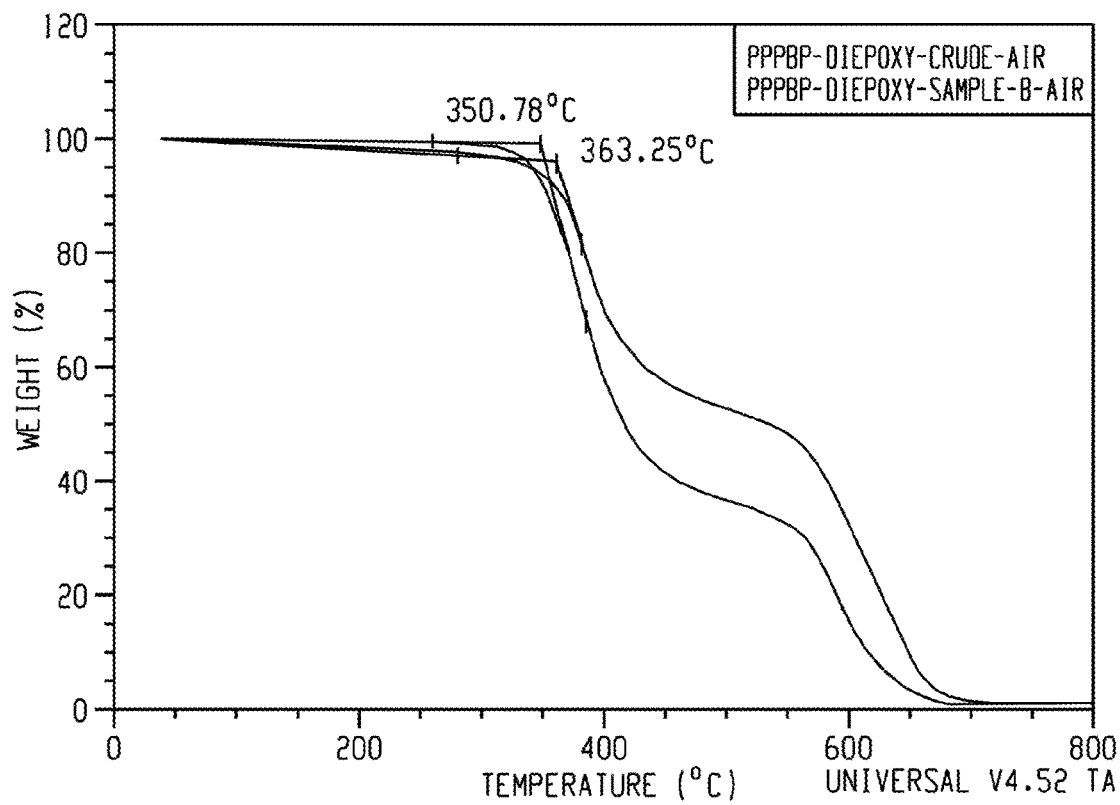
FIG. 9 is a series of thermogravimetric plots of the PPPBP diglycidyl ether and crude PPPBP in air (upper plot) and nitrogen (lower plot).
Figure 9B:
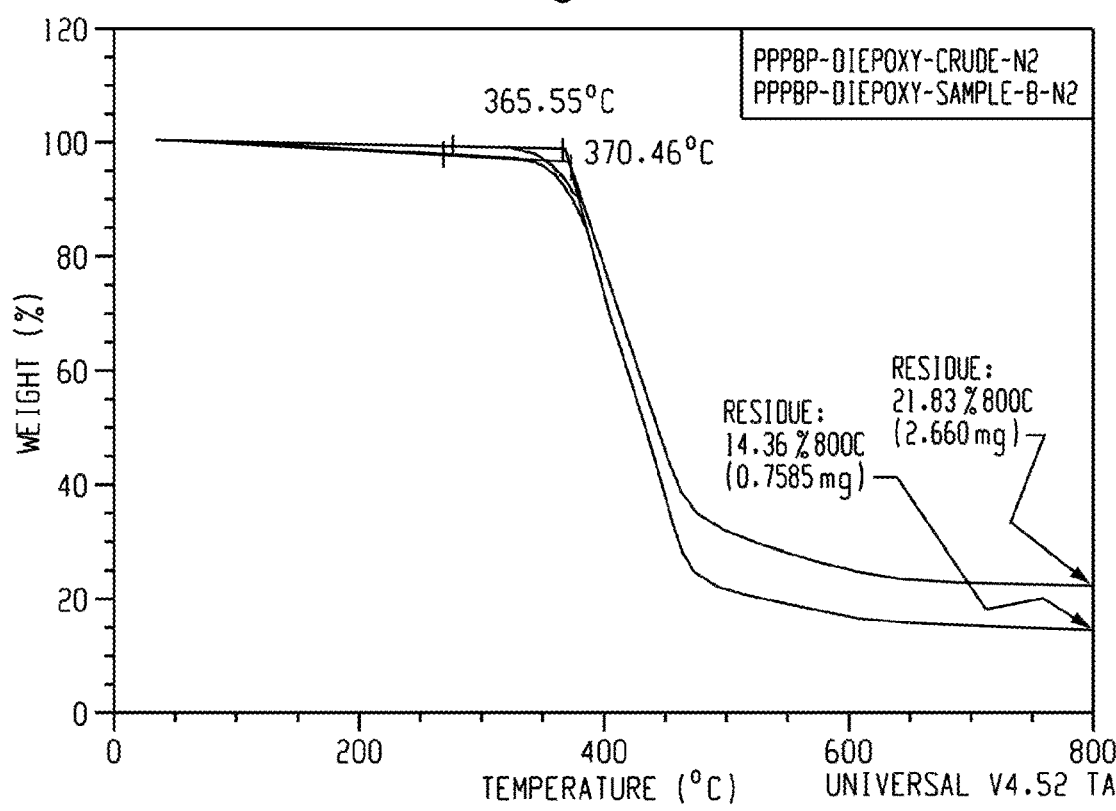

Thermogravimetric Analysis: TGA analysis was performed with a TGA Q5000 machine. The analysis was done under nitrogen and air atmospheres. The maximum temperature was 800° C. and ramp rate was 20° C./min. The TGA plot for sample B (purified PPPBP diglycidyl ether) and PPPBP crude is shown in FIG. 9. The top plot shows TGA under nitrogen while the lower plot shows TGA under ambient air.

Estimation of Ash Content

Ash content was determined by gravimetric method. 2 g of sample was taken in platinum crucible and kept at 800° C. for 8 hours in muffle furnace (Barnsted make). The residual ash was weighed accurately and ash content was calculated based on the initial weight. Samples were analyzed in duplicate. This procedure was done according to ASTM D482. The mean ash content was measured to be 568 ppm (individual runs were 598.7 ppm and 538.2 ppm) with a standard deviation of 43.

Synthesis of diglycidyl ether of SBIBP

Figure 10:
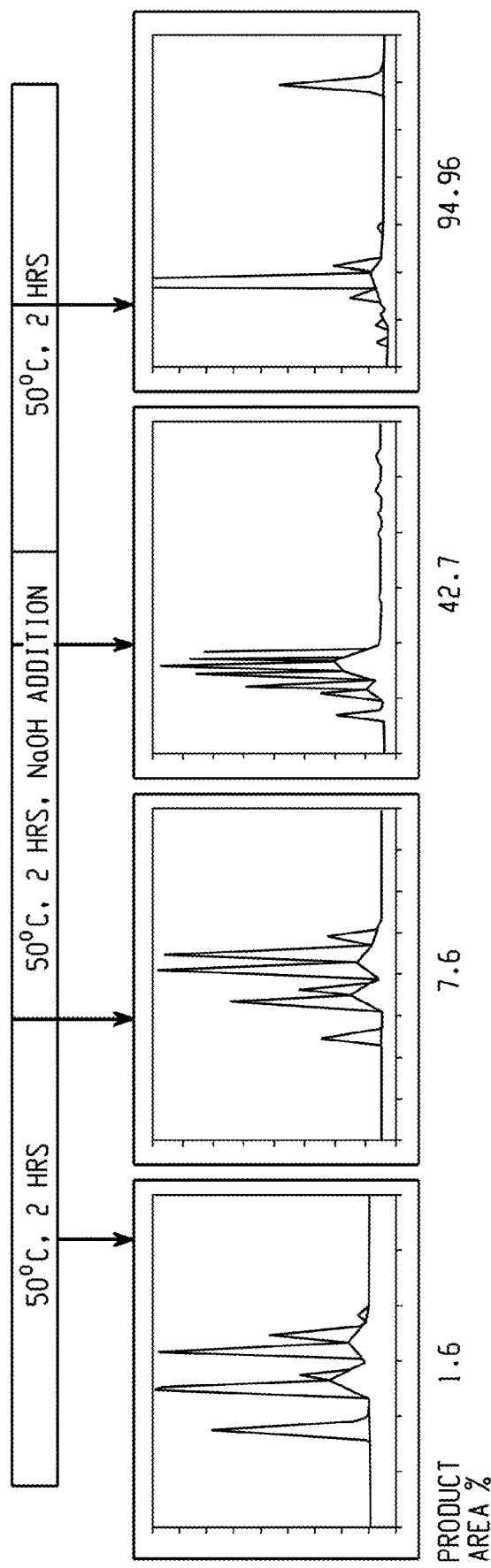
FIG. 10 is a series of HPLC chromatograms showing the progress of formation of the SBIBP diglycidyl ether.

Reaction 15: SBIBP (3.08 g; 0.01 mole), TBAB (1.61 g) and epichlorohydrin (18.65 g/0.2 moles) were added to a three necked round bottom flask. The reaction mixture was stirred for 2 hours at 50° C. Aliquots were withdrawn at the first and second hour. After 2 hours, a 50% aqueous solution of sodium hydroxide (1.2 g) was added dropwise over the course of 2 hours. Another aliquot was collected within one hour of the completion of base addition. The reaction was allowed to stir for an additional 2 hours. All the collected reaction samples were analyzed immediately by HPLC. The results are shown in FIG. 10, which shows that product and oligomer formation was accelerated due to base addition.

Reaction 16: SBIBP (3.08 g; 0.01 mole), TBAB (1.61 g) and epichlorohydrin (18.65 g/0.2 moles) were added to a three necked round bottom flask. The reaction mixture was stirred for 2 hours at 50° C. After 2 hours, a 50% aqueous solution of sodium hydroxide (1.2 g) was added dropwise over the course of 1 hour. The reaction was allowed to continue for another 2 hours. All the collected reaction samples were analyzed immediately after collection by HPLC. These results showed similar levels amounts of desired product and oligomer formation as reaction 15.

Figure 11:
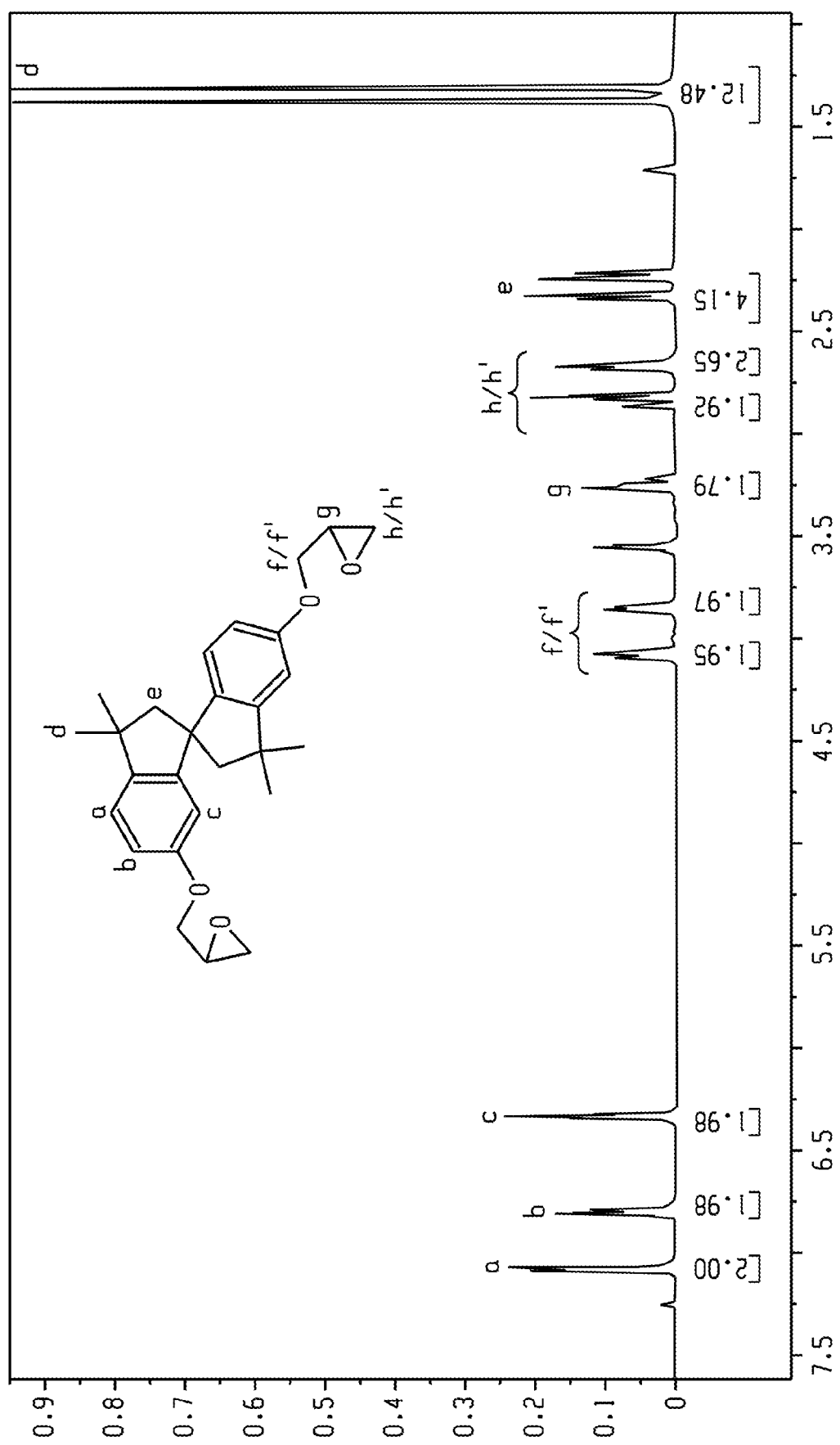
FIG. 11 is an $^1$H-NMR spectrum of the SBIBP diglycidyl ether.

Reaction 17: SBIBP (3.08 g; 0.01 mole), TBAB (1.61 g) and epichlorohydrin (18.65 g/0.2 moles) were added to a three necked round bottom flask. The reaction mixture was stirred for 3 hours at 50° C. The reaction was allowed to cool to room temperature (~25° C.) and a 50% aqueous NaOH solution (1.2 g) was added dropwise over the course of 1 hour. On completion of the addition, the temperature was increased to 35° C. and the reaction was allowed to stir for 4 hours. Aliquots were withdrawn in this final phase of reaction and were analyzed by HPLC. The sample withdrawn 2 hours after base addition showed a purity of 93% while a second sample withdrawn after another 2 hours showed a purity of 95%. Purification by silica gel column chromatography resulted in desired product with a purity of 99.1% by HPLC. $^1$HNMR of the desired product is shown in FIG. 11.

Synthesis of diglycidyl ether of BPI

Figure 12:
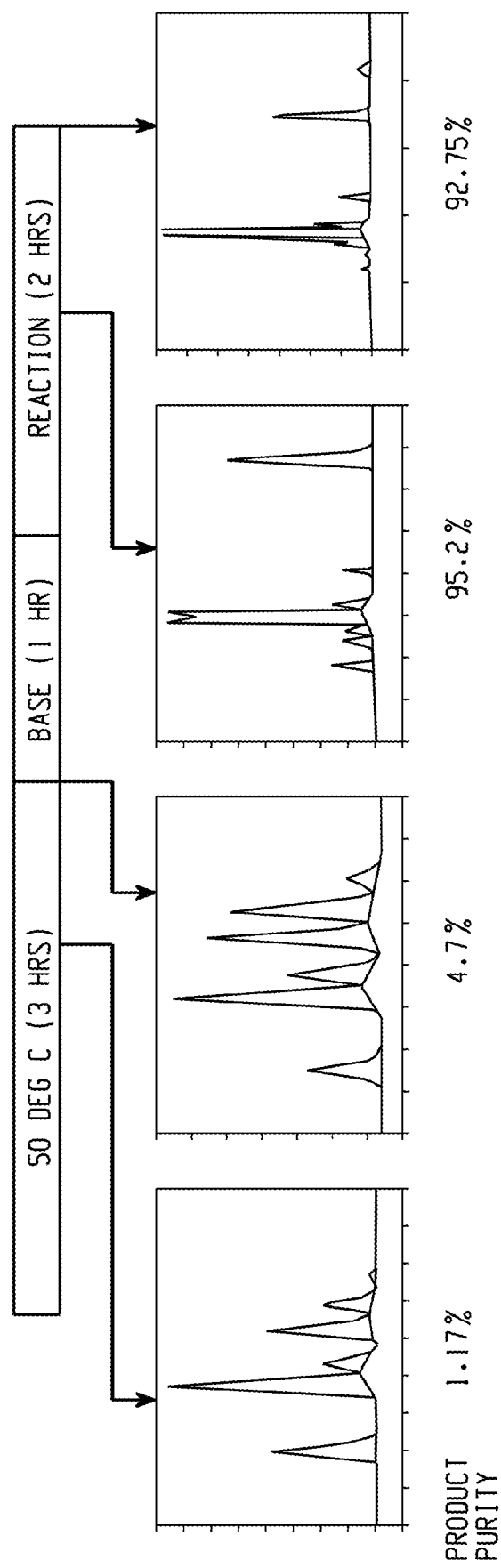
FIG. 12 is a series of HPLC chromatograms showing the progress of formation of the BPI diglycidyl ether.

Reaction 18: BPI (3.104 g; 0.01 mole), TBAB (1.61 g) and epichlorohydrin (18.65 g/0.2 moles) were added to a three necked round bottom flask. The reaction mixture was stirred for 3 hours at 50° C. A 50% aqueous NaOH solution (1.2 g) was added dropwise over the course of 1 hour. The reaction was allowed to stir for another 2 hours and samples were collected to monitor reaction progress. All the collected reaction samples were analyzed immediately after collection by HPLC. The results are shown in FIG. 12.

Figure 13:
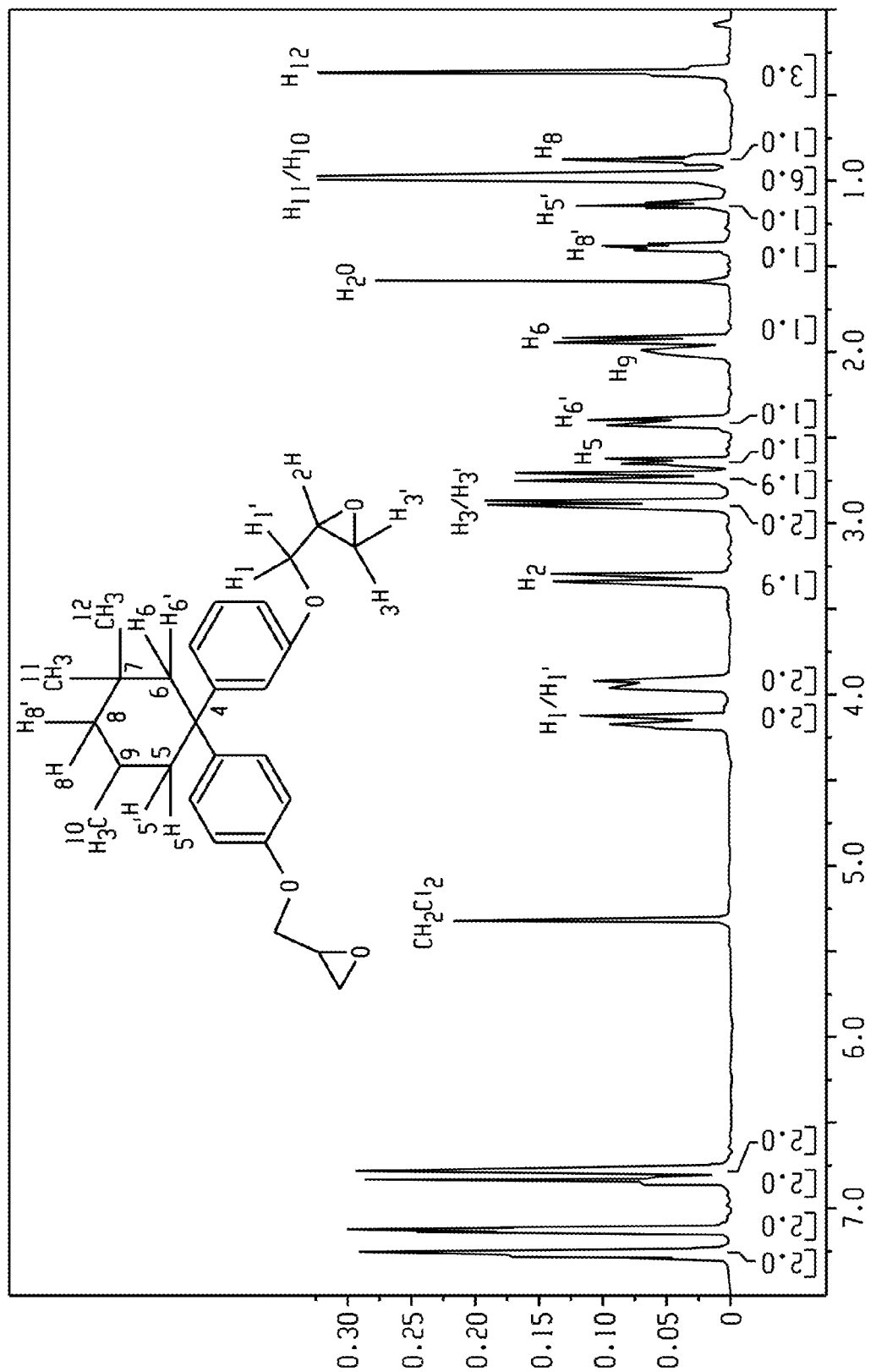
FIG. 13 is an $^1$H-NMR spectrum of the BPI diglycidyl ether.

Reaction 19: BPI (3.104 g; 0.01 mole), TBAB (1.61 g) and epichlorohydrin (18.65 g/0.2 moles) were added to a three necked round bottom flask. The reaction mixture was stirred for 3 hours at 50° C. The reaction was allowed to cool to room temperature (~25° C.) and a 50% aqueous NaOH solution (1.2 g) was added dropwise over the course of 1 hour. On completion of the addition, the temperature was increased to 35° C. and the reaction was allowed to stir for 4 hours. Aliquots were withdrawn in this final phase of reaction and were analyzed by HPLC. The sample withdrawn 2 hours after base addition showed a purity of 93% while a second sample withdrawn after another 2 hours showed a purity of 95%. Purification by silica gel column chromatography resulted in desired product with a purity of 99.1% by HPLC. ¹HNMR of the desired product is shown in FIG. 13.

Synthesis of diglycidyl ether of BisAP

Figure 14:
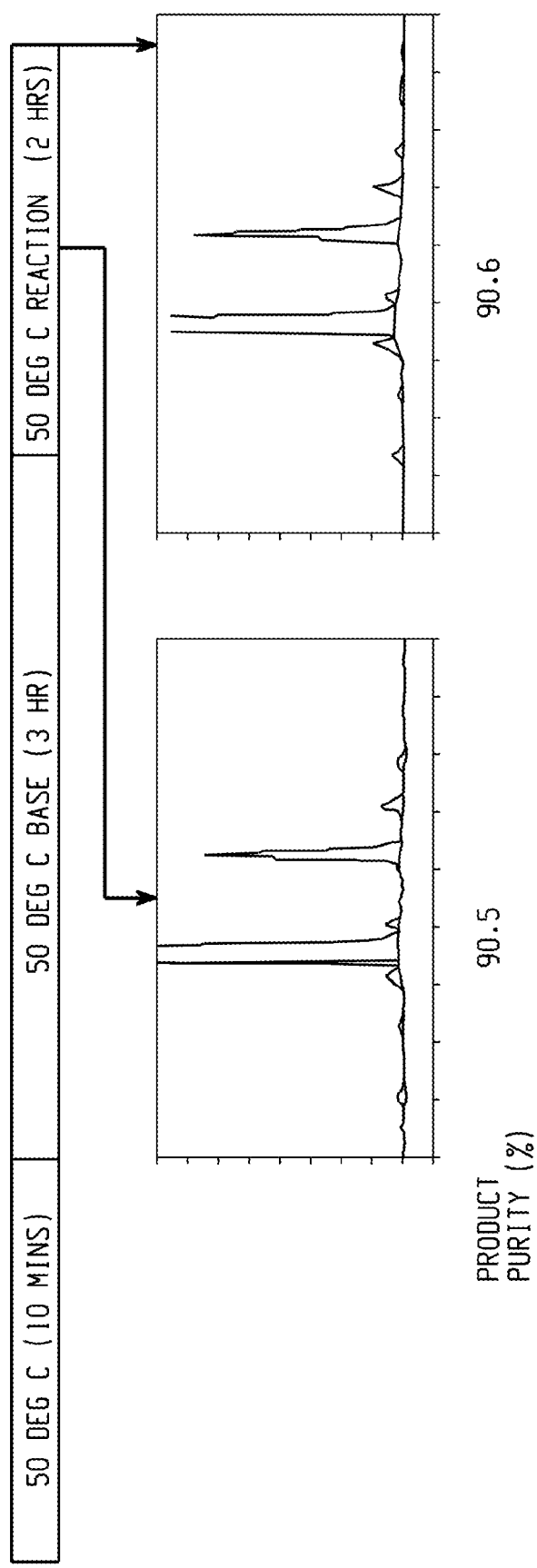
FIG. 14 is a series of HPLC chromatograms showing the progress of formation of the BisAP diglycidyl ether.

Reaction 20: BisAP (2.90 g, 0.01 mole), TBAB (1.61 g) and epichlorohydrin (18.65 g/0.2 moles) were added to a three necked round bottom flask. The reaction mixture was stirred for 10 min at 50° C. A 50% aqueous NaOH solution (1.2 g) was added dropwise over the course of 3 hours. The reaction was allowed to stir for another 2 hours and samples were collected to monitor reaction progress. All the collected reaction samples were analyzed immediately after collection by HPLC. The results are shown in FIG. 14.

Reaction 21: BisAP (2.90 g, 0.01 mole), TBAB (1.61 g) and epichlorohydrin (18.65 g/0.2 moles) were added to a three necked round bottom flask. The reaction mixture was stirred for 3 hours at 50° C. Thus chlorohydrin formation was achieved, but oligomer formation was restricted by not adding base. The reaction temperature was decreased to 30° C. and a 50% aqueous NaOH solution (1.2 g) was added dropwise over the course of 1 hour. On completion of the addition, the reaction was allowed to stir for 2 hours. Aliquots were withdrawn throughout the course of the reaction and were analyzed for purity by HPLC. This method provided a purity of 89% at the completion of the reaction.

Reactions 22 and 23: These reactions were carried out to study the effect of solvent on the product purity. Because the reaction of BisAP with epichlorohydrin is extremely fast in presence of a base, oligomerization takes place simultaneously with product formation. To determine the effect of solvent, two different solvents were screened in separate reactions. BisAP (2.90 g/0.01 mole), TBAB (1.61 g) and epichlorohydrin (18.65 g/0.2 moles) were added to a three necked round bottom flask along with 25 mL of solvent [methyl ethyl ketone (reaction 22) and chloroform (reaction 23)]. The reaction mixtures were stirred for 10 min at 50° C. followed by addition of a 50% aqueous NaOH solution (1.2 g) over a 3 hour period. The reaction was allowed to continue to stir for an additional two hours. The products were isolated and analyzed for purity by HPLC. The crude product from reaction 22 gave a purity of 90.4%, while the crude product from reaction 23 gave a purity of 84.5%. Thus, addition of solvent did not improve the crude product purity.

Figure 15:
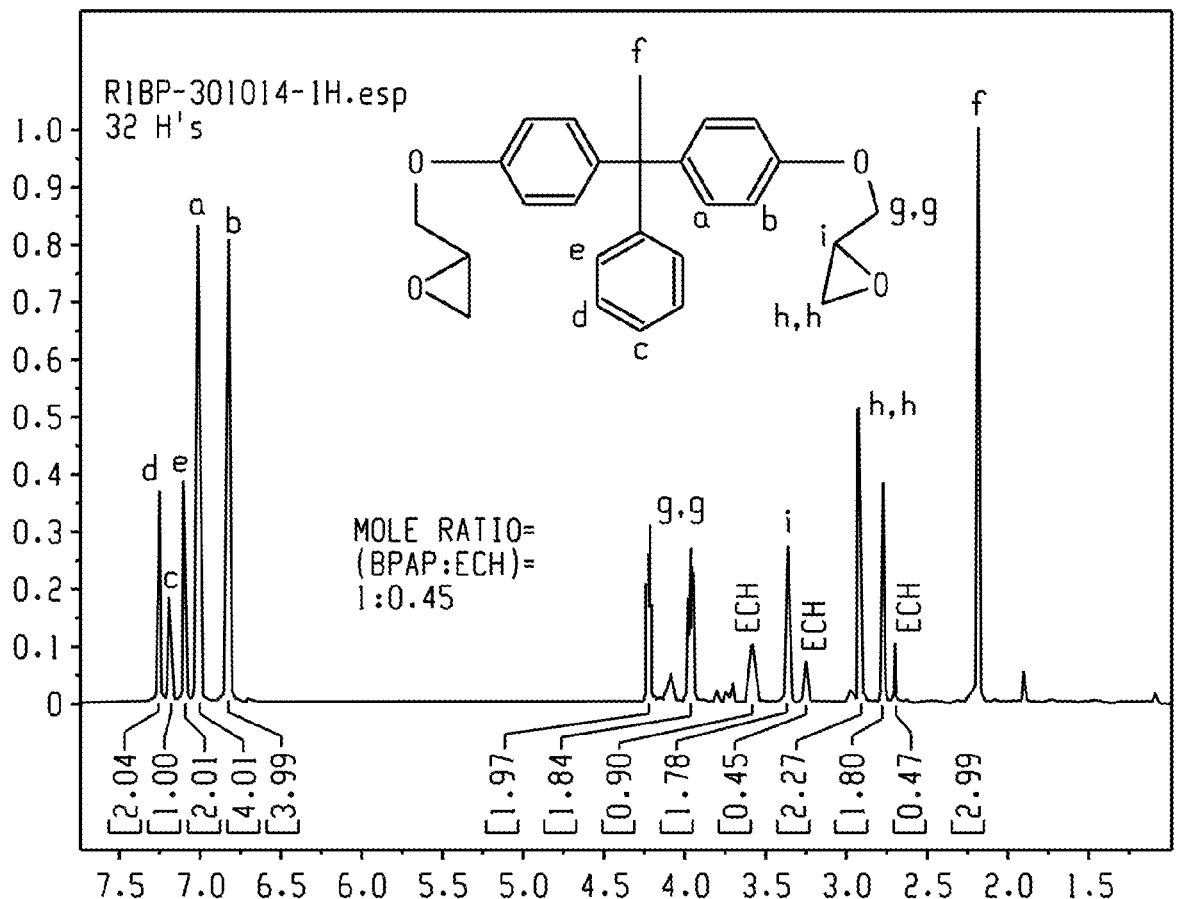
FIG. 15 is an $^1$H-NMR spectrum of the BisAP diglycidyl ether.

Purification by silica gel column chromatography resulted in desired product with a purity of 99.1% by HPLC. ¹HNMR of the desired product is shown in FIG. 15.

Example 4

Synthesis of Low Purity Diglycidyl Ether of Bisphenol

Methods were also developed for the synthesis of diglycidyl ethers of bisphenols with low purity (75-85%). Reaction conditions and stoichiometry were adjusted to achieve the desired composition. The following reactions demonstrate process development.

Diglycidyl ether of SBIBP (Low Purity)

Figure 16:
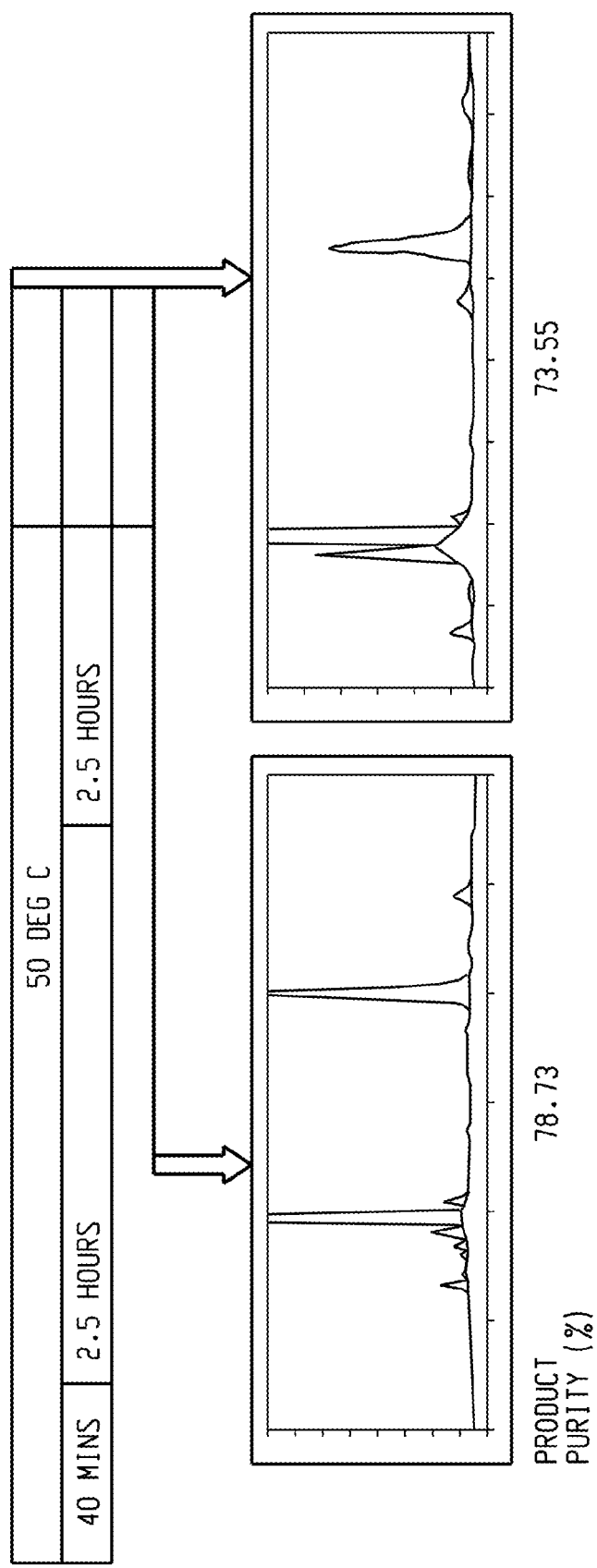
FIG. 16 is a series of HPLC chromatograms showing the progress of formation of the SBIBP diglycidyl ether.

Reaction 24: SBIBP (3.08 g; 0.01 mole), TBAB (1.61 g) and epichlorohydrin (5.55 g/0.06 moles) were added to a three necked round bottom flask. The reaction mixture was stirred for 40 mins at 90° C. A 50% aq sodium hydroxide solution (1.2 g) was added dropwise over the course of 2.5 hours. The reaction was allowed to stir for an additional 3.5 hours and samples were collected to monitor reaction progress. All the collected reaction samples were analyzed immediately after collection by HPLC. The reaction progress is illustrated by the HPLC chromatograms in FIG. 16.

Reaction 25: SBIBP (3.08 g; 0.01 mole), TBAB (1.61 g) and epichlorohydrin (5.55 g/0.06 moles) were added to a three necked round bottom flask. The reaction mixture was stirred for 40 mins at 90° C. A 50% aq sodium hydroxide solution (1.2 g) was added dropwise over the course of 2.5 hours. The reaction was allowed to stir for an additional 1 hour and samples were collected to monitor reaction progress. All the collected reaction samples were analyzed immediately after collection by HPLC. The purity achieved was 77.2%.

Diglycidyl ether of BPI (Low Purity)

Reaction 26: BPI (3.104 g; 0.01 mole), TBAB (1.61 g) and epichlorohydrin (5.55 g/0.06 moles) were added to a three necked round bottom flask. The reaction mixture was stirred for 40 mins at 90° C. A 50% aq sodium hydroxide solution (1.2 g) was added dropwise over the course of 2.5 hours. The reaction was allowed to stir for an additional 1 hour and samples were collected to monitor reaction progress. The product was isolated and purity was determined to be 75.4% by HPLC (with 21% oligomer content).

Diglycidyl ether of BisAP (Low Purity)

Reaction 27: BisAP (2.90 g, 0.01 mole), TBAB (1.61 g) and epichlorohydrin (5.55 g/0.06 moles) were added to a three necked round bottom flask. The reaction mixture was stirred for 40 mins at 90° C. A 50% aq sodium hydroxide solution (1.2 g) was added dropwise over the course of 2.5 hours. The reaction was allowed to stir for an additional 1 hour and samples were collected to monitor reaction progress. The product was isolated and purity was determined to be 70.6% by HPLC (with 27% oligomer content).

The product purity was lower than the desired range of 75-85%. In an attempt to improve the yield to the desired range, the reaction conditions were modified as shown in Table 9.

TABLE 9

| Reaction | 28 | 29 | 30 |
| --- | --- | --- | --- |
| Reaction Temp (° C.) | 90 | 70 | 90 |
| BisAP/ECH ratio (mol/mol) | 0.01/0.06 | 0.01/0.06 | 0.01/0.1 |
| Step A: Reaction time prior to base addition | 40 | 40 | 60 |
| Step B: time for base addition | 150 | 150 | 60 |
| Step C: Reaction time after base addition | 30 | 60 | 60 |
| Diglycidyl ether of BisAP (Purity %) | 71.2 | | 81.8 |

Diglycidyl ether of PPPBP (low purity)

Low purity diglycidyl ether of PPPBP was also synthesized by altering the stoichiometry of PPPBP and epichlorohydrin. The amount of base (50% NaOH aqueous solution, 1.2 g) and TBAB (1.61 g) added was kept constant. Table 10 shows the reaction modifications made to achieve the targeted 75-85% purity.

TABLE 10

| Reaction | 31 | 32 | 33 | 34 |
| --- | --- | --- | --- | --- |
| Reaction Temp (° C.) | 90 | 90 | 75 | 80 |
| PPPBP/ECH ratio (mol/mol) | 0.01/0.06 | 0.01/0.1 | 0.01/0.145 | 0.01/0.128 |
| Step A: Reaction time prior to base addition (min) | 40 | 40 | 40 | 40 |
| Step B: Reaction time for base addition (min) | 150 | 150 | 60 | 60 |

TABLE 10-continued

| Reaction | 31 | 32 | 33 | 34 |
|---|---|---|---|---|
| Step C: Reaction time after base addition (min | 30 | 30 | 30 | 60 |
| Diglycidyl ether of BisAP (Purity %) | 50% | 71% | 88% | 80.5% |

Example 5. Effect of Purity on Viscosity

In general, in the above reactions, as the purity decreases the amount of higher molecular weight oligomers increases. This higher molecular weight fraction will increase the overall viscosity of the diglycidyl ether product. In general, lower viscosity resins are preferred for increased flow and better wetting of fillers and reinforcing fibers. The effect of oligomers on the viscosity of PPPBP epoxy is shown in Example 5 and Comparative Example 5 in Table 11. The viscosities were measured using a spindle viscometer (Digital Brookfield Rotational Viscometer: Thermosel System for elevated temperature testing). Samples were placed in the disposable Spindle/Chambers assemble and the temperature was increased to test temperature. After equilibration for 5 minutes at the test temperature, the viscosity was determined.

TABLE 11

| | Example 5 | Comparative Example 5 | |
|---|---|---|---|
| Purity | 97% | 88% | |
| Oligomer | 3% | 12% | |
| Temperature (° C.) | Viscosity (cPs) | Viscosity (cPs) | Viscosity increase (%) |
| 115 | 21000 | 27750 | 32.1 |
| 120 | 12680 | 16950 | 33.7 |
| 130 | 4130 | 5446 | 31.9 |
| 140 | 1630 | 2120 | 30.1 |
| 150 | 774 | 985 | 27.3 |
| 160 | 413 | 513 | 24.2 |
| 170 | 230 | 275 | 19.6 |

Examples 6-9. Casting Studies

Judicious formulating can tailor the polymer networks and modify the performance of epoxy resins. For example, high glass transition temperatures (Tg) are often desired in composites used in transportation, aerospace, and electronic applications. An important method of increasing Tg is to increase the crosslink density of the network. However, a common feature of highly crosslinked matrixes is their inherent brittleness.

Significant efforts have focused on improved toughness of epoxy resins via rubber-toughened epoxy. However, the addition of a rubber phase into the stiff epoxy matrix results in decreased thermal and mechanical properties (e.g. tensile modulus and yield strength). In addition, the high level of unsaturation in these rubber modifiers can provide routes for oxidative degradation reactions. Consequentially, epoxy resins toughened with elastomeric particles are used predominantly in low temperature applications.

High-functionality epoxy resins have been used to obtain high Tg cure material. Trifunctional triglycidyl p-amino phenol (TGAP), tetra-functional tetraglycidyldiamino diphenylmethane (TGDDM) and aromatic diamines such as diethyltoluene diamine (DETDA) give a Tg greater than 200° C.

Hence, a challenge in formulating epoxy resins is to obtain high Tg materials while maintaining or increasing the toughness. One approach to lowering the crosslink density would be to use a di-functional more rigid epoxy instead of tri- and tetra-functional epoxy resins. To investigate this approach, properties of di- and tetra-functional epoxies cured with an aromatic diamine were compared by making castings. The materials used for the study are listed in Table 12.

TABLE 12

| Component | Description | Supplier |
|---|---|---|
| TGDDM | ARALDITE MY 721: tetraglycidyldiamino diphenylmethane | Huntsman Advanced Materials |
| DGEBPA | DER 332: Diglycidyl ether of bisphenol A | Dow Chemical |
| DDS | 4-aminophenyl sulfone | Sigma-Aldrich |
| MDA | 4,4'-Methylenedianiline | Sigma-Aldrich |
| DETDA | Diethyltoluenediamine | Sigma-Aldrich |
| 2,4-EMI | 2-ethyl-4-methylimidazole | Sigma-Aldrich |
| 1-MI | 1-methylimidazole | Sigma-Aldrich |
| MNA | Methyl-5-norbornene-2,3-dicarboxylic anhydride | Sigma-Aldrich |

General procedure for making castings: Solid hardeners were dissolved in the epoxy resin by warming and stirring. The stoichiometry had 15-17% excess epoxy equivalents. The homogeneous epoxy/hardener solution was degassed in a vacuum oven and then poured into a mold which was preheated to 120° C. The filled mold was placed in an oven at 120° C. and the cure temperature was programmed up to 220° C.

The performance properties of the PPPBP diglycidyl ether were compared to di-functional DGEBPA and tetra-functional TGDDM. The epoxy resins were cured with 3 different aromatic diamines, MDA, DDS, and DETDA. All formulations contained 16.5% excess equivalents of the epoxy groups. The Tg of the aromatic diamine cured epoxy resins were determined for each of these compositions. Table 13 shows that the PPPBP epoxy based castings (6-8) and the TGDDM based castings (Comparative Examples 6-8) exhibited Tg values greater than 200° C., while the DGEBPA based castings (Comparative Examples 9-11) possessed Tg values below 175° C.

TABLE 13

| Ex. | PPPBP diglycidyl ether (wt %) | TGDDM (wt %) | DGEBPA (wt %) | MDA (wt %) | DDS (wt %) | DETDA (wt %) | Tg (° C.) |
|---|---|---|---|---|---|---|---|
| 6 | 86.29 | — | — | 13.71 | — | — | 201.2 |
| 7 | 83.39 | — | — | — | 16.61 | — | 250.1 |
| 8 | 87.51 | — | — | — | — | 12.49 | 221.2 |
| C.E. 6 | — | 73.25 | — | 26.76 | — | — | 207.4 |

TABLE 13-continued

| Ex. | PPPBP diglycidyl ether (wt %) | TGDDM (wt %) | DGEBPA (wt %) | MDA (wt %) | DDS (wt %) | DETDA (wt %) | Tg (° C.) |
|---|---|---|---|---|---|---|---|
| C.E. 7 | — | 68.6 | — | — | 31.41 | — | 254.1 |
| C.E. 8 | — | 75.26 | — | — | — | 24.74 | 206.2 |
| C.E. 9 | — | — | 81.89 | 18.11 | — | — | 151.3 |
| C.E. 10 | — | — | 78.33 | — | 21.67 | — | 173.4 |
| C.E. 11 | — | — | 83.43 | — | — | 16.57 | 163 |

Unnotched impact strength was used to compare the impact strength of the castings of example 7 and comparative example 7. The results are summarized in Table 14 below. Unnotched Izod impact strength was measured at 23° C. with a hammer energy of 2 ft-lbs in accordance with ASTM D 4812-2006. Reported values reflect an average of 5 specimens per composition. As can be seen from the data, the impact strength of inventive example 7 has a 23% higher impact strength compared to the tetra-functional epoxy resin of comparative example 7.

TABLE 14

| Ex. | PPPBP diglycidyl ether (wt %) | TGDDM (wt %) | DDS (wt %) | Impact strength (J/m) |
|---|---|---|---|---|
| 7 | 83.39 | — | 16.61 | 71.8 |
| C.E. 7 | — | 68.6 | 31.41 | 58.4 |

Water absorption in polymers is known to have adverse effects on performance properties. For example, the material can increase in size, act as a plasticizer and decrease mechanical properties, and increase dielectric properties. In composites, absorbed water can increase hygroscopic stress through differential swelling and reduce interfacial adhesion between the matrix resin and the reinforcing fibers.

Water absorption was measured by immersion of cured test samples of example 7 and comparative example 7 in deionized water at 80° C. The water absorption was determined by removing the test samples periodically, weighing the test samples, and replacing them in the water. In addition, the growth of the sample through water absorption was determined by measuring the sample length.

Figure 17:
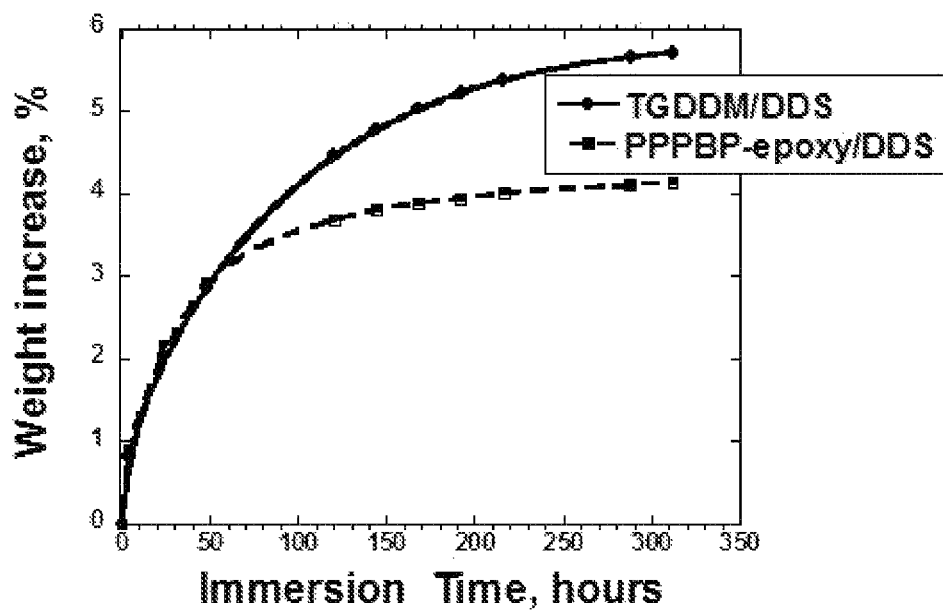
FIG. 17 is a graph depicting the water absorption (weight increase) of the PPPBP diglycidyl ether cured with DDS in comparison to TGDDM cured with DDS.
Figure 18:
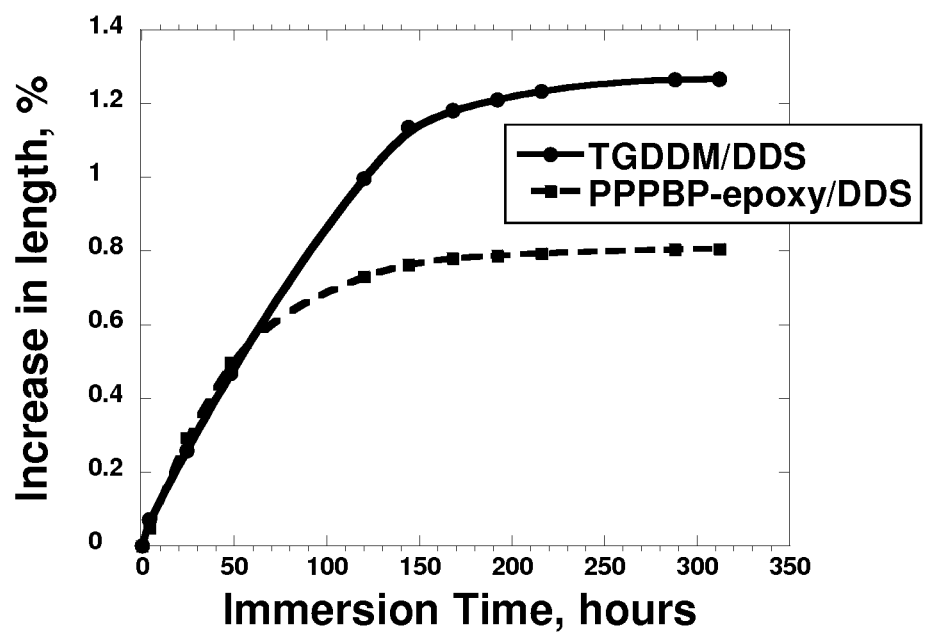
FIG. 18 is a graph depicting the water absorption (length increase) of the PPPBP diglycidyl ether cured with DDS in comparison to TGDDM cured with DDS.

The results for weight increase and increase in length of these two castings are shown in FIG. 17 and FIG. 18. As can be seen from FIG. 17, example 7 has 38% decreased water absorption compared to comparative example 7. In addition, FIG. 18 illustrates that comparative example 7 had 57% higher growth compared to example 7.

In general, thermoset resins shrink upon curing. Shrinkage can have negative effects on the performance of composites, such as the formation of residual stresses. Mechanical performance can also be adversely affected, including debonding at the resin-fiber interface and formation of micro-cracks.

Castings were cured according to the schedule described above. After the mold and casting were cooled to room temperature, the width of the mold was measured in 3 locations and the width of the cured epoxy was measured in the same 3 locations. The averages of the mold and casting measurements were determined. The percent shrinkage was determined by the following equation: Percent shrinkage=100*[(width mold−width casting)/(width mold)]. Table 15 shows that shrinkage for example 7 is significantly lower than that of comparative example 7.

Pot life is the time available after mixing of the curing agent with the epoxy before it attains an unusable form. In practice this generally relates to when the viscosity is too high or the resin gels. Long pot life is desirable for greater productivity. The pot life at 180° C. was determined using the spindle viscometer described above. Table 15 shows that pot life for example 7 is significantly higher than that of comparative example 7.

TABLE 15

| Ex. | PPPBP diglycidyl ether (wt %) | TGDDM (wt %) | DDS (wt %) | Shrinkage (%) | Gel time at 180° C. (min.) |
|---|---|---|---|---|---|
| 7 | 83.39 | — | 16.61 | 0.364 | >25 |
| C.E. 7 | — | 68.6 | 31.41 | 0.636 | 12 |

Imidazoles are used as catalytic curing agents or accelerators for other curing agents for epoxy resins. In general, imidazoles offer a balance of long pot life, faster curing speed, and higher Tg values of the cured epoxy. A comparison of imidazole cured PPPBP diglycidyl ether (example 9) and DGEBPA (comparative example 12) appears in Table 16. The samples were prepared by dissolving the 2,4-EMI in the epoxy, pouring the homogeneous solution into a mold and curing at 120° C. for 60 minutes, 150° C. for 60 minutes, 175° C. for 30 minutes, and 220° C. for 60 minutes.

Dielectric constants and loss tangent were measured at 23° C. according to IPC-TM-650 2.5.5.9. The samples were conditioned at 23° C. and 50% relative humidity for a minimum of 24 hours before testing. The measuring cell was a Hewlett-Packard Impedance Material Analyzer Model 4291B and had a width of 27.5 centimeters, a height of 9.5 centimeters, and a depth of 20.5 centimeters. The electrodes were Hewlett-Packard Model 16453A and had a diameter of 7 millimeters. Measurements were conducted using a capacitance method, sweeping a range of frequencies when DC voltage was applied to the dielectric materials. The applied voltage was 0.2 millivolt to 1 volt at the frequency of 1 gigahertz. Values for dielectric constants (Dk, relative permittivity) and loss tangent (Df, dissipation factor) at frequency of 1 gigahertz (1 GHz) were recorded and are reported in Table 16.

Controlling the heat of curing is useful in the avoidance of exotherms, especially in curing thick sections. As such, the heats of reaction for example 9 and comparative example 12 were also determined. To prepare these samples, the DDS hardeners were dissolved in the epoxy resins by warming and stirring. The formulations had 15-17% excess epoxy equivalents above the stoichiometric amount. The heats of reactions were measured by DSC as shown in Table 16. Comparative example 12 possessed 74% more heat from curing than example 9.

TABLE 16

| Example | PPPBP Epoxy (g) | DGEBPA (g) | 2,4-EMI (g) | Tg (° C.) | Dielectric constant at 1 GHz (Dk) | Loss tangent at 1 GHz (Df) | Heat of Reaction (J/g) |
|---|---|---|---|---|---|---|---|
| 9 | 50 | — | 0.6 | 210 | 2.98 | 0.01313 | 279 |
| C.E. 12 | — | 50 | 0.6 | 138 | 2.95 | 0.0143 | 509 |

Examples 10-27. Curing of Diglycidyl Ether of Bisphenols

The diglycidyl ethers of the bisphenols were cured using diamine and dianhydride curatives. The bisphenol diepoxy and curatives considered for the study is shown in Table 17.

TABLE 17

| | | HPLC purity (area %) | M.P (° C.) | EEW (g/Eq) | Residual ECH (ppm) |
|---|---|---|---|---|---|
| SBIBPDE | High purity diglycidyl ether of SBIBP | 99.5 | 129 | 211.2 | Below 5 |
| BPIDE | High purity diglycidyl ether of BPI | 98.6 | Liquid | 214.5 | Below 5 |
| BISAPDE | High purity diglycidyl ether of BISAP | 99.2 | Liquid | 204.6 | Below 5 |

EEW: epoxy equivalent weight estimated by $^1$HNMR,
ECH: epichlorohydrin

Solid hardeners were dissolved in the epoxy resin by mixing it at room temperature in a circular aluminum pan (Diameter~2.5 cm). The stoichiometry had 15-17% excess epoxy equivalents. The homogeneous epoxy/hardener mixtures were placed in an air circulated thermostatic oven. The cure program chosen is shown in Table 18.

TABLE 18

| Cure Temperature (° C.) | Cure time (min) |
|---|---|
| 90 | 30-40 |
| 120 | 30-40 |
| 150 | 30-40 |
| 180 | 30-40 |
| 200 | 30-40 |

The Tgs of the cured resin were estimated using a differential scanning calorimeter (DSC). The first scan was run from an initial temperature of 25° C. to a final temperature of 250° C., at a rate of 10° C./min. The sample was cooled at the rate of 10° C./min until 25° C./min and reheated until 250° C./min at the same rate. Tgs were estimated using both heat cycle thermograms. The compositions cured along with their Tg are given in Table 19. The diglycidyl ether of bisphenols listed in following table were high purity samples (HPLC purity~99%).

TABLE 19

| Example | BISAPDE (%) | SBIBPDE (%) | BPIDE (%) | HHA (%) | MNA (%) | MDA (%) | DDS (%) | EMI (%) | Tg (° C.) |
|---|---|---|---|---|---|---|---|---|---|
| 10 | 76.07 | | | 23.93 | | | | | 205.1 |
| 11 | 73.34 | | | | 26.66 | | | | 106.8 |
| 12 | 83.18 | | | | | 16.82 | | | 153.0 |
| 13 | 79.79 | | | | | | 20.21 | | 73.3 |
| 14 | 98.50 | | | | | | | 1.50 | 169.4 |
| 15 | | 76.65 | | 23.35 | | | | | ND |
| 16 | | 73.95 | | | 26.05 | | | | 154.0 |
| 17 | | 83.18 | | | | 16.82 | | | ND |
| 18 | | 79.79 | | | | | 20.21 | | ND |
| 19 | | 98.50 | | | | | | 1.50 | 147.0 |
| 20 | | | 76.64 | 23.36 | | | | | 146.0 |
| 21 | | | 73.95 | | 26.05 | | | | 106.5 |
| 22 | | | 83.62 | | | 16.38 | | | ND |
| 23 | | | 80.29 | | | | 19.71 | | ND |
| 24 | | | 98.50 | | | | | 1.50 | 146.0 |

ND: No transition detected

Upon curing, the compositions containing MDA (12, 17, 22) turned dark and bubbled. As a result, these compositions were cured at a lower temperature. The cure protocol used is shown in Table 20.

TABLE 20

| Cure Temperature (° C.) | Cure time (min) |
|---|---|
| 90 | 30-40 |
| 120 | 30-40 |
| 150 | 30-40 |

Examples 28-30 follow the cure program of Table 20 for curing MDA with the diglycidyl ether of Bisphenols (BISAP, BPI and SBIBP). Data are summarized in Table 21.

TABLE 21

| Example | BISAPDE (%) | SBIBPDE (%) | BPIDE (%) | MDA (%) | Tg (° C.) |
|---|---|---|---|---|---|
| 25 | 83.18 | | | 16.82 | 153 |
| 26 | | 83.18 | | 16.82 | 157 |
| 27 | | | 83.62 | 16.38 | 153 |

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

For reasons of completeness, various aspects of the present disclosure are set out in the following numbered clauses:

Clause 1. A compound having formula:

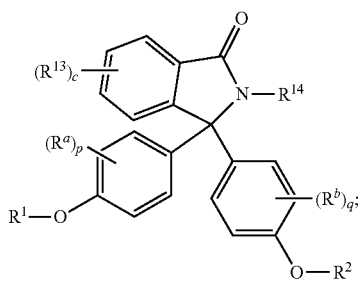

(I)

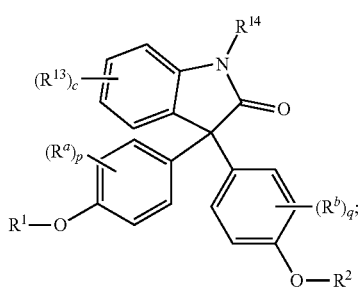

(II)

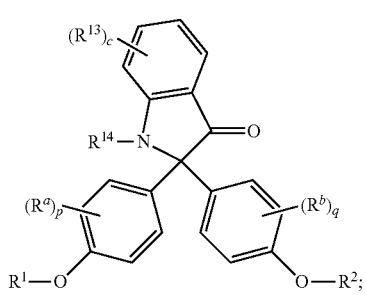

(III)

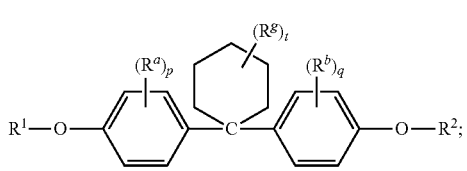

(IV)

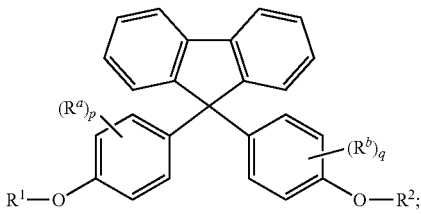

(V)

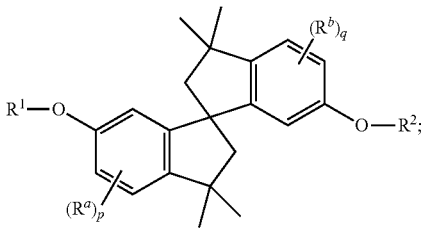

(VI)

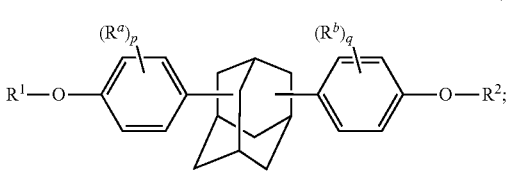

(VII)

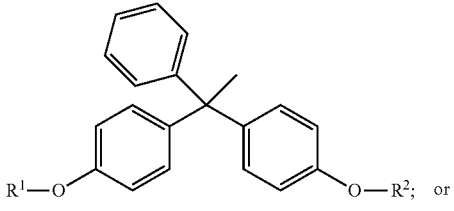

(VIII); or

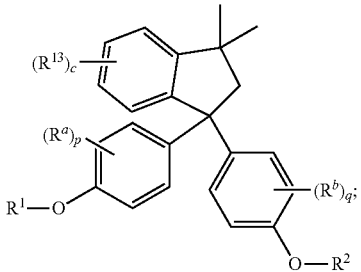

(IX)

wherein $R^1$ and $R^2$ at each occurrence are each independently selected from an epoxide-containing functional group; $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five, or six-membered cycloalkyl group; and t is 0 to 10; wherein the compound of formula (I) has a purity of 95% or greater, as determined by high performance liquid chromatography (HPLC).

Clause 2. The compound of clause 1, wherein $R^1$ and $R^2$ at each occurrence are each independently selected from:

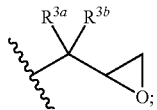

(5)

wherein $R^{3a}$ and $R^{3b}$ are each independently from hydrogen and $C_1$-$C_{12}$ alkyl.

Clause 3. The compound of clause 1 or clause 2, wherein the compound has a viscosity inversely proportional with the purity of the compound.

Clause 4. The compound of any one of clauses 1-3, selected from a compound having formula:

(1)

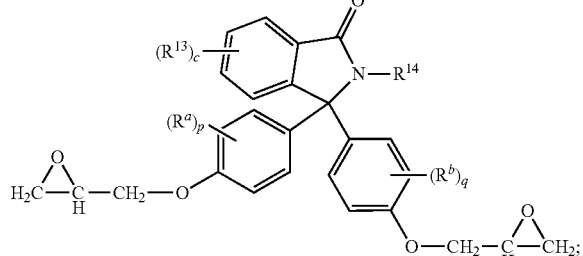

(2)

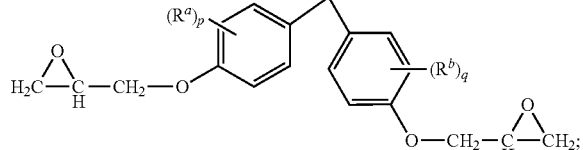

(3)

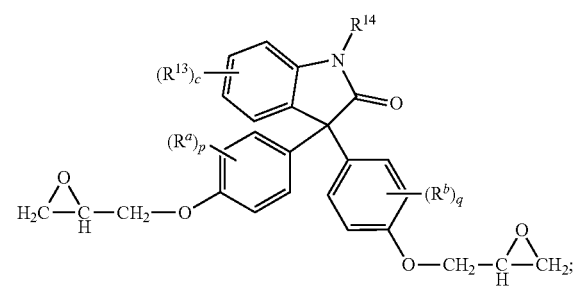

(4)

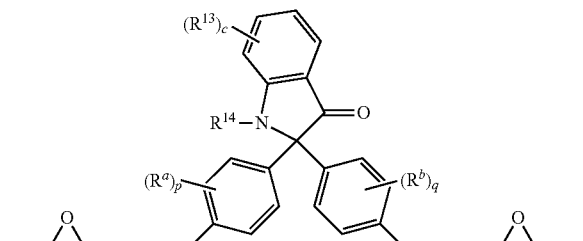

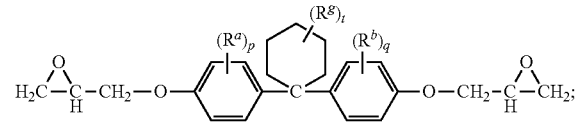

-continued (5)

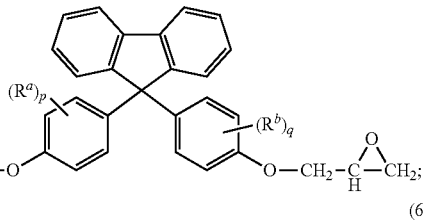

(6)

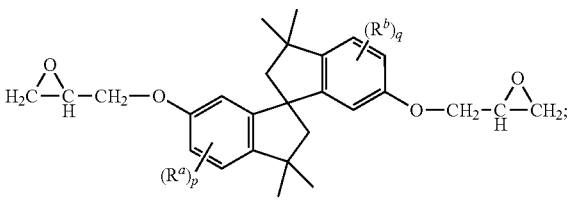

(7)

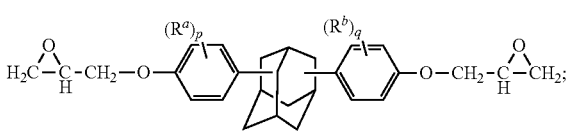

(8)

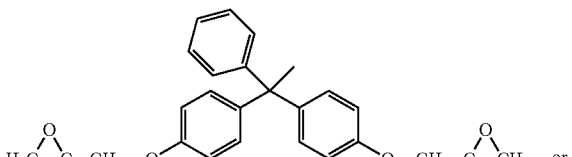

or (9)

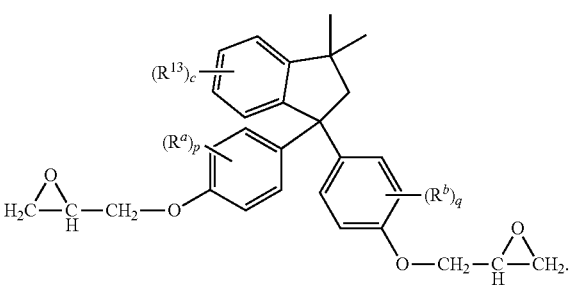

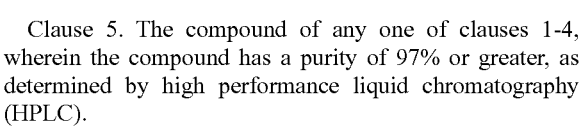

Clause 5. The compound of any one of clauses 1-4, wherein the compound has a purity of 97% or greater, as determined by high performance liquid chromatography (HPLC).

Clause 6. The compound of any one of clauses 1-5, wherein the compound has a purity of 98% or greater, as determined by high performance liquid chromatography (HPLC).

Clause 7. The compound of any one of clauses 1-6, wherein the compound has a purity of 99% or greater, as determined by high performance liquid chromatography (HPLC).

Clause 8. The compound of any one of clauses 1-7, wherein the compound is substantially free of oligomer impurities.

Clause 9. The compound of any one of clauses 1-8, having formula (1-a), (2-a), or (4-b) as described above.

Clause 10. The compound of any one of clauses 1-9, wherein the compound is derived from a compound of formula (1') as described above.

Clause 11. The compound of any one of clauses 1-10, wherein the compound is derived from a compound of formula (1'-a) as described above.

Clause 12. The compound of clause 11, wherein the compound of formula (1'-a) comprises less than 50 ppm of amino phenol impurities, less than 500 ppm of phenolphthalein, or 3 ppm or less of metal impurities.

Clause 13. A process for preparing a compound of formula (1) as described above, (1) wherein $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is each independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five, or six-membered cycloalkyl group; and t is 0 to 10; the process comprising: (a) providing a mixture of epichlorohydrin and a compound of formula (1') as described above, (b) slowly adding a base to the mixture of (a) to provide a reaction mixture; and (c) stirring the reacting mixture for 8 to 12 hours at 20° C. to 24° C.

Clause 14. The process of clause 13, wherein the base is sodium hydroxide or potassium hydroxide.

Clause 15. The process of clause 13 or clause 14, wherein the compound of formula (1) has a purity of 99% or greater, as determined by high performance liquid chromatography (HPLC).

Clause 16. The process of any one of clauses 13-15, wherein the compound of formula (1) has formula (1-a) as described above.

Clause 17. A curable composition comprising (i) a compound according to any one of clauses 1-12; (ii) a curing promoter; (iii) optionally an auxiliary epoxy resin different from the compound of (i); and (iv) optionally a polyphenylene ether resin of formula: R-W-R wherein W is a divalent poly(arylene ether) residue terminated with phenolic oxygen atoms; and each R is a functionalized benzyl group of formula:

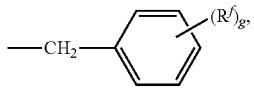

wherein $R^f$ at each occurrence is independently selected from acid, anhydride, amine, epoxy, oxazoline, orthoester, hydroxyl, phosphate, phosphonate, acrylate, ester, alkyne, alkene, alkenylthioate, alkenylsulfonate, and alkenylsulfonate, and g is 1, 2, 3, 4, or 5.

Clause 18. The curable composition of clause 17, wherein the auxiliary epoxy resin is selected from the group consisting of aliphatic epoxy resins, cycloaliphatic epoxy resins, bisphenol A epoxy resins, bisphenol-F epoxy resins, phenol novolac epoxy resins, cresol-novolac epoxy resins, biphenyl epoxy resins, polyfunctional epoxy resins, naphthalene epoxy resins, divinylbenzene dioxide, 2-glycidylphenylglycidyl ether, dicyclopentadiene-type epoxy resins, multi aromatic resin type epoxy resins, and mixtures thereof.

Clause 19. The curable composition of clause 17, wherein the auxiliary epoxy resin is a diglycidyl ether of 2,2-bis(4-hydroxyphenyl)propane.

Clause 20. The curable composition of clause 17, wherein the curing promoter is an amine compound.

Clause 21. The curable composition of clause 20, wherein the amine compound is selected from isophoronediamine, triethylenetetraamine, diethylenetriamine, aminoethylpiperazine, 1,2- and 1,3-diaminopropane, 2,2-dimethylpropylenediamine, 1,4-diaminobutane, 1,6-diaminohexane, 1,7-diaminoheptane, 1,8-diaminooctane, 1,9-diaminononane, 1,12-diaminododecane, 4-azaheptamethylenediamine, N,N'-bis(3-aminopropyl)butane-1,4-diamine, cyclohexanediamine, dicyanamide, diamide diphenylmethane, diamide diphenylsulfonic acid (amine adduct), 4,4'-methylenedianiline, diethyltoluenediamine, m-phenylenediamine, p-phenylenediamine, melamine formaldehyde resins, urea formaldehyde resins, tetraethylenepentamine, 3-diethylaminopropylamine, 3,3'-iminobispropylamine, 2,4-bis(p-aminobenzyl)aniline, tetraethylenepentamine, 3-diethylaminopropylamine, 2,2,4- and 2,4,4-trimethylhexamethylenediamine, 1,2- and 1,3-diaminocyclohexane, 1,4-diamino-3,6-diethylcyclohexane, 1,2-diamino-4-ethylcyclohexane, 1,4-diamino-3,6-diethylcyclohexane, 1-cyclohexyl-3,4-diminocyclohexane, 4,4'-diaminondicyclohexylmethane, 4,4'-diaminodicyclohexylpropane, 2,2-bis(4-aminocyclohexyl)propane, 3,3'-dimethyl-4,4'-diaminodicyclohexylmethane, 3-amino-1-cyclohexaneaminopropane, 1,3- and 1,4-bis(aminomethyl)cyclohexane, m- and p-xylylenediamine, diethyl toluene diamines, 4-aminophenyl sulfone, and mixtures thereof.

Clause 22. The curable composition of clause 20, wherein the amine compound is a tertiary amine hardening accelerator.

Clause 23. The curable composition of clause 22, wherein the tertiary amine hardening accelerator is selected from triethylamine, tributylamine, dimethylaniline, diethylaniline, benzyldimethylamine (BDMA), α-methylbenzyldimethylamine, N,N-dimethylaminoethanol, N,N-dimethylaminocresol, and tri(N,N-dimethylaminomethyl)phenol.

Clause 24. The curable composition of clause 20, wherein the amine compound is an imidazole hardening accelerator selected from 2-methylimidazole, 2-ethylimidazole, 2-laurylimidazole, 2-heptadecylimidazole, 2-phenylimidazole, 4-methylimidazole, 4-ethylimidazole, 4-laurylimidazole, 4-heptadecylimidazole, 2-phenyl-4-methylimidazole, 2-phenyl-4-hydroxymethylimidazole, 2-ethyl-4-methylimidazole, 2-ethyl-4-hydroxymethylimidazole, 1-cyanoethyl-4-methylimidazole, 2-phenyl-4,5-dihydroxymethylimidazole, and mixtures thereof.

Clause 25. The curable composition of clause 20, wherein the amine compound is a cyclic amidine hardening accelerator selected from 4-diazabicyclo(2,2,2)octane (DABCO), diazabicycloundecene (DBU), 2-phenyl imidazoline, and mixtures thereof.

Clause 26. The curable composition of clause 17, wherein the curing promoter is a phenolic hardener.

Clause 27. The curable composition of clause 26, wherein the phenolic hardener is selected from novolac type phenol resins, resole type phenol resins, aralkyl type phenol resins, dicyclopentadiene type phenol resins, terpene modified phenol resins, biphenyl type phenol resins, bisphenols, triphenylmethane type phenol resins, and mixtures thereof.

Clause 28. The curable composition of 17, wherein the curing promoter is an anhydride hardener selected from maleic anhydride (MA), phthalic anhydride (PA), hexahydro-o-phthalic anhydride (HEPA), tetrahydrophthalic anhydride (THPA), methyltetrahydrophthalic anhydride (MTHPA), methylhexahydrophthalic anhydride (MHHPA), nadic methyl anhydride (methyl himic anhydride, MHA), benzophenonetetracarboxylic dianydride (BTDA), tetrachlorophthalic anhydride (TCPA), pyromellitic dianhydride (PMDA), trimellitic anhydride (TMA), methyl-5-norbornene-2,3-dicarboxylic anhydride (MNA), hexahydrophthalic anhydride (1,2-cyclohexane dicarboxylic anhydride, (HHA)), and mixtures thereof.

Clause 29. The curable composition of clause 17, wherein the curing promoter is selected from latent cationic cure catalysts, copper (II) salts of aliphatic or aromatic carboxylic acids, aluminum (III) salts of aliphatic or aromatic carboxylic acids, tin (II) salts of aliphatic or aromatic carboxylic acids, copper (II) β-diketonates, aluminum (III) β-diketonates, tin (IV) tetrachloride, boron trifluoride-trialkylamine complexes, and mixtures thereof.

Clause 30. The curable composition of clause 17, wherein the curing promoter is a latent cationic cure catalyst selected from diaryliodonium salts, phosphonic acid esters, sulfonic acid esters, carboxylic acid esters, phosphonic ylides, triarylsulfonium salts, benzylsulfonium salts, aryldiazonium salts, benzylpyridinium salts, benzylammonium salts, isoxazolium salts, and combinations thereof.

Clause 31. The curable composition of clause 17, wherein the curing promoter is a latent cationic cure catalyst comprising a diaryliodonium salt having the structure $[(R^{10})(R^{11})I]^+ X^-$ wherein $R^{10}$ and $R^{11}$ are each independently a $C_6$-$C_{14}$ monovalent aromatic hydrocarbon radical, optionally substituted with from 1 to 4 monovalent radicals selected from $C_1$-$C_{20}$ alkyl, $C_1$-$C_{20}$ alkoxy, nitro, and chloro; and wherein $X^-$ is an anion.

Clause 32. The curable composition of clause 17, wherein the curing promoter has the structure $[(R^{10})(R^{11})I]^+ SbF_6^-$ wherein $R^{10}$ and $R^{11}$ are each independently a $C_6$-$C_{14}$ monovalent aromatic hydrocarbon radical, optionally substituted with from 1 to 4 monovalent radicals selected from $C_1$-$C_{20}$ alkyl, $C_1$-$C_{20}$ alkoxy, nitro, and chloro.

Clause 33. The curable composition of clause 17, wherein the curing promoter is a latent cationic cure catalyst comprising 4-octyloxyphenyl phenyl iodonium hexafluoroantimonate.

Clause 34. The curable composition of clause 17, wherein the curing promoter is a copper (II) or aluminum (III) salt of an aliphatic or aromatic carboxylic acid selected from copper (II), tin (II), and aluminum (III) salts of acetate, stearate, gluconate, citrate, benzoate, and mixtures thereof.

Clause 35. The curable composition of clause 17, wherein the curing promoter is a copper (II) or aluminum (III) β-diketonate selected from copper (II) and aluminum (III) salts of acetylacetonate.

Clause 36. The curable composition of clause 17, wherein the curing promoter is a boron trifluoride-trialkylamine complex.

Clause 37. The curable composition of clause 17, wherein the polyphenylene ether resin has formula:

Clause 38. A cured composition comprising the product obtained by curing the curable composition of any one of clauses 17-37.

Clause 39. The cured composition of clause 38, exhibiting a single Tg.

Clause 40. The cured composition of clause 38, exhibiting a single Tg of greater than or equal to 200° C.

Clause 41. The cured composition of clause 38, exhibiting a single Tg of greater than or equal to 225° C.

Clause 42. The cured composition of clause 38, exhibiting a single Tg of greater than or equal to 250° C.

Clause 43. An article comprising the cured composition of any one of clauses 38-42.

Clause 44. The article of clause 43, wherein the article is selected from acid bath containers; neutralization tanks; aircraft components; bridge beams; bridge deckings; electrolytic cells; exhaust stacks; scrubbers; sporting equipment; stair cases; walkways; automobile exterior panels; floor pans; air scoops; pipes; natural gas pipes; ducts; industrial fans; fan housings; blowers; industrial mixers; boat hulls; boat decks; marine terminal fenders; tiles; building panels; business machine housings; trays; concrete modifiers; dishwasher parts; refrigerator parts; electrical encapsulants; electrical panels; tanks; electrorefining tanks; water softener tanks; fuel tanks; filament-wound tanks; filamount-wound tank linings; furniture; garage doors; gratings; protective body gear; luggage; outdoor motor vehicles; pressure tanks; printed circuit boards; optical waveguides; radomes; railings; railroad parts; hopper car covers; car doors; truck bed liners; satellite dishes; signs; solar energy panels; telephone switchgear housings; tractor parts; transformer covers; truck parts; insulation for rotating machines; commutators; core insulation and cords and lacing tape; drive shaft couplings; propeller blades; missile components; rocket motor cases; wing sections; sucker rods; fuselage sections; wing skins; wing flairings; engine narcelles; cargo doors; tennis racquets; golf club shafts; fishing rods; skis; ski poles; bicycle parts; transverse leaf springs; pumps; automotive smog pumps; electrical components; embedding; tooling; electrical cable joints; wire windings; densely packed multielement assemblies; sealing of electromechanical devices; battery cases; resistors; fuses; thermal cut-off devices; coatings for printed wiring boards; casting items; capacitors; transformers; crankcase heaters; small molded electronic parts; coils; semiconductors; chemical processing parts; pulp and paper machine parts; power generation parts; wastewater treatment parts; scrubbing towers; pultruded parts for structural applications; structural members; gratings; safety rails; swimming pools; swimming pool slides; hot-tubs; saunas; drive shafts for under the hood applications; dry toner resins for copying machines; marine tooling; marine composites; heat shields; submarine hulls; prototype generation parts; laminated trim; drilling fixtures; bonding jigs; inspection fixtures; industrial metal forming dies; air-

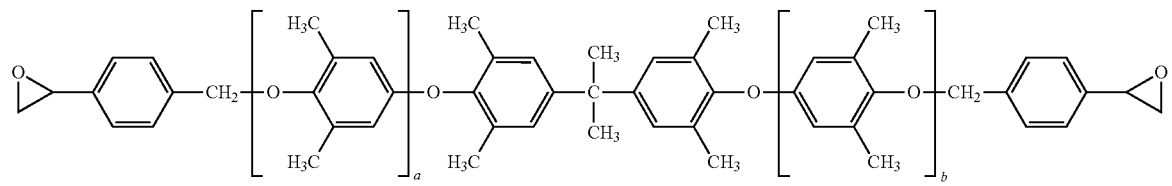

wherein each occurrence of a and b is independently 0 to 20, provided that the sum of a and b is at least 2.

craft stretch block and hammer forms; vacuum molding tools; flooring; flooring for production and assembly areas; flooring for clean rooms; flooring for machine shops; flooring for control rooms; flooring for laboratories; flooring for parking garages; flooring for freezers; flooring for coolers;

flooring for outdoor loading docks; electrically conductive compositions for antistatic applications; decorative flooring; expansion joints for bridges; injectable mortars for patch and repair of cracks in structural concrete; grouting for tile; machinery rails; metal dowels; bolts and posts; repair material for oil and fuel storage tanks; sport equipment; media equipment; grinding wheels; sanding wheels; mechanical rollers; conveyor belts; military equipment; space equipment; aerospace components; automotive components; mass transportation components; printed circuit boards; electrical components; optical components; optoelectrical components; computer components; watercraft exterior components; watercraft interior components; gas storage tanks; and wind turbines.

Clause 45. The article of clause 43, wherein the article is selected from aerospace components, automotive components, mass transportation components, printed circuit boards, electrical components, optical components, optoelectrical components, computer components, watercraft exterior components, and watercraft interior components.

Clause 46. The article of any one of clauses 43-45, wherein the article is produced by resin transfer molding; sheet molding; bulk molding; pultrusion; injection molding; reaction injection molding (RIM); atmospheric pressure molding (APM); casting; centrifugal casting; static casting; open mold casting; lamination; contact molding; cylindrical contact molding; compression molding; vacuum assisted resin transfer molding; chemically assisted resin transfer molding; matched tool molding; autoclave curing; thermal curing in air; vacuum bagging; Seeman's Composite Resin Infusion Manufacturing Processing (SCRIMP); open molding; filament winding; cylindrical filament winding; or a combination thereof.

Clause 47. A material comprising the cured composition of any one of clauses 38-42, wherein the material is a composite, a coating, an adhesive, an encapsulant, or a sealant.

Clause 48. The material of clause 47, wherein the material comprises one or more additional components, each independently selected from flame retardants, fillers, reinforcing fibers, dyes, pigments, colorants, antioxidants, heat stabilizers, light stabilizers, plasticizers, lubricants, flow modifiers, drip retardants, antiblocking agents, antistatic agents, flow-promoting agents, processing aids, substrate adhesion agents, mold release agents, toughening agents, low-profile additives, stress-relief additives, and combinations thereof.

Clause 49. The material of clause 48, wherein the filler is selected from: alumina, silica, boron nitride aluminum nitride, silicon nitride, magnesia, magnesium silicate, glass fibers, glass mat, silica powder, fumed silica, spherical silica, thiourea, $Al_2O_3$, talc, kaolin, clay, antimony trioxide, glass bubbles, hollow glass microsphere, aramid fibers, and quartz.

Clause 50. The material of any one of clauses 47-49, wherein the composite is a glass fiber based composite, a carbon fiber based composite, or a combination thereof.

Clause 51. The material of clause any one of clauses 47-50, wherein the material is produced by a resin transfer molding process.

Clause 52. The compound of any one of clauses 1-12, having a softening point of less than 50° C., as measured according to ASTM E28-1999.

Clause 53. The cured composition of clauses 38-42, having an impact strength of greater than or equal to 60 J/m, 65 J/m, or 70 Jim as measured according to ASTM D4812-2006.

What is claimed is:

1. A compound having formula:

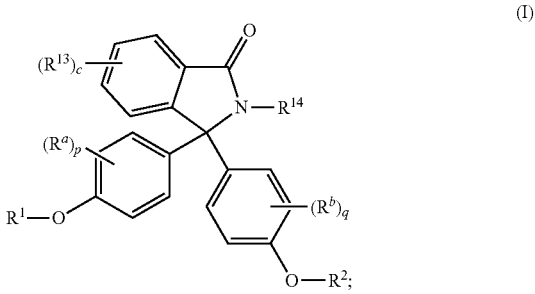

(I)

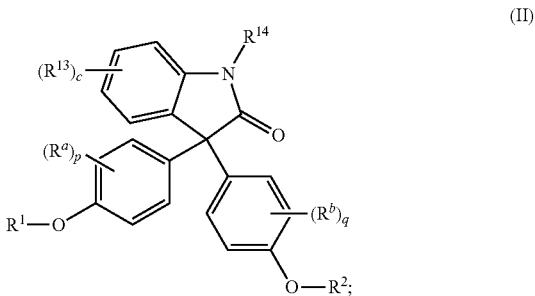

(II)

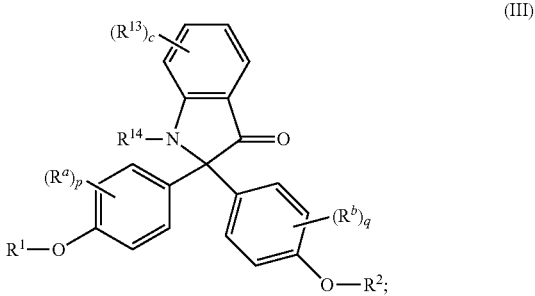

(III)

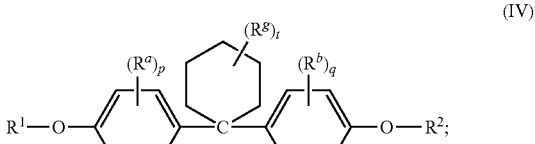

(IV)

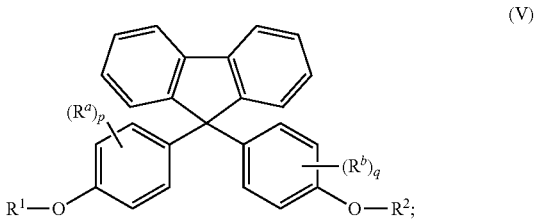

(V)

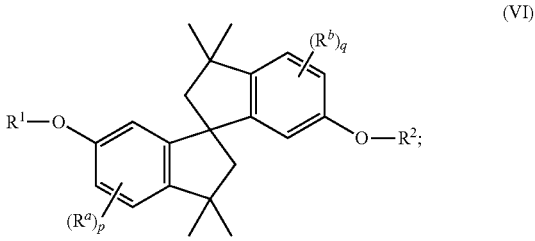

(VI)

-continued

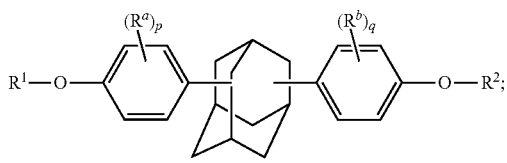
(VII)

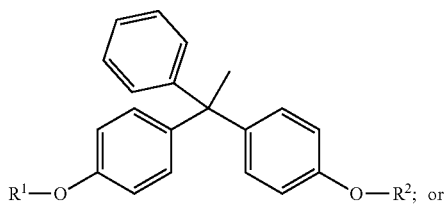
(VIII)

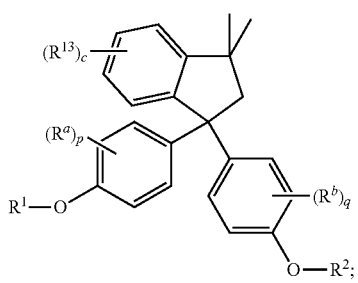
(IX)

wherein $R^1$ and $R^2$ at each occurrence are each independently selected from an epoxide-containing functional group; $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five-, or six-membered cycloalkyl group; and t is 0 to 10;

wherein the compound has a purity of 97% or greater, as determined by high performance liquid chromatography (HPLC);

the compound has an oligomer impurity content of less than or equal to 1%, as determined by high performance liquid chromatograph, and the compound has a softening point of less than 50° C., as measured according to ASTM E28-1999.

2. The compound of claim 1, wherein $R^1$ and $R^2$ at each occurrence are each selected from:

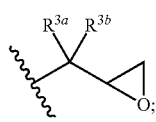

wherein $R^{3a}$ and $R^{3b}$ are each independently selected hydrogen and $C_1$-$C_{12}$ alkyl.

3. The compound of claim 1, wherein the compound is substantially free of oligomer impurities.

4. The compound of claim 1, having formula (1-a), (2-a), or (4-b)

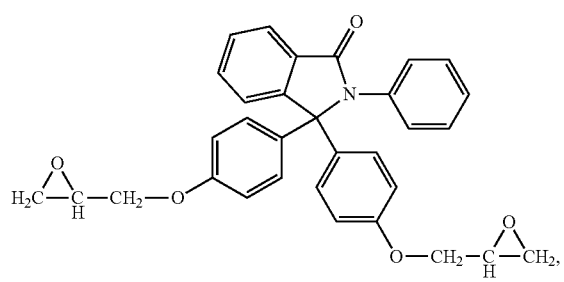
(1-a)

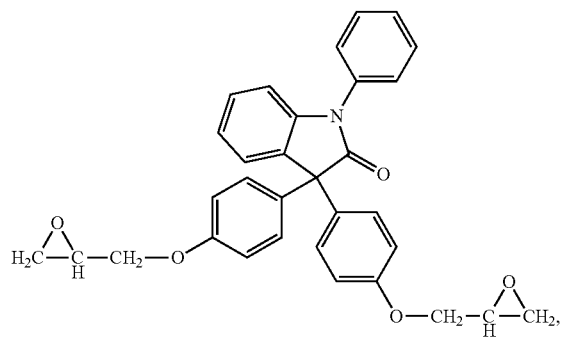
(2-a)

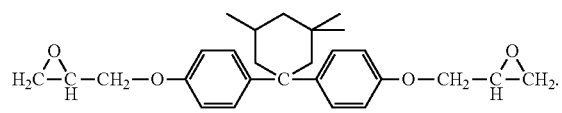
(4-b)

5. The compound of claim 4, wherein the compound has an oligomer impurity content of less than or equal to 0.5%, as determined by high performance liquid chromatography.

6. The compound of claim 4, wherein the compound has an oligomer impurity content of less than or equal to 0.1%, as determined by high performance liquid chromatography.

7. The compound of claim 4, wherein the compound has formula (1-a).

8. The compound of claim 4, wherein the compound has formula (2-a).

9. The compound of claim 4, wherein the compound has formula (4-b).

10. The compound of claim 1, wherein the compound has a metal impurity content of 1 ppm or less.

11. The compound of claim 1, wherein the compound has a color APHA value of 20 or less, as measured using test method ASTM D1209.

12. The compound of claim 1, having formula (4-c):

(4-c)

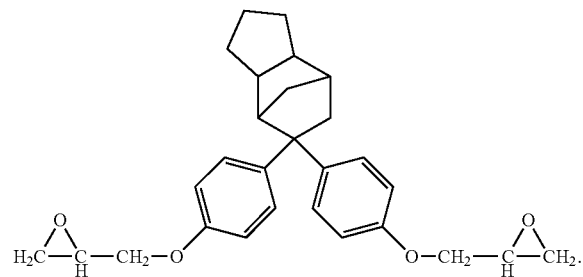

13. The compound of claim 1, having formula (6-a):

(6-a)

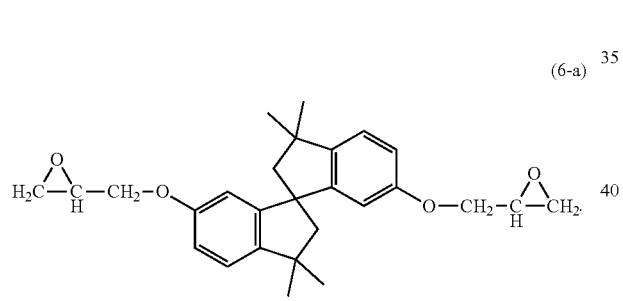

14. The compound of claim 1, having formula (7-a):

(7-a)

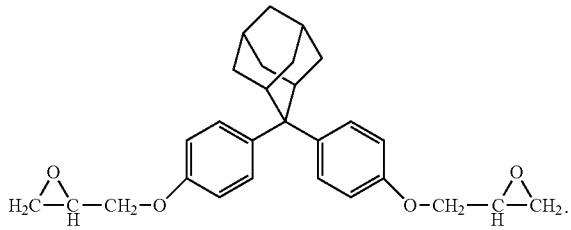

15. The compound of claim 1, having formula (8-a):

(8-a)

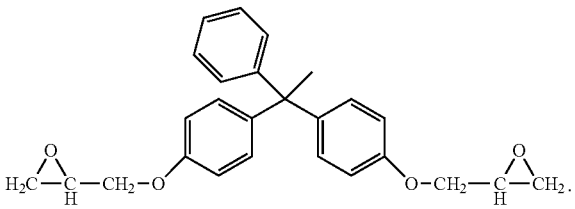

16. The compound of claim 1, having formula (9-a):

(9-a)

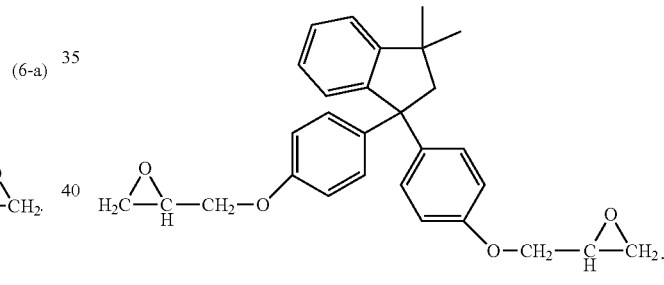

* * * * *